US011052160B2

(12) United States Patent
Gonzalez et al.

(10) Patent No.: US 11,052,160 B2
(45) Date of Patent: Jul. 6, 2021

(54) SELECTIVE DELIVERY MOLECULES AND METHODS OF USE

(71) Applicant: Avelas Biosciences, Inc., La Jolla, CA (US)

(72) Inventors: Jesus Gonzalez, Carlsbad, CA (US); Junjie Liu, San Diego, CA (US)

(73) Assignee: Avelas Biosciences, Inc., La Jolla, CA (US)

( * ) Notice: Subject to any disclaimer, the term of this patent is extended or adjusted under 35 U.S.C. 154(b) by 9 days.

(21) Appl. No.: 16/264,296

(22) Filed: Jan. 31, 2019

(65) Prior Publication Data

US 2019/0151481 A1 May 23, 2019

Related U.S. Application Data

(63) Continuation of application No. 15/685,942, filed on Aug. 24, 2017, now Pat. No. 10,226,539, which is a continuation of application No. 14/764,681, filed as application No. PCT/US2014/013942 on Jan. 30, 2014, now Pat. No. 9,782,498.

(60) Provisional application No. 61/758,680, filed on Jan. 30, 2013.

(51) Int. Cl.
*A61K 49/00* (2006.01)
*A61K 49/14* (2006.01)
*A61K 47/60* (2017.01)
*A61K 47/64* (2017.01)
*A61K 47/65* (2017.01)

(52) U.S. Cl.
CPC .......... *A61K 49/0056* (2013.01); *A61K 47/60* (2017.08); *A61K 47/64* (2017.08); *A61K 47/65* (2017.08); *A61K 49/0032* (2013.01); *A61K 49/0054* (2013.01)

(58) Field of Classification Search
CPC .... A61K 49/00; A61K 49/14; A61K 49/0056; A61K 49/0032; A61K 49/0054; A61K 47/00; A61K 47/65; A61K 47/60; A61K 47/64; A61K 2121/00; A61K 38/00; A61P 35/00
USPC .......... 424/1.11, 1.65, 1.69, 1.81, 1.85, 1.89, 424/9.1, 9.2, 9.3, 9.4, 9.5, 9.6; 530/300, 530/317, 326; 514/1, 1.1, 19.2, 19.3, 514/19.4, 19.5, 19.6
See application file for complete search history.

(56) References Cited

U.S. PATENT DOCUMENTS

| | | |
|---|---|---|
| 4,439,356 A | 3/1984 | Khanna et al. |
| 4,452,720 A | 6/1984 | Harada et al. |
| 4,466,919 A | 8/1984 | Weingarten |
| 4,496,542 A | 1/1985 | Skiles et al. |
| 4,507,389 A | 3/1985 | Weingarten |
| 5,066,580 A | 11/1991 | Lee |
| 5,227,487 A | 7/1993 | Haugland et al. |
| 5,434,073 A | 7/1995 | Dawson et al. |
| 5,543,295 A | 8/1996 | Bronstein et al. |
| 5,674,980 A | 10/1997 | Frankel et al. |
| 5,747,641 A | 5/1998 | Frankel et al. |
| 5,750,409 A | 5/1998 | Herrmann et al. |
| 5,910,300 A | 6/1999 | Tournier et al. |
| 5,936,087 A | 8/1999 | Benson et al. |
| 6,008,379 A | 12/1999 | Benson et al. |
| 6,025,505 A | 2/2000 | Lee et al. |
| 6,080,852 A | 6/2000 | Lee et al. |
| 6,083,486 A | 7/2000 | Weissleder et al. |
| 6,306,993 B1 | 10/2001 | Rothbard et al. |
| 6,316,003 B1 | 11/2001 | Frankel et al. |
| 6,348,185 B1 | 2/2002 | Piwnica-Worms |
| 6,495,663 B1 | 12/2002 | Rothbard et al. |
| 6,592,847 B1 | 7/2003 | Weissleder et al. |
| 6,630,351 B1 | 10/2003 | Monahan et al. |
| 7,431,915 B2 | 10/2008 | Jiang et al. |
| 7,985,401 B2 | 7/2011 | Jiang et al. |
| 8,110,554 B2 | 2/2012 | Jiang et al. |
| 8,486,373 B2 | 7/2013 | Weissleder et al. |
| 8,642,561 B2 | 2/2014 | Jiang et al. |
| 8,685,372 B2 | 4/2014 | Tsien et al. |
| 9,072,792 B2 | 7/2015 | Jiang et al. |
| 9,278,144 B2 * | 3/2016 | Liu .................... A61K 49/0056 |
| 9,371,367 B1 | 6/2016 | Gonzalez et al. |
| 9,504,763 B2 * | 11/2016 | Gonzalez .......... A61K 49/0054 |
| 9,682,151 B2 | 6/2017 | Tsien et al. |
| 9,695,251 B2 | 7/2017 | Tsien et al. |
| 9,782,498 B2 * | 10/2017 | Gonzalez ............... A61K 47/65 |

(Continued)

FOREIGN PATENT DOCUMENTS

| | | |
|---|---|---|
| CN | 102159189 A | 8/2011 |
| CN | 102438659 A | 5/2012 |

(Continued)

OTHER PUBLICATIONS

Abdollahi et al. Inhibition of αVβ3 Integrin Survival Signaling Enhances Antiangiogenic and Antitumor Effects of Radiotherapy. Clin Cancer Res. 11(17):6270-6279 (Sep. 1, 2005).

(Continued)

*Primary Examiner* — D. L. Jones

(74) *Attorney, Agent, or Firm* — Goodwin Procter LLP

(57) ABSTRACT

Disclosed herein is a selective delivery molecule comprising: (a) an acidic sequence (portion A) which is effective to inhibit or prevent the uptake into cells or tissue retention, (b) a molecular transport or tissue retention sequence (portion B), and (c) a linker between portion A and portion B, and (d) cargo moieties (portion $D_A$ and $D_B$).

1 Claim, 6 Drawing Sheets

Specification includes a Sequence Listing.

(56) References Cited

U.S. PATENT DOCUMENTS

| | | | |
|---|---|---|---|
| 9,808,532 | B2 | 11/2017 | Tsien et al. |
| 9,840,537 | B2* | 12/2017 | Gonzalez ............ A61K 49/0054 |
| 10,226,539 | B2* | 3/2019 | Gonzalez ............ A61K 49/0056 |
| 10,239,919 | B2 | 3/2019 | Gonzalez et al. |
| 10,259,845 | B2 | 4/2019 | Jiang et al. |
| 2002/0009786 | A1 | 1/2002 | Tang et al. |
| 2003/0176335 | A1 | 9/2003 | Zhang et al. |
| 2004/0009122 | A1 | 1/2004 | Klaveness et al. |
| 2004/0241096 | A1 | 12/2004 | Bogdanov et al. |
| 2005/0069494 | A1 | 3/2005 | Li et al. |
| 2007/0041904 | A1 | 2/2007 | Jiang et al. |
| 2009/0004118 | A1 | 1/2009 | Nie et al. |
| 2011/0160147 | A1 | 6/2011 | Dal et al. |
| 2012/0148610 | A1 | 6/2012 | Doronina et al. |
| 2013/0020537 | A1 | 1/2013 | Maruno et al. |
| 2013/0176335 | A1 | 7/2013 | Sugiyama et al. |
| 2016/0082119 | A1 | 3/2016 | Gonzalez et al. |
| 2017/0305968 | A1 | 10/2017 | Tsien et al. |

FOREIGN PATENT DOCUMENTS

| | | |
|---|---|---|
| EP | 2399939 A2 | 12/2011 |
| JP | 2007519420 A | 7/2007 |
| JP | 2011526780 A | 10/2011 |
| JP | 2012504136 A | 2/2012 |
| WO | WO-0175067 A2 | 10/2001 |
| WO | WO-2005042034 A1 | 5/2005 |
| WO | WO-2005074546 A2 | 8/2005 |
| WO | WO-2006125134 A1 | 11/2006 |
| WO | WO-2009100255 A2 | 8/2009 |
| WO | WO-2010036964 A2 | 4/2010 |
| WO | WO-2011008992 A2 | 1/2011 |
| WO | WO-2012107577 A1 | 8/2012 |
| WO | WO-2013019681 A2 | 2/2013 |
| WO | WO-2014120837 A2 | 8/2014 |
| WO | WO-2014120974 A1 | 8/2014 |
| WO | WO-2014176284 A1 | 10/2014 |

OTHER PUBLICATIONS

Adams et al. Anti-tubulin drugs conjugated to anti-ErbB antibodies selectively radiosensitize. Nat Commun 7:13019 (pp. 1-11) (Oct. 4, 2016).

Advani et al. Increased oncolytic efficacy for high-grade gliomas by optimal integration of ionizing radiation into the replicative cycle of HSV-1. Gene Therapy 18:1098-1102 (2011).

Advani et al. Preferential Replication of Systemically Delivered Oncolytic Vaccinia Virus in Focally Irradiated Giloma Xenografts. Clin Cancer Res. 18(9):2579-2590 (2012).

Aguilera et al. Systemic in vivo distribution of activatable cell penetrating peptides is superior to that of cell penetrating peptides. Integr Biol (Camb). 1(5-6):371-381 (2009).

Akashi et al. The novel microtubule-interfering agent TZT-1027 enhances the anticancer effect of radiation in vitro and in vivo. Br J Cancer 96:1532-1539 (2007).

Arnold et al. Substrate specificity of cathepsins D and E determined by N-terminal and C-terminal sequencing of peptide pools. Eur J Biochem 249:171-179 (1997).

Arslan et al. Cytosolic Ca2+ homeostasis in Ehrlich and Yoshida carcinomas. A new, membrane-permeant chelator of heavy metals reveals that these ascites tumor cell lines have normal cytosolic free Ca2+. J. Biol. Chem. 260:2719-2727 (1985).

Bai et al. Dolastatin 10, a powerful cytostatic peptide derived from a marine animal. Inhibition of tubulin polymerization mediated through the vinca alkaloid binding domain. Biochem Pharmacol 39:1941-1949 (1990).

Bartles et al. Identification and characterization of espin, an actin-binding protein localized to the F-actin-rich junctional plaques of Sertoli cell ectoplasmic. Journal of Cell Science 109(6):1229-1239 (1996).

Bhorade et al. Macrocyclic Chelators with Paramagnetic Cations Are Internalized into Mammalian Cells via a HIV-Tat Derived Membrane Translocation Peptide. Bioconjugate Chemistry 11(3):301-305 (May/Jun. 2000).

Blum et al. Noninvasive optical imaging of cysteine protease activity using fluorescently quenched activity-based probes. Nat Chem Biol 3(10):668-677 (Oct. 2007).

Breij et al. An Antibody-Drug Conjugate That Targets Tissue Factor Exhibits Potent Therapeutic Activity against a Broad Range of Solid Tumors. Cancer Res 74(4):1214-1226 (Feb. 15, 2014).

Bremer et al. In vivo molecular target assessment of matrix metalloproteinase inhibition. Nat. Med. 7:743-748 (2001).

Bremer et al. Optical Imaging of Matrix Metalloproteinase-2 Activity in Tumors Feasibility Study in a Mouse Model. Radiology 221:523-529 (2001).

Bremer et al. Optical Imaging of Spontaneous Breast Tumors Using Protease Sensing 'Smart' Optical Probes. Invest Radiol 40(6):321-327 (Jun. 6, 2005).

Buckel et al. Tumor Radiosensitization by Monomethyl Auristatin E; Mechanism of Action and Targeted Delivery. Cancer Res 75(7):1376-1387 (Apr. 1, 2015).

Bullok et al. Characterization of novel histidine-tagged Tat-peptide complexes dual-labeled with (99m)Tc-tricarbonyl and fluorescein for scintigraphy and fluorescence microscopy. Bioconjugate Chem. 13:1226-1237 (2002).

Chaurand et al. Molecular imaging of thin mammalian tissue sections by mass spectrometry. Curr Opinion Biotechnol 17(4):431-436 (2006).

Chen et al. A unique substrate recognition profile for matrix metalloproteinase-2. J Biol Chem 277(6):4485-4491 (2002).

Chen et al. Thrombin Activity Associated with Neuronal Damage during Acute Focal Ischemia. The Journal of Neuroscience 32(22):7622-7631 (2012).

Chen et al. Zipper Molecular Beacons: A Generalized Strategy to Optimize the Performance of Activatable Proteases Probes. Bioconjugate Chemistry 20:1836-1842 (2009).

Close. Matrix metalloproteinase inhibitors in rheumatic diseases. Ann. Rheum. Dis. 60(Suppl.)3:62-67 (2001).

Cooks et al. Detection Technologies. Ambient Mass Spectrometry. Science 311(5767):1566-1570 (2006).

Crisp et al. Dual Targeting of Integrin αvβ3 and Matrix Metalloproteinase-2 for Optical Imaging of Tumors and Chemotherapeutic Delivery. Mol Cancer Ther 13(6):1514-1525 (2014).

De Grand et al. An operational near-infrared fluorescence imaging system prototype for large animal surgery. Technol. Cancer Res. Treat. 2:553-562 (2003).

Derossi et al. Trojan peptides: the penetratin system for intracellular delivery. Trends in Cell Biology 8:84-87 (1998).

Doronina et al. Development of potent monoclonal antibody auristatin conjugates for cancer therapy. Nat Biotechnol 21:778-784 (2003).

Drake et al. Activatable Optical Probes for the Detection of Enzymes. Curr Org Synth 8(4):498-520 (2011).

Dubowchik et al. Cathepsin B-Sensitive Dipeptide Prodrugs. 2. Models of Anticancer Drugs Paclitaxel (Taxol), Mitomycin C and Doxorubicin. Bioorg Med Chem Letts 8:3347-3352 (1998).

Duffy et al. The ADAMs family of proteins: from basic studies to potential clinical applications. Thromb. Haemost. 89:622-631 (2003).

Duncan. The dawning era of polymer therapeutics. Nat. Rev. Drug Discovery 2:347-360 (2003).

Egami et al. Up-regulation of integrin β3 in radioresistant pancreatic cancer impairs adenovirus-mediated gene therapy. Cancer Sci 100(10):1902-1907 (2009).

Egeblad et al. New functions for the matrix metalloproteinases in cancer progression. Nat. Rev. 2:161-174 (2002).

Etzioni et al. The case for early detection. Nat. Rev. Cancer 3:243-252 (2003).

Fawell et al. Tat-mediated delivery of heterologous proteins into cells. PNAS 91:664-668 (1994).

Franc et al. Breaching biological barriers: protein translocation domains as tools for molecular imaging and therapy. Mol. Imaging 2:313-323 (2003).

Fujita et al. X-ray irradiation and Rho-kinase inhibitor additively induce invasiveness of the cells of the pancreatic cancer line,

(56) References Cited

OTHER PUBLICATIONS

MIAPaCa-2, which exhibits mesenchymal and amoeboid motility. Cancer Sci. 102(4):792-798 (2011).
Funovics et al. Catheter-based in vivo imaging of enzyme activity and gene expression: feasibility study in mice. Radiology 231:659-666 (2004).
Funovics et al. Protease sensors for bioimaging. Anal. Bioanal. Chem. 377:956-963 (2003).
Futaki et al. Stearylated arginine-rich peptides: a new class of transfection systems. Bioconj. Chem. 12:1005-1011 (2001).
Gallwitz at al. The Extended Cleavage Specificity of Human Thrombin. PLoS ONE 12(2):e.31756, pp. 1-16 (2012).
Gammon et al. Quantitative analysis of permeation peptide complexes labeled with Technetium-99m: chiral and sequence-specific effects on net cell uptake. Bioconjugate Chem. 14:368-376 (2003).
Giustini et al. Ionizing radiation increases systemic nanoparticle tumor accumulation. Nanomedicine 8:818-821 (2012).
Golub et al. Molecular Classification of Cancer: Class Discovery and Class Prediction by Gene Expression Monitoring. Science 286:531-537 (1999).
Gounaris et al. Live Imaging of Cysteine-Cathepsin Activity Reveals Dynamics of Focal Inflammation, Angiogenesis, and Polyp Growth. PLoS One 3(8):e2916 (pp. 1-9) (2008).
Hallahan et al. Integrin-mediated targeting of drug delivery to irradiated tumor blood vessels. Cancer Cell 3:63-74 (2003).
Hallahan et al. Radiation-mediated control of drug delivery. Am J Clin Oncol 24:473-480 (2001).
Hallahan et al. Spatial and temporal control of gene therapy using ionizing radiation. Nat Med 1:786-791 (1995).
Hallbrink et al. Cargo delivery kinetics of cell-penetrating peptides. Biochim. Biophys. Acta 1515:101-109 (2001).
Hariri et al. Radiation-Guided Drug Delivery to Mouse Models of Lung Cancer. Clin Cancer Res 16(1):4968-4977 (2010).
Harris. Monoclonal antibodies as therapeutic agents for cancer. Lancet Oncol. 5:292-302 (2004).
Held. An introduction to fluorescence resonance energy transfer (FRET) technology and its application in bioscience. BioTek Jun. 20, 2015 (http://www.biotek.com/assets/tech resources/FRET%20White%20Paper.pdf) (6 pgs.).
Hutteman et al. Optimization of Near-Infrared Fluorescent Sentinel Lymph Node Mapping for Vulvar Cancer. Am J Obstet Gynecol. 206(1):89.e1-89.e5 (2012).
Ifa et al. Ambient Ionization Mass Spectrometry for Cancer Diagnosis and Surgical Margin Evaluation. Clin Chem 62(1):111-123 (2016).
Jaffer et al. In Vivo Imaging of Thrombin Activity in Experimental Thrombi With Thrombin-Sensitive Near-Infrared Molecular Probe, Arteriosclerosis. Thrombosis and Vascular Biology 22:1929-1935 (2002).
Jiang et al. Tumor imaging by means of proteolytic activation of cell-penetrating peptides. PNAS 101(51):17867-17872 (Dec. 21, 2004).
Joh et al. Selective Targeting of Brain Tumors with Gold Nanoparticle-Induced Radiosensitization. PLoS One 8(4):e62425 (pp. 1-10) (2013).
Kacprzak et al. Inhibition of furin by polyarginine-containing peptides: nanomolar inhibition by nona-D-arginine J. Biol. Chem. 279:36788-36794 (2004).
Ke et al. Optimal subsite occupancy and design of a selective inhibitor of urokinase. J. Biol. Chem. 272:20456-20462 (1997).
Kopecek et al .Water soluble polymers in tumor targeted delivery. J. Controlled Release 74:147-158 (2001).
Kumar et al. Increased type-IV collagenase (MMP-2 and MMP-9) activity following preoperative radiotherapy in rectal cancer. Br J Cancer 82(4):960-965 (2000).
La Rocca et al. Zymographic detection and clinical correlations of MMP-2 and MMP-9 in breast cancer sera. Br. J. Cancer 90:1414-1421 (2004).
Lanekoff et al. Automated Platform for High-Resolution Tissue Imaging Using Nanospray Desorption Electrospray Ionization Mass Spectrometry. Anal Chem 84(19):8351-8356 (2012).
Laskin et al. Ambient Mass Spectrometry Imaging Using Direct Liquid Extraction Techniques. Anal. Chem 88(1):52-73 (2016).
Leake et al. Brain matrix metalloproteinase 1 levels are elevated in Alzheimer's disease. Neurosci. Lett. 291:201-203 (2000).
Lee et al. Activatable molecular probes for cancer imaging. Curr Top Med Chem 10(11):1135-1144 (2010).
Levenson et al. Review Article: Modern Trends in Imaging X: Spectral imaging in preclinical research and clinical pathology. Anal Cell Pathol 35:339-361 (2012).
Levi et al. Design, Synthesis and Imaging of an Activatable Photoacoustic Probe. J Am Chem Soc. 132(32):11264-11269 (2010).
Lewin et al. Tat peptide-derivatized magnetic nanoparticles allow in vivo tracking and recovery of progenitor cells. Nat. Biotech. 18:410-414 (2000).
Li et al. Tumor Irradiation Enhances the Tumor-specific Distribution of Poly(L-glutamate acid)-conjugated Paclitaxel and Its Antitumor Efficacy. Clin Cancer Res 6:2829-2834 (2000).
Liauw et al. New paradigms and future challenges in radiation oncology: an update of biological targets and technology. Sci Transl Med 5:173sr2 (2013).
Lin et al. Opportunities and Challenges in the Era of Molecularly Targeted Agents and Radiation Therapy. J Natl Cancer Inst 105:686-693 (2013).
Linder et al. Synthesis, In Vitro Evaluation, and in Vivo Metabolism of Fluor/Quencher Compounds Containing IRDye 800CW and Black Hole Quencher 3 (BHQ-3). Bioconjugate Chemistry 22:1287-1297 (2011).
Liu et al. Lessons Learned from Radiation Oncology Clinical Trials. Clin Cancer Res 19(22):6089-6100 (2013).
Lohela et al. Intravital imaging of stromal cell dynamics in tumors. Curr Opin Genet Dev 20(1):72-78 (2010).
Lundberg et al. Cell surface adherence and endocytosis of protein transduction domains. Mol. Ther. 8:143-150 (2003).
Luo et al. Cancer-targeted polymeric drugs. Current Cancer Drug Targets 2:209-226 (2002).
Ma et al. Potent Antitumor Activity of an Auristatin-Conjugated, Fully Human Monoclonal Antibody to Prostate-Specific Membrane Antigen. Clin Cancer Res 12(8):2591-2596 (2006).
Maeda et al. Vascular permeability enhancement in solid tumor: various factors, mechanisms involved and its implications. International Immunopharmacology 3:319-328 (2003).
Maitz et al. Bio-responsive polymer hydrogels homeostatically regulate blood coagulation. Nat Commun. 4:2168 (2013).
Marcy et al. Human fibroblast stromelysin catalytic domain: expression, purification, and characterization of a C-terminally truncated form. Biochemistry 30:6476-6483 (1991).
Marion et al. Improved solvent suppression in one- and two-dimensional NMR spectra by convolution of time-domain data. J. Magn. Reson. 84:425-430 (1989).
Miller et al. Nanomedicine in chemoradiation. Ther Deliv 4:239-250 (2013).
Mitchell et al. Polyarginine enters cells more efficiently than other polycationic homopolymers. J. Peptide Res. 56:318-325 (2000).
Moding et al. Strategies for optimizing the response of cancer and normal tissues to radiation. Nat Rev Drug Discov 12:526-542 (2013).
Mullard. Maturing antibody-drug conjugate pipeline hits 30. Nat Rev Drug Discov 12:329-332 (2013).
Nguyen et al. Fluorescence-guided surgery with live molecular navigation—a new cutting edge. Nat Rev Cancer 13:653-662 (2013).
Nguyen et al. Surgery with molecular fluorescence imaging using activatable cell-penetrating peptides decreases residual cancer and improves survival. PNAS 107(9):4317-4322 (2010).
Ntziachristos et al. Fluorescence molecular tomography resolves protease activity in vivo. Nat. Med. 8:757-760 (2002).
Olafsen et al. Characterization of engineered anti-p185HER-2 (scFv-CH3)2 antibody fragments (minibodies) for tumor targeting. Protein Eng. Des. Sel. 17:315-323 (2004).
Olson. Disseratiion entitled Activatable cell penetrating peptides for Imaging Protease Activity In Vivo. http:\\escholarship.org/us/item/3sc4h3n7#page (170 pgs) (2008).

(56) References Cited

OTHER PUBLICATIONS

Olson et al. Activatable cell penetrating peptides linked to nanoparticles as dual probes for in vivo fluorescence and MR imaging of proteases. PNAS 107(9):4311-4316 (2010).
Olson et al. In vivo characterization of activatable cell penetrating peptides for targeting protease activity in cancer. Integr Biol (Camb) 1(5-6):382-393 (2009).
Olson et al. In vivo fluorescence imaging of atherosclerotic plaques with activatable cell-penetrating peptides thrombin activity. Integr Biol 4:595-605 (2012).
Passarella et al. Targeted Nanoparticles That Deliver a Sustained, Specific Release of Paclitaxel to Irradiated Tumors. Cancer Res 70(11):4550-4559 (2010).
PCT/US2010/042184 International Search Report dated Apr. 26, 2011.
PCT/US2010/042188 International Search Report dated Mar. 31, 2011.
PCT/US2012/048732 International Search Report and Written Opinion dated Apr. 30, 2013.
PCT/US2014/013942 International Preliminary Report on Patentability dated Aug. 13, 2015.
PCT/US2014/013942 International Search Report and Written Opinion dated May 28, 2014.
PCT/US2014/035043 International Preliminary Report on Patentability dated Nov. 5, 2015.
PCT/US2014/035043 International Search Report and Written Opinion dated Aug. 26, 2014.
Piotto et al. Gradient-tailored excitation for single-quantum NMR spectroscopy of aqueous solutions. J. Biomol. NMR 2:661-665 (1992).
Polyakov et al. Novel Tat-peptide chelates for direct transduction of technetium-99m and rhenium into human cells for imaging and radiotherapy. Bioconjugate Chem. 11:762-771 (2000).
Potocky et al. Cytoplasmic and nuclear delivery of a TAT-derived peptide and a beta-peptide after endocytic uptake into HeLa cells. J. Biol. Chem. 278:50188-50194 (2003).
Pretz et al. Chemoradiation therapy: localized esophageal, gastric, and pancreatic cancer. Surg Oncol Clin N Am 22:511-524 (2013).
Proimmune, think peptides ® the source for all peptides for your research, (pp. 1-15) (2012).
Prolmmune. Think Peptides: the source for all peptides for your research. pp. 1-15 (2012).
Raleigh et al. Molecular targets and mechanisms of radiosensitization using DNA damage response pathways. Future Oncol 9:219-223 (2013).
Ratnikov et al. Gelatin zymography and substrate cleavage assays of matrix metalloproteinase-2 in breast carcinoma cells overexpressing membrane type-1 matrix metalloproteinase. Lab. Invest. 82:1583-1590 (2002).
Razgulin et al. Strategies for in vivo imaging of enzyme activity: an overview and recent advances. Chem. Soc. Rev. 40:4186-4216 (2011).
Richard et al. Cell-penetrating peptides. A reevaluation of the mechanism of cellular uptake. J. Biol. Chem. 278:585-590 (2003).
Rieken et al. Targeting αV133 and αV135 inhibits photon-induced hypermigration of malignant glioma cells. Radiat Oncol 6(132):1-7 (2011).
Rothbard et al. Arginine-Rich Molecular Transporters for Drug Delivery: Role of Backbone Spacing in Cellular Uptake. J. Med. Chem. 45:3612-3618 (2002).
Rothbard et al. Conjugation of arginine oligomers to cyclosporin a facilitates topical delivery and inhibition of inflammation. Nature Medicine 6(11):1253-1257 (2000).
Ryppa et al. In Vitro and in vivo Evaluation of Doxorubicin Conjugates with the Divalent Peptide E-[c(RGDfK)2] that Targets Integrin αvβ3. Bioconjugate Chemistry 19:1414-1422 (2008).
Savariar et al. Fluorescence resonance energy transfer accelerates and amplifies tumor:background contrast from activatable cell penetrating peptides. Poster T209. World Molecular Imaging Congress, Sep. 7-10, San Diego (2011) (1 pg.).
Savariar et al. Real-time In Vivo Molecular Detection of Primary Tumors and Metastases with Ratiometric Activatable Cell-Penetrating Peptides. Cancer Res 73(2):855-864 (2013).
Scherer et al. Optical imaging of matrix metalloproteinase-7 activity in vivo using a proteolytic nanobeacon. Mol Imaging 7(3):118-131 (2008).
Sievers et al. Antibody-drug conjugates in cancer therapy. Annu Rev Med 64:15-29 (2013).
Sounni et al. Membrane type-1 matrix metalloproteinase and TIMP-2 in tumor angiogenesis. Matrix Biol. 22:55-61 (2003).
Speake et al. Radiation induced MMP expression from rectal cancer is short lived but contributes to in vitro invasion. Eur J Surg Oncol 31:869-874 (2005).
Sperling et al. Thrombin-responsive hydrogels with varied cleavage kinetics. Society for Biomaterials. Abstract # 208 (1 pg.) (2013).
Spinale. Matrix metalloproteinases: regulation and dysregulation in the failing heart. Circ. Res. 90:520-530 (2002).
Stary et al. A Definition of Advanced Types of Atherosclerotic Lesions and a Histological Classification of Atherosclerosis: A Report From the Committee on Vascular Lesions of the Council on Atheriosclerosis. American Heart Association, Circulation 92:1355-1374 (1995).
Stone et al. A Prospective Natural-History Study of Coronary Atherosclerosis. The New England Journal of Medicine 364(3):226-236 (2011).
Stricklin et al. Human skin fibroblast procollagenase: mechanisms of activation by organomercurials and trypsin. Biochemistry 22:61-68 (1983).
Sundaresan et al. 1241-labeled engineered anti-CEA minibodies and diabodies allow high-contrast, antigen-specific small-animal PET imaging of xenografts in athymic mice. J. Nucl. Med. 44:1962-1969 (2003).
Talvensaari-Mattila et al. Matrix metalloproteinase-2 (MMP-2) is associated with survival in breast carcinoma. Br. J. Cancer 89:1270-1275 (2003).
Thoren et al. Uptake of analogs of penetratin, Tat(48-60) and oligoarginine in live cells. Biochem. Biophys. Res. Commun. 307:100-107 (2003).
Tishler et al. Taxol: a novel radiation sensitizer. Int J Radiat Oncol Biol Phys 122:613-617 (1992).
Torchilin et al. Peptide and protein drug delivery to and into tumors: challenges and solutions. Drug Discovery Today 8:259-266 (2003).
Torchilin et al. TAT-liposomes: a novel intracellular drug carrier. Curr. Protein Pept. Sci. 4:133-140 (2003).
Tseng et al. Development of an Orthotopic Model of Invasive Pancreatic Cancer in an Immunocompetent Murine Host. Clinical Cancer Research 16(14):3684-3695 (2010).
Tsien et al. Practical design criteria for a dynamic ratio imaging system. Cell Calcium 11:93-109 (1990).
Tsien. Indicators Based on Fluorescence Resonance Energy Transfer, Chapter 74 in Imaging in Neuroscience and Development, Cold Spring Harbor Laboratory Press, Cold Spring Harbor pp. 549-556 (2005).
Tung et al. A Novel Near-Infrared Fluorescence Sensor for Detection of Thrombin Activation in Blood Chembiochem 3:207-211 (2002).
Tung et al. Arginine containing peptides as delivery vectors. Advanced Drug Delivery Reviews 55:281-294 (2003).
Ullrich et al. Contraluminal para-aminohippurate (PAH) transport in the proximal tubule of the rat kidney. Pflugers Arch. 415:342-350 (1989).
U.S. Appl. No. 10/699,562 Office Action dated Jun. 14, 2007.
U.S. Appl. No. 10/699,562 Office Action dated Nov. 30, 2006.
U.S. Appl. No. 10/699,562 Office Action dated Nov. 30, 2007.
U.S. Appl. No. 11/133,804 Office Action dated Aug. 18, 2010.
U.S. Appl. No. 11/133,804 Office Action dated Mar. 29, 2010.
U.S. Appl. No. 11/437,095 Office Action dated Apr. 21, 2011.
U.S. Appl. No. 11/437,095 Office Action dated Apr. 8, 2010.
U.S. Appl. No. 11/437,095 Office Action dated Dec. 2, 2013.
U.S. Appl. No. 11/437,095 Office Action dated Jun. 26, 2014.
U.S. Appl. No. 13/155,168 Office Action dated Jun. 6, 2014.
U.S. Appl. No. 13/155,168 Office Action dated Nov. 17, 2014.
U.S. Appl. No. 13/384,581 Office Action dated Dec. 9, 2016.

(56) References Cited

OTHER PUBLICATIONS

U.S. Appl. No. 13/384,581 Office Action dated Jul. 14, 2015.
U.S. Appl. No. 13/384,581 Office Action dated Mar. 15, 2016.
U.S. Appl. No. 13/384,581 Office Action dated Nov. 26, 2014.
U.S. Appl. No. 13/384,591 Office Action dated Jul. 14, 2015.
U.S. Appl. No. 13/384,591 Office Action dated Jun. 24, 2016.
U.S. Appl. No. 13/384,591 Office Action dated Mar. 1, 2016.
U.S. Appl. No. 13/384,591 Office Action dated Nov. 28, 2014.
U.S. Appl. No. 13/566,913 Office Action dated Feb. 24, 2015.
U.S. Appl. No. 13/566,913 Office Action dated Jan. 29, 2016.
U.S. Appl. No. 13/566,913 Office Action dated Jun. 30, 2015.
U.S. Appl. No. 13/566,913 Office Action dated Sep. 12, 2016.
U.S. Appl. No. 14/235,522 Office Action dated Sep. 8, 2015.
U.S. Appl. No. 14/753,975 Office Action dated Mar. 9, 2018.
U.S. Appl. No. 14/753,975 Office Action dated Nov. 15, 2017.
U.S. Appl. No. 14/764,681 Office Action dated Apr. 27, 2017.
U.S. Appl. No. 14/786,402 Office Action dated Mar. 29, 2018.
U.S. Appl. No. 15/006,832 First Action Interview dated Mar. 21, 2016.
U.S. Appl. No. 15/685,942 Office Action dated Mar. 30, 2018.
Van Berkel et al. Fluorogenic Peptide-Based Substrates for Monitoring Thrombin Activity. ChemMedChem 7:606-617 (2012).
Van Dam et al. Intraoperative tumor-specific fluorescence imaging in ovarian cancer by folate receptor-αtargeting: first in-human results. Nature Medicine 17:1315-1319 (2011).
Van Duijnhoven et al. Tumor Targeting of MMP-2/9 Activatable Cell-Penetrating Imaging Probes is Caused by Tumor-independent Activation. J Nucl Med 52:279-286 (2011).
Van Vlerken et al. Poly(ethylene glycol)-modified nanocarriers for tumor-targeted and intracellular delivery. Pharma Res 24(8):1405-1414 (2007).
Vartak et al. In vitro evaluation of functional interaction of integrin αvβ3 and matrix metalloprotease-2. Mol. Pharmaceutics 6(6):1856-1867 (2009).
Visse et al. Matrix metalloproteinases and tissue inhibitors of metalloproteinases: structure, function, and biochemistry. Circ. Res. 92:827-839 (2003).
Vives et al. A truncated HIV-1 Tat protein basic domain rapidly translocates through the plasma membrane and accumulates in the cell nucleus. J. Biol. Chem. 272:16010-16017 (1997).
Von Lampe et al. Differential expression of matrix metalloproteinases and their tissue inhibitors in colon mucosa of patients with inflammatory bowel disease. Gut 47:63-73 (2000).
Wadia et al. Protein transduction technology. Curr. Opinion Biotech. 13:52-56 (2002).
Wadia et al. Transducible TAT-HA fusogenic peptide enhances escape of TAT-fusion proteins after lipid raft macropinocytosis. Nat. Med. 10:310-315 (2004).
Wang et al. Efficacy and safety of dendrimer nanoparticles with coexpression of tumor necrosis factor-α and herpes simplex virus thymidine kinase in gene radiotherapy of the human uveal melanoma OCM-1 cell line. Int J NanoMedicine 8:3805-3816 (2013).
Wang et al. Visualizing the mechanical activation of Src. Nature 434:1040-1045 (Apr. 21, 2005).
Weissleder et al. Molecular imaging. Radiology 219:316-333 (2001).
Wender et al. The design, synthesis, and evaluation of molecules that enable or enhance cellular uptake: Peptoid molecular transporters. PNAS 97(24):13003-13008 (2000).
Werner et al. Preclinical evaluation of Genexol-PM, a nanoparticle formulation of paclitaxel, as a novel radiosensitizer for the treatment of non-small cell lung cancer. Int J Radiat Oncol Biol Phys 86:463-468 (2013).
Whitney et al. Parallel in Vivo and in Vitro Selection Using Phage Display Identifies Protease-dependent Tumor-targeting Peptides. The Journal of Biological Chemistry 285(29):22532-22541 (2010).
Winnard et al. Real time non-invasive imaging of receptor-ligand interactions in vivo. J. Cell Biochem. 90:454-463 (2003).
Wright et al. Guanidinium rich peptide transporters and drug delivery. Curr. Protein Pept. Sci. 4:105-124 (2003).
Xu et al. RGD-conjugated gold nanorods induce Radiosensitization in melanoma cancer cells by down regulating αvβ3 expression. Intl J of Nanomedicine 7:915-924 (2012).
Yamaoka et al. Distribution and tissue uptake of poly(ethylene glycol) with different molecular weights after intravenous administration to mice. J. Pharm. Sci. 83:601-606 (1994).
Yuan et al. Challenges associated with the targeted delivery of gelonin to claudin-expressing cancer cells with the use of activatable cell penetrating peptides to enhance potency. BMC 11(1):61 (2011).
Zhang et al. Preparation of functionally active cell-permeable peptides by single-step ligation of two peptide modules. PNAS 95:9184-9189 (1998).
Zhao et al. Differential conjugation of tat peptide to superparamagnetic nanoparticles and its effect on cellular uptake. Bioconjugate Chem. 13:840-844 (2002).
Zhu et al. Dual-Functional, Receptor-Targeted Fluorogenic Probe for in Vivo Imaging of Extracellular Protease Expressions. Bioconjugate Chemistry 22(6):1001-1005 (2011).
Znati et al. Effect of Radiation on Interstitual Fluid Pressure and Oxygenation in a Human Tumor Xenograft. Cancer Res 56:964-968 (1196).

\* cited by examiner pxint1, Cy-5ex, Cy5em pxint1, Cy-5ex, Cy7em k * (pxint1/Exp1)/(pxint2/Exp2)

SELECTIVE DELIVERY MOLECULES AND METHODS OF USE

CROSS REFERENCE

This application is a continuation of U.S. application Ser. No. 15/685,942, filed on Aug. 24, 2017, which is a continuation of U.S. application Ser. No. 14/764,681, filed Jul. 30, 2015, now issued as U.S. Pat. No. 9,782,498 on Oct. 10, 2017, which is the National Stage entry of International Application No. PCT/US2014/013942, filed Jan. 30, 2014, which claims the benefit of U.S. Provisional Application No. 61/758,680, filed Jan. 30, 2013; each of which are incorporated herein by reference in their entireties.

SEQUENCE LISTING

The instant application contains a Sequence Listing which has been submitted in ASCII format and is hereby incorporated by reference in its entirety. Said ASCII copy, created on Jan. 31, 2019, is named "39088710302_SL.txt" and is 7,993 bytes in size.

SUMMARY OF THE INVENTION

Disclosed herein, in certain embodiments, is a selective delivery molecule according to SDM-41. Disclosed herein, in certain embodiments, is a selective delivery molecule according to SDM-42. Disclosed herein, in certain embodiments, is a selective delivery molecule according to SDM-43. Disclosed herein, in certain embodiments, is a selective delivery molecule according to SDM-44. Disclosed herein, in certain embodiments, is a selective delivery molecule according to SDM-45. Disclosed herein, in certain embodiments, is a selective delivery molecule according to SDM-46. Disclosed herein, in certain embodiments, is a selective delivery molecule according to SDM-47. Disclosed herein, in certain embodiments, is a selective delivery molecule according to SDM-48. Disclosed herein, in certain embodiments, is a selective delivery molecule according to SDM-49. Disclosed herein, in certain embodiments, is a selective delivery molecule according to SDM-50. Disclosed herein, in certain embodiments, is a selective delivery molecule according to SDM-51. Disclosed herein, in certain embodiments, is a selective delivery molecule according to SDM-52. Disclosed herein, in certain embodiments, is a selective delivery molecule according to SDM-53. Disclosed herein, in certain embodiments, is a selective delivery molecule according to SDM-54. Disclosed herein, in certain embodiments, is a selective delivery molecule according to SDM-55. Disclosed herein, in certain embodiments, is a selective delivery molecule according to SDM-56. Disclosed herein, in certain embodiments, is a selective delivery molecule according to SDM-57. Disclosed herein, in certain embodiments, is a selective delivery molecule according to SDM-58. Disclosed herein, in certain embodiments, is a selective delivery molecule according to SDM-59. Disclosed herein, in certain embodiments, is a selective delivery molecule according to SDM-60. Disclosed herein, in certain embodiments, is a selective delivery molecule according to SDM-61. Disclosed herein, in certain embodiments, is a selective delivery molecule according to SDM-62. Disclosed herein, in certain embodiments, is a selective delivery molecule according to SDM-63. Disclosed herein, in certain embodiments, is a selective delivery molecule according to SDM-64. Disclosed herein, in certain embodiments, is a selective delivery molecule according to SDM-65.

Disclosed herein, in certain embodiments, are tissue samples comprising a molecule selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the tissue sample is a pathology slide or section. In some embodiments, the tissue sample is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue.

Disclosed herein, in certain embodiments, are methods of delivering a pair of imaging agents to a tissue of interest, comprising contacting the tissue of interest with a molecule selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the tissue of interest is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue or cancerous lymph node tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue.

Disclosed herein, in certain embodiments, are methods of visualizing a tissue of interest in an individual in need thereof, comprising: (a) administering to the individual a molecule selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65; and (b) visualizing at least one of the imaging agents. In some embodiments, the molecule is SDM-41. In some embodiments, the tissue is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous cell or tissue is breast cancer tissue. In some embodiments, the cancerous cell or tissue is colorectal cancer tissue. In some embodiments, the cancerous cell or tissue is cancerous lymph node tissue. In some embodiments, the cancerous cell or tissue is squamous cell carcinoma tissue. In some embodiments, the cancerous cell or tissue is skin cancer tissue. In some embodiments, the method further comprises surgically removing the tissue of interest from the individual. In some embodiments, the surgical margin surrounding the tissue of interest is decreased. In some embodiments, the method further comprises preparing a tissue sample from the removed cell or tissue of interest. In some embodiments, the method further comprises staging the cancerous tissue. In some embodiments, the method further comprises visualizing Forsters/fluorescence resonance energy transfer between the fluorescent moiety and a fluorescence-quenching moiety of the molecule.

Disclosed herein, in certain embodiments, are tissue samples comprising a molecule of Formula I:

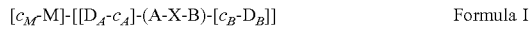

$$[c_M\text{-}M]\text{-}[[D_A\text{-}c_A]\text{-}(A\text{-}X\text{-}B)\text{-}[c_B\text{-}D_B]] \qquad \text{Formula I}$$

wherein,
   X is a cleavable linker;
   A is a peptide with a sequence comprising 5 to 9 acidic amino acids;
   B is a peptide with a sequence comprising 7 to 9 basic amino acids;
   $c_A$, $c_B$, and $c_M$ are independently 0-1 amino acid;
   M is a polyethylene glycol (PEG) polymer; and
   $D_A$ and $D_B$ are each independently an imaging agent;
   wherein $[c_M\text{-}M]$ is bound at any position on or between A, X, and B, $[D_A\text{-}c_A]$ is bound to any amino acid on A or X, and $[c_B\text{-}D_B]$ is bound to any amino acid on B; and
   wherein the molecule of Formula I is selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65.

In some embodiments, the tissue sample is a pathology slide or section. In some embodiments, the tissue sample is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue.

Disclosed herein, in certain embodiments, are methods of delivering a pair of imaging agents to a tissue of interest, comprising contacting the tissue of interest with a molecule of Formula I:

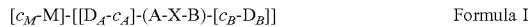

$$[c_M\text{-}M]\text{-}[[D_A\text{-}c_A]\text{-}(A\text{-}X\text{-}B)\text{-}[c_B\text{-}D_B]] \qquad \text{Formula I}$$

wherein,
   X is a cleavable linker;
   A is a peptide with a sequence comprising 5 to 9 acidic amino acids;
   B is a peptide with a sequence comprising 7 to 9 basic amino acids;
   $c_A$, $c_B$, and $c_M$ are independently 0-1 amino acid;
   M is a polyethylene glycol (PEG) polymer; and
   $D_A$ and $D_B$ are each independently an imaging agent;
   wherein $[c_M\text{-}M]$ is bound at any position on or between A, X, and B, $[D_A\text{-}c_A]$ is bound to any amino acid on A or X, and $[c_B\text{-}D_B]$ is bound to any amino acid on B; and
   wherein the molecule of Formula I is selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65.

In some embodiments, the tissue of interest is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue.

Disclosed herein, in certain embodiments, are methods of visualizing a tissue of interest in an individual in need thereof, comprising: (a) administering to the individual a molecule of Formula I that localizes to the tissue of interest in the individual,

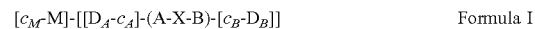

$$[c_M\text{-}M]\text{-}[[D_A\text{-}c_A]\text{-}(A\text{-}X\text{-}B)\text{-}[c_B\text{-}D_B]] \qquad \text{Formula I}$$

wherein,
   X is a cleavable linker;
   A is a peptide with a sequence comprising 5 to 9 acidic amino acids;
   B is a peptide with a sequence comprising 7 to 9 basic amino acids;
   $c_A$, $c_B$, and $C_M$ are independently 0-1 amino acid;
   M is a polyethylene glycol (PEG) polymer; and
   $D_A$ and $D_B$ are each independently an imaging agent; and
   wherein $[c_M\text{-}M]$ is bound at any position on or between A, X, and B, $[D_A\text{-}c_A]$ is bound to any amino acid on A or X, and $[c_B\text{-}D_B]$ is bound to any amino acid on B;
   wherein the molecule of Formula I is selected from: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65; and
   (b) visualizing at least one of the imaging agents;

In some embodiments, the tissue of interest is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue. In some embodiments, the methods further comprise surgically removing the tissue of interest from the individual. In some embodiments, the surgical margin surrounding the tissue of interest is decreased. In some embodiments, the methods further comprise preparing a tissue sample from the removed tissue of interest. In some embodiments, the methods further comprise staging the cancerous tissue.

Disclosed herein, in certain embodiments, is a peptide according to Peptide P-16.

DETAILED DESCRIPTION OF THE INVENTION

Figure 1:
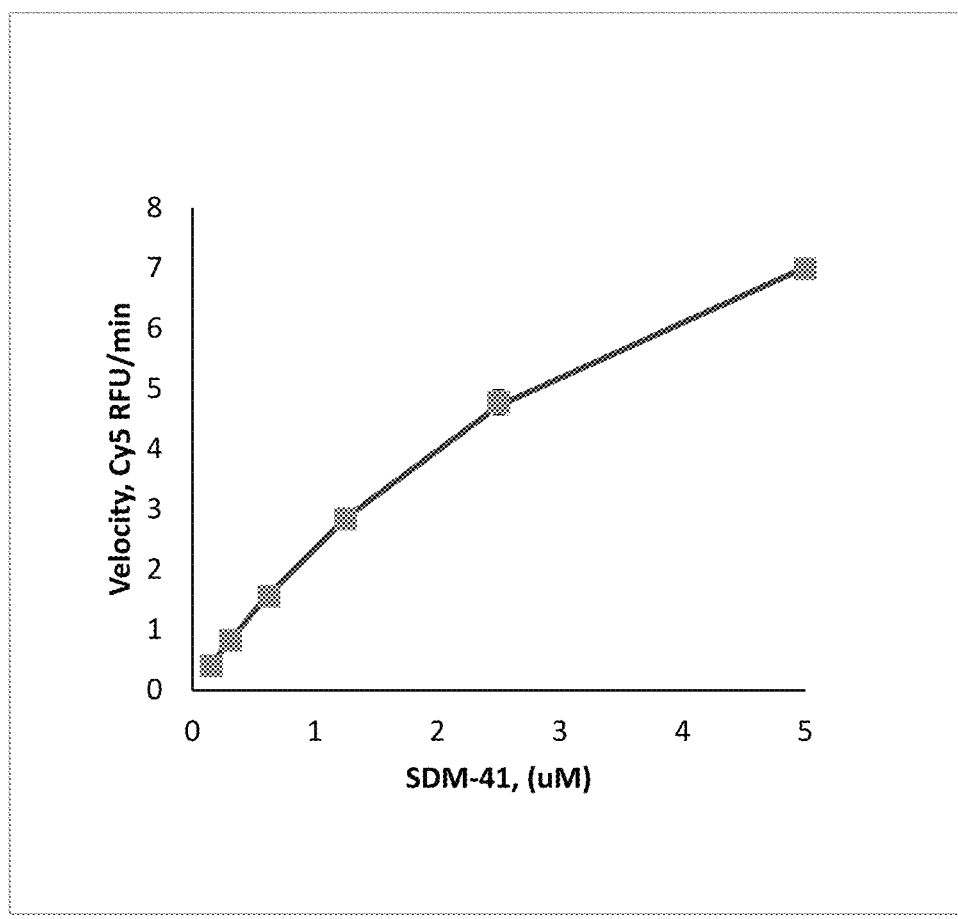
FIG. 1 shows that the velocity of MMP-7 cleavage of SDM-41 increases with increasing SDM-41 concentration, consistent with Michaelis-Menten kinetics (Example 2a).

Selective delivery molecules (SDMs) allow the targeted delivery of therapeutic agents and/or imaging agents to specific cells and/or tissues. In some embodiments, selective delivery molecules comprise (a) a molecular transport or tissue retention sequence (portion B), (b) cargo moieties (portion $D_A$ and $D_B$) bound to portion A, B, or X, (c) X a linker, and (d) a macromolecular carrier and (e) an acidic sequence (portion A) which is effective to inhibit or prevent the uptake into cells or tissue retention. In some embodiments, cleavage of X linker, which allows the separation of portion A from portion B, is effective to allow the uptake or retention of portion B and the attached cargo into cells and tissue. However, selective delivery molecules may be subject to rapid pharmacokinetic clearance with short plasma half-life, broad distribution, and slow wash out from multiple non-target tissues with non-specific uptake. Thus, there is a need for a selective delivery molecule with increased in vivo circulation, accumulation in target tissue relative to non-target tissue, modulated extravasation selectivity, and modulated bio-distribution. For imaging agents, there is a need for increased contrast in target tissue relative to background tissue.

Certain Definitions

As used herein, the following terms have the meanings ascribed to them unless specified otherwise.

As used herein, the term "targeting molecule" refers to any agent (e.g., peptide, protein, nucleic acid polymer, aptamer, or small molecule) that associates with (e.g., binds to) a target of interest. The target of interest may be a tissue, a cell, a cellular structure (e.g., an organelle), a protein, a peptide, a polysaccharide, or a nucleic acid polymer. In some embodiments, the targeting molecule is any agent that associates with (e.g., binds to) one or more cancer cells of a subject.

The term PEG means polyethylene glycol polymer. In some embodiments, the PEG is a polydisperse. In some embodiments, the PEG is discreet.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are either D amino acids of L amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

As used herein, the term "label" refers to a molecule that facilitates the visualization and/or detection of a targeting molecule disclosed herein. In some embodiments, the label is a fluorescent moiety.

The phrase "specifically binds" when referring to the interaction between a targeting molecule disclosed herein and a target (e.g., purified protein, cancer cells or cancerous tissue, tumor, or metastatic lesion, metastases, or lymph node or metastatic lymph node), refers to the formation of a high affinity bond between the targeting molecule and the target. Further, the term means that the targeting molecule has low affinity for non-targets.

"Selective binding," "selectivity," and the like refers to the preference of an agent to interact with one molecule as compared to another. Preferably, interactions between a targeting molecule disclosed herein and a target are both specific and selective. Note that in some embodiments an agent is designed to "specifically bind" and "selectively bind" two distinct, yet similar targets without binding to other undesirable targets The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any method that may be used to investigate, manipulate, change, or cause an effect in a tissue by a physical intervention. These methods include, but are not limited to open surgery, endoscopic surgery, laparoscopic surgery, minimally invasive surgery, robotic surgery, and any procedures that may affect a cancerous tissue such as tumor resection, cancer tissue ablation, cancer staging, cancer diagnosis, lymph node staging, sentinel lymph node detection, or cancer treatment.

The term "guided surgery" as used herein, refers to any surgical procedure where the surgeon employs an imaging agent to guide the surgery.

The term "cancer" as used herein, refers to any disease involving uncontrolled growth or proliferation of cells in the human body. Cancers may further be characterized by the ability of cells to migrate from the original site and spread to distant sites (i.e., metastasize). Cancers may be sarcomas, carcinomas, lymphomas, leukemias, blastomas, or germ cell tumors. Cancers may occur in a variety of tissues including but not limited to lung, breast, ovaries, colon, esophagus, rectum, bone, prostate, brain, pancreas, bladder, kidney, liver, blood cells, lymph nodes, thyroid, skin, and stomach.

Selective Delivery Molecules

Disclosed herein, in certain embodiments, is a selective delivery molecule according to SDM-41. Disclosed herein, in certain embodiments, is a selective delivery molecule according to SDM-42. Disclosed herein, in certain embodiments, is a selective delivery molecule according to SDM-43. Disclosed herein, in certain embodiments, is a selective delivery molecule according to SDM-44. Disclosed herein, in certain embodiments, is a selective delivery molecule according to SDM-45. Disclosed herein, in certain embodiments, is a selective delivery molecule according to SDM-46. Disclosed herein, in certain embodiments, is a selective delivery molecule according to SDM-47. Disclosed herein, in certain embodiments, is a selective delivery molecule according to SDM-48. Disclosed herein, in certain embodiments, is a selective delivery molecule according to SDM-49. Disclosed herein, in certain embodiments, is a selective delivery molecule according to SDM-50. Disclosed herein, in certain embodiments, is a selective delivery molecule according to SDM-51. Disclosed herein, in certain embodiments, is a selective delivery molecule according to SDM-52. Disclosed herein, in certain embodiments, is a selective delivery molecule according to SDM-53. Disclosed herein, in certain embodiments, is a selective delivery molecule according to SDM-54. Disclosed herein, in certain embodiments, is a selective delivery molecule according to SDM-55. Disclosed herein, in certain embodiments, is a selective delivery molecule according to SDM-56. Disclosed herein, in certain embodiments, is a selective delivery molecule according to SDM-57. Disclosed herein, in certain embodiments, is a selective delivery molecule according to SDM-58. Disclosed herein, in certain embodiments, is a selective delivery molecule according to SDM-59. Disclosed herein, in certain embodiments, is a selective delivery molecule according to SDM-60. Disclosed herein, in certain embodiments, is a selective delivery molecule according to SDM-61. Disclosed herein, in certain embodiments, is a selective delivery molecule according to SDM-62. Disclosed herein, in certain embodiments, is a selective delivery molecule according to SDM-63. Disclosed herein, in certain embodiments, is a selective delivery molecule according to SDM-64. Disclosed herein, in certain embodiments, is a selective delivery molecule according to SDM-65.

Disclosed herein, in certain embodiments, are selective delivery molecule of Formula I, having the structure:

$$[c_M\text{-M}]\text{-}[[D_A\text{-}c_A]\text{-}(A\text{-}X\text{-}B)\text{-}[c_B\text{-}D_B]] \qquad \text{Formula I}$$

wherein,

X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acid;

M is a macromolecule carrier; and $D_A$ and $D_B$ are each independently selected from an imaging agent and a therapeutic; and wherein $[c_M\text{-M}]$ is bound at any position on or between A, X, and B, $[D_A\text{-}c_A]$ is bound to any amino acid on A or X, and $[c_B\text{-}D_B]$ is bound to any amino acid on B. In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NOS: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ ID NOS: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a free amino group (e.g., a N-terminal amine group), and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO:1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence RLQLKL (SEQ ID NO:11). In some embodiments, X comprises the amino acid sequence RLQLK(Ac) (SEQ ID NO: 12). In some embodiments, M is selected from a protein, a natural polymer, a synthetic polymer, or a dendrimer. In some embodiments, M is selected from dextran, PEG polymers, albumin, or a combination thereof. In some embodiments, M is PEG polymers. In some embodiments, M is PEG polymers having an average molecular weight of approximately 0.5 KDa (PEG 0.5 KDa), 2 kDa (PEG 2 KDa), 5 kDa (PEG 5 KDa), 12 kDa (PEG 12 kDa), 20 kDa (PEG 20 kDa), 30 kDa (PEG 30 kDa), and 40 kDa (PEG 40 kDa). In some embodiments, $D_A$ and $D_B$ are a pair of donor and acceptor fluorescent moieties that are capable of undergoing Forsters/fluorescence resonance energy transfer with the other. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule of Formula I is SDM-41.

Disclosed herein, in certain embodiments, are selective delivery molecules of Formula I, having the structure:

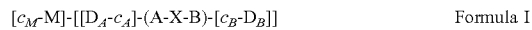

$$[c_M\text{-}M]\text{-}[[D_A\text{-}c_A]\text{-}(A\text{-}X\text{-}B)\text{-}[c_B\text{-}D_B]] \qquad \text{Formula I}$$

wherein,
X is a cleavable linker;
A is a peptide with a sequence comprising 5 to 9 acidic amino acids;
B is a peptide with a sequence comprising 7 to 9 basic amino acids;
$c_A$, $c_B$, and $c_M$ are independently 0-1 amino acid;
M is a polyethylene glycol (PEG) polymer; and
$D_A$ and $D_B$ are each independently an imaging agent; and
wherein $[c_M\text{-}M]$ is bound to at any position on A or X, [DA-cA] is bound to any amino acid on A or X, and $[c_B\text{-}D_B]$ is bound to any amino acid on B.

In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NOS: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ ID NOS: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO:9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence PPRSFL (SEQ ID NO: 10). In some embodiments, X comprises the amino acid sequence RLQLKL (SEQ ID NO: 11). In some embodiments, X comprises the amino acid sequence RLQLK(Ac) (SEQ ID NO: 12). In some embodiments, $D_A$ and $D_B$ are a pair of acceptor and donor fluorescent moieties that are capable of undergoing Forsters/fluorescence resonance energy transfer with the other. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule of Formula I is SDM-41.

Portion A

In some embodiments, A is a peptide with a sequence comprising 2 to 20 acidic amino acids. In some embodiments, peptide portion A comprises between about 2 to about 20 acidic amino acids. In some embodiments, peptide portion A comprises between about 5 to about 20 acidic amino acids. In some embodiments, A has a sequence comprising 5 to 9 acidic amino acids. In some embodiments, A has a sequence comprising 5 to 8 acidic amino acids. In some embodiments, A has a sequence comprising 5 to 7 acidic amino acids. In some embodiments, A has a sequence comprising 5 acidic amino acids. In some embodiments, A has a sequence comprising 6 acidic amino acids. In some embodiments, A has a sequence comprising 7 acidic amino acids. In some embodiments, A has a sequence comprising 8 acidic amino acids. In some embodiments, A has a sequence comprising 9 acidic amino acids.

In some embodiments, peptide portion A comprises between about 2 to about 20 consecutive acidic amino acids. In some embodiments, peptide portion A comprises between about 5 to about 20 consecutive acidic amino acids. In some embodiments, A has a sequence comprising 5 to 9 consecutive acidic amino acids. In some embodiments, A has a sequence comprising 5 to 8 consecutive acidic amino acids. In some embodiments, A has a sequence comprising 5 to 7 consecutive acidic amino acids. In some embodiments, A has a sequence comprising 5 consecutive acidic amino acids. In some embodiments, A has a sequence comprising 6 consecutive acidic amino acids. In some embodiments, A has a sequence comprising 7 consecutive acidic amino acids. In some embodiments, A has a sequence comprising 8 consecutive acidic amino acids. In some embodiments, A has a sequence comprising 9 consecutive acidic amino acids.

In some embodiments, peptide portion A comprises between about 2 to about 20 acidic amino acids selected from, aspartates and glutamates. In some embodiments, peptide portion A comprises between about 5 to about 20 acidic amino acids selected from, aspartates and glutamates. In some embodiments, A has a sequence comprising 5 to 9 acidic amino acids selected from, aspartates and glutamates. In some embodiments, A has a sequence comprising 5 to 8 acidic amino acids selected from, aspartates and glutamates. In some embodiments, A has a sequence comprising 5 to 7 acidic amino acids selected from, aspartates and glutamates. In some embodiments, A has a sequence comprising 5 acidic amino acids selected from, aspartates and glutamates. In some embodiments, A has a sequence comprising 6 acidic amino acids selected from, aspartates and glutamates. In some embodiments, A has a sequence comprising 7 acidic amino acids selected from, aspartates and glutamates. In some embodiments, A has a sequence comprising 8 acidic amino acids selected from, aspartates and glutamates. In some embodiments, A has a sequence comprising 9 acidic amino acids selected from, aspartates and glutamates.

In some embodiments, peptide portion A comprises between about 2 to about 20 consecutive acidic amino acids selected from, aspartates and glutamates. In some embodiments, peptide portion A comprises between about 5 to about 20 consecutive acidic amino acids selected from, aspartates and glutamates. In some embodiments, A has a sequence comprising 5 to 9 consecutive acidic amino acids selected from, aspartates and glutamates. In some embodiments, A has a sequence comprising 5 to 8 consecutive acidic amino acids selected from, aspartates and glutamates. In some embodiments, A has a sequence comprising 5 to 7 consecutive acidic amino acids selected from, aspartates and glutamates. In some embodiments, A has a sequence comprising 5 consecutive acidic amino acids selected from, aspartates and glutamates. In some embodiments, A has a sequence comprising 6 consecutive acidic amino acids selected from, aspartates and glutamates. In some embodiments, A has a sequence comprising 7 consecutive acidic amino acids selected from, aspartates and glutamates. In some embodiments, A has a sequence comprising 8 consecutive acidic amino acids selected from, aspartates and glutamates. In some embodiments, A has a sequence comprising 9 consecutive acidic amino acids selected from, aspartates and glutamates.

In some embodiments, peptide portion A comprises between about 2 to about 20 glutamates. In some embodiments, peptide portion A comprises between about 5 to about 20 glutamates. In some embodiments, A has a sequence comprising 5 to 9 glutamates. In some embodiments, A has a sequence comprising 5 to 8 glutamates. In some embodiments, A has a sequence comprising 5 to 7 glutamates. In some embodiments, A has a sequence comprising 5 glutamates. In some embodiments, A has a sequence comprising 6 glutamates. In some embodiments, A has a sequence comprising 7 glutamates. In some embodiments, A has a sequence comprising 8 glutamates. In some embodiments, A has a sequence comprising 9 glutamates.

In some embodiments, peptide portion A comprises between about 2 to about 20 consecutive glutamates. In some embodiments, peptide portion A comprises between about 5 to about 20 consecutive glutamates. In some embodiments, A has a sequence comprising 5 to 9 consecutive glutamates (SEQ ID NO: 13). In some embodiments, A has a sequence comprising 5 to 8 consecutive glutamates (SEQ ID NO: 14). In some embodiments, A has a sequence comprising 5 to 7 consecutive glutamates (SEQ ID NO: 15).

In some embodiments, A has a sequence comprising 5 consecutive glutamates (SEQ ID NO: 4). In some embodiments, A has a sequence comprising 6 consecutive glutamates (SEQ ID NO: 16). In some embodiments, A has a sequence comprising 7 consecutive glutamates (SEQ ID NO: 17). In some embodiments, A has a sequence comprising 8 consecutive glutamates (SEQ ID NO: 18). In some embodiments, A has a sequence comprising 9 consecutive glutamates (SEQ ID NO: 5).

In some embodiments, portion A comprises 5 consecutive glutamates (i.e., EEEEE (SEQ ID NO: 4) or eeeee). In some embodiments, portion A comprises 9 consecutive glutamates (i.e., EEEEEEEEE (SEQ ID NO: 5) or eeeeeeeee).

An acidic portion A may include amino acids that are not acidic. Acidic portion A may comprise other moieties, such as negatively charged moieties. In embodiments of a selective delivery molecule disclosed herein, an acidic portion A may be a negatively charged portion, preferably having about 2 to about 20 negative charges at physiological pH that does not include an amino acid.

In some embodiments, the amount of negative charge in portion A is approximately the same as the amount of positive charge in portion B. In some embodiments, the amount of negative charge in portion A is not the same as the amount of positive charge in portion B. In some embodiments, improved tissue uptake is seen in a selective delivery molecule wherein the amount of negative charge in portion A is not the same as the amount of positive charge in portion B. In some embodiments, improved solubility is observed in a selective delivery molecule wherein the amount of negative charge in portion A is not the same as the amount of positive charge in portion B. In some embodiments, faster tissue uptake is seen in a selective delivery molecule wherein the amount of negative charge in portion A is not the same as the amount of positive charge in portion B. In some embodiments, greater tissue uptake is seen in a selective delivery molecule wherein the amount of negative charge in portion A is not the same as the amount of positive charge in portion B.

Portion A is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The Selective Delivery Molecules disclosed herein are effective where A is at the amino terminus or where A is at the carboxy terminus, i.e., either orientation of the peptide bonds is permissible.

Portion B

In some embodiments, B is a peptide with a sequence comprising 5 to 15 basic amino acids. In some embodiments, peptide portion B comprises between about 5 to about 20 basic amino acids. In some embodiments, peptide portion B comprises between about 5 to about 12 basic amino acids. In some embodiments, peptide portion B comprises between about 7 to about 9 basic amino acids. In some embodiments, peptide portion B comprises between about 7 to about 8 basic amino acids. In some embodiments, peptide portion B comprises 9 basic amino acids. In some embodiments, peptide portion B comprises 8 basic amino acids. In some embodiments, peptide portion B comprises 7 basic amino acids.

In some embodiments, peptide portion B comprises between about 5 to about 20 consecutive basic amino acids. In some embodiments, peptide portion B comprises between about 5 to about 12 consecutive basic amino acids. In some embodiments, peptide portion B comprises between about 7 to about 9 consecutive basic amino acids. In some embodiments, peptide portion B comprises between about 7 to about 8 consecutive basic amino acids. In some embodiments, peptide portion B comprises 9 consecutive basic amino acids. In some embodiments, peptide portion B comprises 8 consecutive basic amino acids. In some embodiments, peptide portion B comprises 7 consecutive basic amino acids.

In some embodiments, peptide portion B comprises between about 5 to about 20 basic amino acids selected from arginines, histidines, and lysines. In some embodiments, peptide portion B comprises between about 5 to about 12 basic amino acids selected from arginines, histidines, and lysines. In some embodiments, peptide portion B comprises between about 7 to about 9 basic amino acids selected from arginines, histidines, and lysines. In some embodiments, peptide portion B comprises between about 7 to about 8 basic amino acids selected from arginines, histidines, and lysines. In some embodiments, peptide portion B comprises 9 basic amino acids selected from arginines, histidines, and lysines. In some embodiments, peptide portion B comprises 8 basic amino acids selected from arginines, histidines, and lysines. In some embodiments, peptide portion B comprises 7 basic amino acids selected from arginines, histidines, and lysines.

In some embodiments, peptide portion B comprises between about 5 to about 20 consecutive basic amino acids selected from arginines, histidines, and lysines. In some embodiments, peptide portion B comprises between about 5 to about 12 consecutive basic amino acids selected from arginines, histidines, and lysines. In some embodiments, peptide portion B comprises between about 7 to about 9 consecutive basic amino acids selected from arginines, histidines, and lysines. In some embodiments, peptide portion B comprises between about 7 to about 8 consecutive basic amino acids selected from arginines, histidines, and lysines. In some embodiments, peptide portion B comprises 9 consecutive basic amino acids selected from arginines, histidines, and lysines. In some embodiments, peptide portion B comprises 8 consecutive basic amino acids selected from arginines, histidines, and lysines. In some embodiments, peptide portion B comprises 7 consecutive basic amino acids selected from arginines, histidines, and lysines.

In some embodiments, peptide portion B comprises between about 5 to about 20 arginines. In some embodiments, peptide portion B comprises between about 5 to about 12 arginines. In some embodiments, peptide portion B comprises between about 7 to about 9 arginines. In some embodiments, peptide portion B comprises between about 7 to about 8 arginines. In some embodiments, peptide portion B comprises 9 arginines. In some embodiments, peptide portion B comprises 8 arginines. In some embodiments, peptide portion B comprises 7 arginines.

In some embodiments, peptide portion B comprises between about 5 to about 20 consecutive arginines. In some embodiments, peptide portion B comprises between about 5 to about 12 consecutive arginines. In some embodiments, peptide portion B comprises between about 7 to about 9 consecutive arginines. In some embodiments, peptide portion B comprises between about 7 to about 8 consecutive arginines. In some embodiments, peptide portion B comprises 9 consecutive arginines (SEQ ID NO: 7). In some embodiments, peptide portion B comprises 8 consecutive arginines (SEQ ID NO: 6). In some embodiments, peptide portion B comprises 7 consecutive arginines (SEQ ID NO: 19).

A basic portion B may include amino acids that are not basic. Basic portion B may comprise other moieties, such as positively charged moieties. In embodiments, a basic portion B may be a positively charged portion, preferably having between about 5 and about 20 positive charges at physiological pH, that does not include an amino acid. In some embodiments, the amount of negative charge in portion A is approximately the same as the amount of positive charge in portion B. In some embodiments, the amount of negative charge in portion A is not the same as the amount of positive charge in portion B.

Portion B is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X is a peptide cleavable by a protease, it may be preferable to join the C-terminus of X to the N-terminus of B, so that the new amino terminus created by cleavage of X contributes an additional positive charge that adds to the positive charges already present in B.

Conjugation Group (c)

In some embodiments, the cargo (e.g., $D_A$ and $D_B$) and the macromolecule carriers (M) are attached indirectly to A-X-B.

In some embodiments, the cargo (e.g., $D_A$ and $D_B$) and the macromolecule carriers (M) are attached indirectly to A-X-B by a conjugation group ($c_A$, $c_B$, and $c_M$). In some embodiments, the cargo (e.g., $D_A$ and $D_B$) and the macromolecule carriers (M) are attached indirectly to A-X-B by a reactive conjugation group ($c_A$, $c_B$, and $c_M$). In some embodiments, the cargo (e.g., $D_A$ and $D_B$) and the macromolecule carriers (M) are attached indirectly to A-X-B by an orthogonally reactive conjugation group ($c_A$, $c_B$, and $c_M$). In some embodiments, $c_A$, $c_B$, and $c_M$ are independently an amino acid. In some embodiments, $c_A$, $c_B$, and $c_M$ are independently 0-10 amino acids. In some embodiments, $c_A$, $c_B$, and $c_M$ are independently 1 amino acid. In some embodiments, $c_A$, $c_B$, and $c_M$ are independently 2 amino acids. In some embodiments, $c_A$, $c_B$, and $c_M$ are independently 3 amino acids. In some embodiments, $c_A$, $c_B$, and $c_M$ are independently 4 amino acids. In some embodiments, $c_A$, $c_B$, and $c_M$ are independently 5 amino acids. In some embodiments, $c_A$, $c_B$, and $c_M$ are independently 6 amino acids. In some embodiments, $c_A$, $c_B$, and $c_M$ are independently 7 amino acids. In some embodiments, $c_A$, $c_B$, and $c_M$ are independently 8 amino acids. In some embodiments, $c_A$, $c_B$, and $c_M$ are independently 9 amino acids. In some embodiments, $c_A$, $c_B$, and $c_M$ are independently 10 amino acids.

In some embodiments, $c_A$, $c_B$, and $c_M$ are independently a derivatized amino acid. In some embodiments, multiple cargos (D) are attached to a derivatized amino acid conjugation group.

In some embodiments, the conjugation group comprises a receptor ligand.

In some embodiments, $c_A$, $c_B$, and $c_M$ each independently comprise a naturally-occurring amino acid or a non-naturally-occurring amino acid. In some embodiments, $c_A$, $c_B$, and $c_M$ each independently comprise a D amino acid, a L amino acid, an α-amino acid, a ß-amino acid, or a γ-amino acid. In some embodiments, $c_A$, $c_B$, and $c_M$ each independently comprise any amino acid having a free thiol group, any amino acid containing a free amine group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ each independently comprise D-cysteine, D-glutamate, lysine, and para-4-acetyl L-phenylalanine. In some embodiments, $c_B$ comprises any amino acid having a free thiol group. In some embodiments, $c_B$ comprises D-cysteine. In some embodiments, $c_A$ comprises any amino acid having a N-terminal amine group. In some embodiments, $c_A$ comprises D-glutamate. In some embodiments, $c_A$ comprises lysine. In some embodiments, $c_M$ comprises any amino acid with a side chain capable of forming an oxime or hydrazone bond upon reaction with a hydroxylamine or hydrazine group. In some embodiments, $c_M$ comprises para-4-acetyl L-phenylalanine.

In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, and a γ-amino acid. In some embodiments, $c_A$, $c_B$, and $c_M$ are each independently any amino acid having a free thiol group, any amino acid containing a free amine group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from: D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine.

Cargo (D)

Imaging Agents

In some embodiments, an imaging agent is a dye. In some embodiments, an imaging agent is a fluorescent moiety. In some embodiments, a fluorescent moiety is selected from: a fluorescent protein, a fluorescent peptide, a fluorescent dye, a fluorescent material or a combination thereof.

All fluorescent moieties are encompassed within the term "fluorescent moiety." Specific examples of fluorescent moieties given herein are illustrative and are not meant to limit the fluorescent moieties for use with the targeting molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 5-carboxyfluorescein, fluorescein-5-isothiocyanate, fluorescein-6-isothiocyanate and 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

Examples of cyanine dyes include, but are not limited to, Cy3, Cy3B, Cy3.5, Cy5, Cy5.5, Cy7, IRDYE680, Alexa Fluor 750, IRDye800CW, ICG.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the imaging agent is labeled with a positron-emitting isotope (e.g., $^{18}$F) for positron emission tomography (PET), gamma-ray isotope (e.g., $^{99m}$Tc) for single photon emission computed tomography (SPECT), or a paramagnetic molecule or nanoparticle (e.g., $Gd^{3+}$ chelate or coated magnetite nanoparticle) for magnetic resonance imaging (MRI).

In some embodiments, the imaging agent is labeled with: a gadolinium chelate, an iron oxide particle, a super paramagnetic iron oxide particle, an ultra small paramagnetic particle, a manganese chelate or gallium containing agent.

Examples of gadolinium chelates include, but are not limited to diethylene triamine pentaacetic acid (DTPA), 1,4,7,10-tetraazacyclododecane-1,4,7,10-tetraacetic acid (DOTA), and 1,4,7-triazacyclononane-N,N',N"-triacetic acid (NOTA).

In some embodiments, the imaging agent is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, the imaging agent is a nuclear probe. In some embodiments, the imaging agent is a SPECT or PET radionuclide probe. In some embodiments, the radionuclide probe is selected from: a technetium chelate, a copper chelate, a radioactive fluorine, a radioactive iodine, a indiuim chelate.

Examples of Tc chelates include, but are not limited to HYNIC, DTPA, and DOTA.

In some embodiments, the imaging agent contains a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{64}$Cu radioactive isotopes of Lu, and others.

In some embodiments, a selective delivery molecule according to Formula I comprising an imaging agent is employed in guided surgery. In some embodiments, the selective delivery molecule preferentially localized to cancerous, or other undesirable tissues (i.e. necrotic tissues). In some embodiments, a selective delivery molecule according to Formula I comprising an imaging agent is employed in a guided surgery to remove colorectal cancer. In some embodiments, guided surgery employing the selective delivery molecule allows a surgeon to excise as little healthy (i.e., non-cancerous) tissue as possible. In some embodiments, guided surgery employing the selective delivery molecule allows a surgeon to visualize and excise more cancerous tissue than the surgeon would have been able to excise without the presence of the selective delivery molecule. In some embodiments, the surgery is fluorescence-guided surgery.

Macromolecular Carriers (M)

The term "carrier" means an inert molecule that modulates plasma half-life, solubility, or bio-distribution. In some embodiments, a carrier modulates plasma half-life of a selective delivery molecule disclosed herein. In some embodiments, a carrier modulates solubility of a selective delivery molecule disclosed herein. In some embodiments, a carrier modulates bio-distribution of a selective delivery molecule disclosed herein.

In some embodiments, a carrier decreases uptake of a selective delivery molecule by non-target cells or tissues. In some embodiments, a carrier decreases uptake of a selective delivery molecule into cartilage. In some embodiments, a carrier decreases uptake of a selective delivery molecule into joints relative to target tissue.

In some embodiments, a carrier increases uptake of a selective delivery molecule by target cells or tissues. In some embodiments, a carrier decreases uptake of a selective delivery molecule into the liver relative to target tissue. In some embodiments, a carrier decreases uptake of a selective delivery molecule into kidneys. In some embodiments, a carrier enhances uptake into cancer tissue. In some embodiments, a carrier enhances uptake into lymphatic channels and/or lymph nodes.

In some embodiments, a carrier increases plasma half-life by reducing glomerular filtration. In some embodiments, a carrier modulates plasma half-life by increasing or decreases metabolism or protease degradation. In some embodiments, a carrier increases tumor uptake due to enhanced permeability and retention (EPR) of tumor vasculature. In some embodiments, a carrier increases the aqueous solubility of selective delivery molecule.

In some embodiments, any M is independently directly or indirectly (e.g., via $c_M$) bound to A, B, or X. In some embodiments, any M is independently bound to A at the n-terminal poly glutamate. In some embodiments, any M is independently bound to A (or, the n-terminal poly glutamate) by a covalent linkage. In some embodiments, any M is independently bound to B at the c-terminal polyarginine. In some embodiments, any M is independently bound to B (or, the c-terminal polyarginine) by a covalent linkage. In some embodiments, any M is independently directly or indirectly bound to linkers between X and A, X and B, B and C/N terminus, and A and C/N terminus. In some embodiments, the covalent linkage comprises an ether bond, thioether bond, amine bond, amide bond, oxime bond, carbon-carbon bond, carbon-nitrogen bond, carbon-oxygen bond, or carbon-sulfur bond.

In some embodiments, M is selected from a protein, a synthetic or natural polymer, or a dendrimer. In some embodiments, M is selected from dextran, a PEG polymer (e.g., PEG 0.5 kDa, PEG 2 kDa, PEG 5 kDa, PEG 12 kDa, PEG 20 kDa, PEG 30 kDa, and PEG40 kDa), albumin, or a combination thereof. In some embodiments, M is a PEG polymer.

In some embodiments, the size of M is between 50 and 70 kD.

In some embodiments, the selective delivery molecule is conjugated to albumin. In certain instances, albumin is excluded from the glomerular filtrate under normal physiological conditions. In some embodiments, the selective delivery molecule comprises a reactive group such as maleimide that can form a covalent conjugate with albumin. A selective delivery molecule comprising albumin results in enhanced accumulation of cleaved selective delivery molecules in tumors in a cleavage dependent manner. In some embodiments, albumin conjugates have good pharmacokinetic properties.

In some embodiments, the selective delivery molecule is conjugated to PEG polymers. In some embodiments, the selective delivery molecule is conjugated to PEG polymers having an average molecular weight of approximately 0.5 kDa (PEG 0.5 kDa). In some embodiments, the selective delivery molecule is conjugated to PEG polymers having an average molecular weight of approximately 1 kDa (PEG 1 kDa). In some embodiments, the selective delivery molecule is conjugated to PEG polymers having an average molecular weight of approximately 2 kDa (PEG 2 kDa). In some embodiments, the selective delivery molecule is conjugated to PEG polymers having an average molecular weight of approximately 5 kDa (PEG 5 kDa). In some embodiments, the selective delivery molecule is conjugated to PEG polymers having an average molecular weight of approximately 10 kDa (PEG 10 kDa). In some embodiments, the selective delivery molecule is conjugated PEG polymers having an average molecular weight of approximately 12 kDa (PEG 12 kDa). In some embodiments, selective delivery molecule is conjugated to PEG polymers having an average molecular weight of approximately 20 kDa (PEG 20 kDa). In some embodiments, selective delivery molecule is conjugated to PEG polymers having an average molecular weight of approximately 30 kDa (PEG 30 kDa). In some embodiments, selective delivery molecules conjugated to PEG30 kDa had a longer half-life as compared to free peptides. In some embodiments, selective delivery molecules are conjugated to PEG polymers having an average molecular weight of between about 20 to about 40 kDa which have hepatic and renal clearance.

In some embodiments, the selective delivery molecule is conjugated to a dextran. In some embodiments, the selective delivery molecule is conjugated to a 70 kDa dextran. In some embodiments, dextran conjugates, being a mixture of molecular weights, are difficult to synthesize and purify reproducibly.

In some embodiments, the selective delivery molecule is conjugated to streptavidin.

In some embodiments, the selective delivery molecule is conjugated to a fifth generation PAMAM dendrimer.

In some embodiments, a carrier is capped. In some embodiments, capping a carrier improves the pharmacokinetics and reduces cytotoxicity of a carrier by adding hydrophilicity. In some embodiments, the cap is selected from: Acetyl, succinyl, 3-hydroxypropionyl, 2-sulfobenzoyl, glycidyl, PEG-2 kDa, PEG-4 kDa, PEG-8 kDa and PEG-12 kDa.

Portion X (Linkers)

In some embodiments, a linker consisting of one or more amino acids is used to join peptide sequence A (i.e., the sequence designed to inhibit the delivery action of peptide B) and peptide sequence B. Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In live cells, an intact selective delivery molecule disclosed herein may not be able to enter the cell because of the presence of portion A. Thus, a strictly intracellular process for cleaving X would be ineffective to cleave X in healthy cells since portion A, preventing uptake into cells, would not be effectively cleaved by intracellular enzymes in healthy cells since it would not be taken up and would not gain access to such intracellular enzymes. However, where a cell is injured or diseased (e.g., cancerous cells, hypoxic cells, ischemic cells, apoptotic cells, necrotic cells) such intracellular enzymes leak out of the cell and cleavage of A would occur, allowing entry of portion B and/or cargo into the cell, effecting targeted delivery of portion B and/or cargo D to neighboring cells. In some embodiments, X is cleaved in the extracellular space.

In certain instances, capillaries are leaky around tumors and other trauma sites. In some embodiments, leaky capillaries enhance the ability of high molecular weight molecules (e.g., molecular weight of about 30 kDa or more) to reach the interstitial compartment. In some embodiments, X linker is cleaved adjacent to cancerous tissue. In some embodiments, cells that do not express the relevant protease but that are immediately adjacent to cells expressing the relevant protease pick up cargo from a selective delivery molecule because linkage of a X linker is typically extracellular. In some embodiments, such bystander targeting is beneficial in the treatment of tumors because of the heterogeneity of cell phenotypes and the wish to eliminate as high a percentage of suspicious cells as possible.

In some embodiments, X is a cleavable linker.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, X is about 5 to about 30 atoms in length. In some embodiments, X is about 6 atoms in length. In some embodiments, X is about 8 atoms in length. In some embodiments, X is about 10 atoms in length. In some embodiments, X is about 12 atoms in length. In some embodiments, X is about 14 atoms in length. In some embodiments, X is about 16 atoms in length. In some embodiments, Xis about 18 atoms in length. In some embodiments, Xis about 20 atoms in length. In some embodiments, X is about 25 atoms in length. In some embodiments, X is about 30 atoms in length.

In some embodiments, the linker binds peptide portion A (i.e., the peptide sequence which prevents cellular uptake) to peptide portion B (i.e., the delivery sequence) by a covalent linkage. In some embodiments, the covalent linkage comprises an ether bond, thioether bond, amine bond, amide bond, oxime bond, hydrazone bond, carbon-carbon bond, carbon-nitrogen bond, carbon-oxygen bond, or carbon-sulfur bond.

In some embodiments, X comprises a peptide linkage. The peptide linkage comprises L-amino acids and/or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

In some embodiments, a X linker is designed for cleavage in the presence of particular conditions or in a particular environment. In preferred embodiments, a X linker is cleavable under physiological conditions. Cleavage of such a X linker may, for example, be enhanced or may be affected by particular pathological signals or a particular environment related to cells in which cargo delivery is desired. The design of a X linker for cleavage by specific conditions, such as by a specific enzyme, allows the targeting of cellular uptake to a specific location where such conditions obtain. Thus, one important way that selective delivery molecules provide specific targeting of cellular uptake to desired cells, tissues, or regions is by the design of the linker portion X to be cleaved by conditions near such targeted cells, tissues, or regions.

In some embodiments, X is a pH-sensitive linker. In some embodiments, X is cleaved under basic pH conditions. In some embodiments, X is cleaved under acidic pH conditions. In some embodiments, X is cleaved by a protease, a matrix metalloproteinase, or a combination thereof. In some embodiments, X is cleaved by a reducing agent. In some embodiements X is cleaved by an oxidizing agent.

In some embodiments, X is cleaved by an MMP. The hydrolytic activity of matrix metalloproteinases (MMPs) has been implicated in the invasive migration of metastatic tumor cells. In certain instances, MMPs are found near sites of inflammation. In certain instances, MMPs are found near sites of stroke (i.e., a disorder characterized by brain damage following a decrease in blood flow). Thus, uptake of molecules having features of the invention are able to direct cellular uptake of cargo (at least one D moiety) to specific cells, tissues, or regions having active MMPs in the extracellular environment. In some embodiments, X comprises an amino-acid sequence selected from: PLG-C(Me)-AG (SEQ ID NO: 1), PLGLAG (SEQ ID NO: 2) or RPLALWRS (SEQ ID NO: 3). In some embodiments, X is cleaved by a metalloproteinase enzymes selected from MMP-2, MMP-9, or MMP-7 (MMPs involved in cancer and inflammation). In some embodiments, the linker is cleaved by MMP-2. In some embodiments, the linker is cleaved by MMP-9. In some embodiments, the linker is cleaved by MMP-7.

In some embodiments, X is cleaved by proteolytic enzymes or reducing environment, as may be found near cancerous cells. Such an environment, or such enzymes, are typically not found near normal cells.

In some embodiments, X is cleaved by serine proteases including but not limited to thrombin and cathepsins. In some embodiments, X is cleaved by cathepsin K, cathepsin S, cathepsin D, cathepsin E, cathepsin W, cathepsin F, cathepsin A, cathepsin C, cathepsin H, cathepsin Z, or any combinations thereof. In some embodiments, X is cleaved by cathepsin K and/or cathepsin S.

In some embodiments, X is cleaved in or near tissues suffering from hypoxia. In some embodiments, cleavage in or near hypoxic tissues enables targeting of cancer cells and cancerous tissues, infarct regions, and other hypoxic regions. In some embodiments, X comprises a disulfide bond. In some embodiments, a linker comprising a disulfide bond is preferentially cleaved in hypoxic regions and so targets cargo delivery to cells in such a region. Hypoxia is thought to cause cancer cells to become more resistant to radiation and chemotherapy, and also to initiate angiogenesis. In a hypoxic environment in the presence of, for example, leaky or necrotic cells, free thiols and other reducing agents become available extracellularly, while the $O_2$ that normally keeps the extracellular environment oxidizing is by definition depleted. In some embodiments, this shift in the redox balance promotes reduction and cleavage of a disulfide bond within a X linker. In addition to disulfide linkages which take advantage of thiol-disulfide equilibria, linkages including quinones that fall apart when reduced to hydroquinones are used in a X linker designed to be cleaved in a hypoxic environment.

In some embodiments, X is cleaved in a necrotic environment. Necrosis often leads to the release of enzymes or other cell contents that may be used to trigger cleavage of a X linker. In some embodiments, cleavage of X by necrotic enzymes (e.g., by calpains) allows cargo to be taken up by diseased cells and by neighboring cells that had not yet become fully leaky.

In some embodiments, X is an acid-labile linker. In some embodiments, X comprises an acetal or vinyl ether linkage. Acidosis is observed in sites of damaged or hypoxic tissue, due to the Warburg shift from oxidative phosphorylation to anaerobic glycolysis and lactic acid production. In some embodiments, acidosis is used as a trigger of cargo uptake by replacing some of the arginines within B by histidines, which only become cationic below pH 7.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, the linker X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO: 9), PPRSFL (SEQ ID NO:10), RLQLKL (SEQ ID NO: 11), and RLQLK(Ac) (SEQ ID NO: 12). In some embodiments, the linker X comprises the amino acid sequence PLGLAG (SEQ ID NO: 2). In some embodiments, the linker X comprises the amino acid sequence PLG-C(me)-AG (SEQ ID NO: 1). In some embodiments, the linker X comprises the amino acid sequence PLGxAG (SEQ ID NO: 20), wherein x is any amino acid (naturally-occuring or non-naturally occurring). In some embodiments, the linker X comprises the amino acid sequence RPLALWRS (SEQ ID NO: 3). In some embodiments, the linker X comprises the amino acid sequence ESPAYYTA (SEQ ID NO: 8). In some embodiments, the linker X comprises the amino acid sequence DPRSFL (SEQ ID NO: 9). In some embodiments, the linker X comprises the amino acid sequence PPRSFL (SEQ ID NO: 10). In some embodiments, the linker X comprises the amino acid sequence RLQLKL (SEQ ID NO: 11). In some embodiments, the linker X comprises the amino acid sequence RLQLK(Ac) (SEQ ID NO: 12).

In some embodiments, the linker X comprises a peptide selected from: PR(S/T)(L/I)(S/T), where the letters in parentheses indicate that either one of the indicated amino acids may be at that position in the sequence); GGAANLVRGG (SEQ ID NO: 21); SGRIGFLRTA (SEQ ID NO: 22); SGRSA (SEQ ID NO: 23); GFLG (SEQ ID NO:24); ALAL (SEQ ID NO: 25); FK; PIC(Et)F—F (SEQ ID NO: 26), where C(Et) indicates S-ethylcysteine (a cysteine with an ethyl group attached to the thiol) and the "—" indicates the typical cleavage site in this and subsequent sequences); GGPRGLPG (SEQ ID NO: 27); HSSKLQ (SEQ ID NO: 28); LVLA-SSSFGY (SEQ ID NO: 29); GVSQNY-PIVG (SEQ ID NO: 30); GVVQA-SCRLA (SEQ ID NO: 31); f(Pip)R—S, where "f" indicates D-phenylalanine and "Pip" indicates piperidine-2-carboxylic acid (pipecolinic acid, a proline analog having a six-membered ring); DEVD (SEQ ID NO: 32); GWEHDG (SEQ ID NO: 33); RPLALWRS (SEQ ID NO: 3), or a combination thereof.

In some embodiments, X is cleaved under hypoxic conditions. In some embodiments, X comprises a disulfide linkage. In some embodiments, X comprises a quinine.

In some embodiments, X is cleaved under necrotic conditions. In some embodiments, X comprises a molecule cleavable by a calpain.

In some embodiments, X comprises 6-aminohexanoyl, 5-(amino)-3-oxapentanoyl, or a combination thereof. In some embodiments, X comprises a disulfide linkage.

In some embodiments, the linker is an alkylene. In some embodiments, the linker is an alkenylene. In some embodiments, the linker is an alkynylene. In some embodiments, the linker is a heteroalkylene.

An "alkylene" group refers to an aliphatic hydrocarbon group. The alkylene moiety is a diradical and may be a saturated alkylene or an unsaturated alkylene.

The "alkylene" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkylene" where no numerical range is designated). The alkylene group could also be a "lower alkylene" having 1 to 6 carbon atoms. The alkylene group of the compounds described herein may be designated as "C1-C4 alkylene" or similar designations. By way of example only, "C1-C4 alkylene" indicates that there are one to four carbon atoms in the alkylene chain, i.e., the alkylene chain is selected from: methylene, ethylene, propylene, iso-propylene, n-butylene, iso-butylene, sec-butylene, and t-butylene. Typical alkylene groups include, but are in no way limited to, methylene, ethylene, propylene, isopropylene, butylene, isobutylene, tertiary butylene, pentylene, hexylene, ethenylene, propenylene, butenylene, and the like.

In some embodiments, the linker comprises a diradical ring structure (e.g., an arylene). As used herein, the term "ring" refers to any covalently closed structure. Rings include, for example, carbocycles (e.g., arylenes and cycloalkylenes), heterocycles (e.g., heteroarylenes and non-aromatic heterocyclenes), aromatics (e.g. arylenes and heteroarylenes), and non-aromatics (e.g., cycloalkylenes and non-aromatic heterocyclenes). Rings can be optionally substituted. Rings can be monocyclic or polycyclic.

As used herein, the term "arylene" refers to a aromatic ring diradical wherein each of the atoms forming the ring is a carbon atom. Arylene rings can be formed by five, six, seven, eight, nine, or more than nine carbon atoms. Arylene groups can be optionally substituted. Examples of arylene groups include, but are not limited to phenylene, naphthalenylene, phenanthrenylene, anthracenylene, fluorenylene, and indenylene.

The term "cycloalkylene" refers to a monocyclic or polycyclic non-aromatic diradical, wherein each of the atoms forming the ring (i.e. skeletal atoms) is a carbon atom. Cycloalkylenes may be saturated, or partially unsaturated. Cycloalkylene groups include groups having from 3 to 10 ring atoms. Cycloalkylenes include, but are not limited to, cyclopropylene, cyclobutylene, cyclopentylene, cyclohexylene, cycloheptylene, and cyclooctylene.

In some embodiments, the ring is a cycloalkane. In some embodiments, the ring is a cycloalkene.

In some embodiments, the ring is an aromatic ring. The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic arylene (e.g., phenylene) and heterocyclic arylene (or "heteroarylene" or "heteroaromatic") groups (e.g., pyridinylene). The term includes monocyclic or fused-ring polycyclic (i.e., rings which share adjacent pairs of carbon atoms) groups.

In some embodiments, the ring is a heterocyclene. The term "heterocyclene" refers to diradical heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinylene. An example of a 4-membered heterocyclic group is azetidinylene (derived from azetidine). An example of a 5-membered heterocyclic group is thiazolylene. An example of a 6-membered heterocyclic group is pyridylene, and an example of a 10-membered heterocyclic group is quinolinylene. Examples of non-aromatic heterocyclic groups are pyrrolidinylene, tetrahydrofuranylene, dihydrofuranylene, tetrahydrothienylene, tetrahydropyranylene, dihydropyranylene, tetrahydrothiopyranylene, piperidinylene, morpholinylene, thiomorpholinylene, thioxanylene, piperazinylene, azetidinylene, oxetanylene, thietanylene, homopiperidinylene, oxepanylene, thiepanylene, oxazepinylene, diazepinylene, thiazepinylene, 1,2,3,6-tetrahydropyridinylene, 2-pyrrolinylene, 3-pyrrolinylene, indolinylene, 2H-pyranylene, 4H-pyranylene, dioxanylene, 1,3-dioxolanylene, pyrazolinylene, dithianylene, dithiolanylene, dihydropyranylene, dihydrothienylene, dihydrofuranylene, pyrazolidinylene, imidazolinylene, imidazolidinylene, 3-azabicyclo[3.1.0]hexanylene, 3-azabicyclo[4.1.0]heptanylene, 3H-indolylene and quinolizinylene. Examples of aromatic heterocyclic groups are pyridinylene, imidazolylene, pyrimidinylene, pyrazolylene, triazolylene, pyrazinylene, tetrazolylene, furylene, thienylene, isoxazolylene, thiazolylene, oxazolylene, isothiazolylene, pyrrolylene, quinolinylene, isoquinolinylene, indolylene, benzimidazolylene, benzofuranylene, cinnolinylene, indazolylene, indolizinylene, phthalazinylene, pyridazinylene, triazinylene, isoindolylene, pteridinylene, purinylene, oxadiazolylene, thiadiazolylene, furazanylene, benzofurazanylene, benzothiophenylene, benzothiazolylene, benzoxazolylene, quinazolinylene, quinoxalinylene, naphthyridinylene, and furopyridinylene. The foregoing groups, may be C-attached and/or N-attached where such is possible. The heterocyclic groups include benzo-fused ring systems and ring systems substituted with one or two oxo (=O) moieties such as pyrrolidin-2-one.

In some embodiments, the ring is fused. The term "fused" refers to structures in which two or more rings share one or more bonds. In some embodiments, the ring is a dimer. In some embodiments, the ring is a trimer. In some embodiments, the ring is a substituted.

The term "carbocyclic" or "carbocyclene" refers to a diradical ring wherein each of the atoms forming the ring is a carbon atom. Carbocyclene includes arylene and cycloalkylene. The term thus distinguishes carbocyclene from heterocycene ("heterocyclic") in which the ring backbone contains at least one atom which is different from carbon (i.e., a heteroatom). Heterocyclene includes heteroarylene and heterocycloalkylene. Carbocyclenes and heterocyclenes can be optionally substituted.

In some embodiments, the linker is substituted. The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be LsRs, wherein each Ls is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)2-, —OC(=O)NH—, —NHC(=O)O—, —($C_1$-$C_6$alkyl)-, or —($C_2$-$C_6$alkenyl)-; and each Rs is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

In some embodiments, a selective delivery molecules disclosed herein comprises a single of linker. Use of a single mechanism to mediate uptake of both imaging and therapeutic cargoes is particularly valuable, because imaging with noninjurious tracer quantities can be used to test whether a subsequent therapeutic dose is likely to concentrate correctly in the target tissue.

In some embodiments, a selective delivery molecules disclosed herein comprises a plurality of linkers. Where a selective delivery molecule disclosed herein includes multiple X linkages, separation of portion A from the other portions of the molecule requires cleavage of all X linkages. Cleavage of multiple X linkers may be simultaneous or sequential. Multiple X linkages may include X linkages having different specificities, so that separation of portion A from the other portions of the molecule requires that more than one condition or environment ("extracellular signals") be encountered by the molecule. Cleavage of multiple X X linkers thus serves as a detector of combinations of such extracellular signals. For example, a selective delivery molecule may include two linker portions Xa and Xb connecting basic portion B with acidic portion A. Both Xa and Xb linkers must be cleaved before acidic portion A is separated from basic portion B allowing entry of portion B and cargo moiety C (if any) to enter a cell. It will be understood that a linker region may link to either a basic portion B or a cargo moiety C independently of another linker that may be present, and that, where desired, more than two linker regions X may be included.

Combinations of two or more X linkers may be used to further modulate the targeting and delivery of molecules to desired cells, tissue or regions. Combinations of extracellular signals are used to widen or narrow the specificity of the cleavage of X linkers if desired. Where multiple X linkers are linked in parallel, the specificity of cleavage is narrowed, since each X linker must be cleaved before portion A may separate from the remainder of the molecule. Where multiple X linkers are linked in series, the specificity of cleavage is broadened, since cleavage on any one X linker allows separation of portion A from the remainder of the molecule. For example, in order to detect either a protease OR hypoxia (i.e., to cleave X in the presence of either protease or hypoxia), a X linker is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X in the presence of both protease and hypoxia but not in the presence of only one alone), a X linker is designed to place the protease sensitive site between at least one pair of cysteines that are disulfide-bonded to each other. In that case, both protease cleavage and disulfide reduction are required in order to allow separation of portion A.

Exemplary Selective Delivery Molecules

Disclosed herein, in certain embodiments, is a selective delivery molecule according to SDM-41. Disclosed herein, in certain embodiments, is a selective delivery molecule according to SDM-42. Disclosed herein, in certain embodiments, is a selective delivery molecule according to SDM-43. Disclosed herein, in certain embodiments, is a selective delivery molecule according to SDM-44. Disclosed herein, in certain embodiments, is a selective delivery molecule according to SDM-45. Disclosed herein, in certain embodiments, is a selective delivery molecule according to SDM-46. Disclosed herein, in certain embodiments, is a selective delivery molecule according to SDM-47. Disclosed herein, in certain embodiments, is a selective delivery molecule according to SDM-48. Disclosed herein, in certain embodiments, is a selective delivery molecule according to SDM-49. Disclosed herein, in certain embodiments, is a selective delivery molecule according to SDM-50. Disclosed herein, in certain embodiments, is a selective delivery molecule according to SDM-51. Disclosed herein, in certain embodiments, is a selective delivery molecule according to SDM-52. Disclosed herein, in certain embodiments, is a selective delivery molecule according to SDM-53. Disclosed herein, in certain embodiments, is a selective delivery molecule according to SDM-54. Disclosed herein, in certain embodiments, is a selective delivery molecule according to SDM-55. Disclosed herein, in certain embodiments, is a selective delivery molecule according to SDM-56. Disclosed herein, in certain embodiments, is a selective delivery molecule according to SDM-57. Disclosed herein, in certain embodiments, is a selective delivery molecule according to SDM-58. Disclosed herein, in certain embodiments, is a selective delivery molecule according to SDM-59. Disclosed herein, in certain embodiments, is a selective delivery molecule according to SDM-60. Disclosed herein, in certain embodiments, is a selective delivery molecule according to SDM-61. Disclosed herein, in certain embodiments, is a selective delivery molecule according to SDM-62. Disclosed herein, in certain embodiments, is a selective delivery molecule according to SDM-63. Disclosed herein, in certain embodiments, is a selective delivery molecule according to SDM-64. Disclosed herein, in certain embodiments, is a selective delivery molecule according to SDM-65.

The structures of selective delivery molecules SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, and SDM-65 are shown below.

| | Chemical Structure |
|---|---|
| SDM-41 | 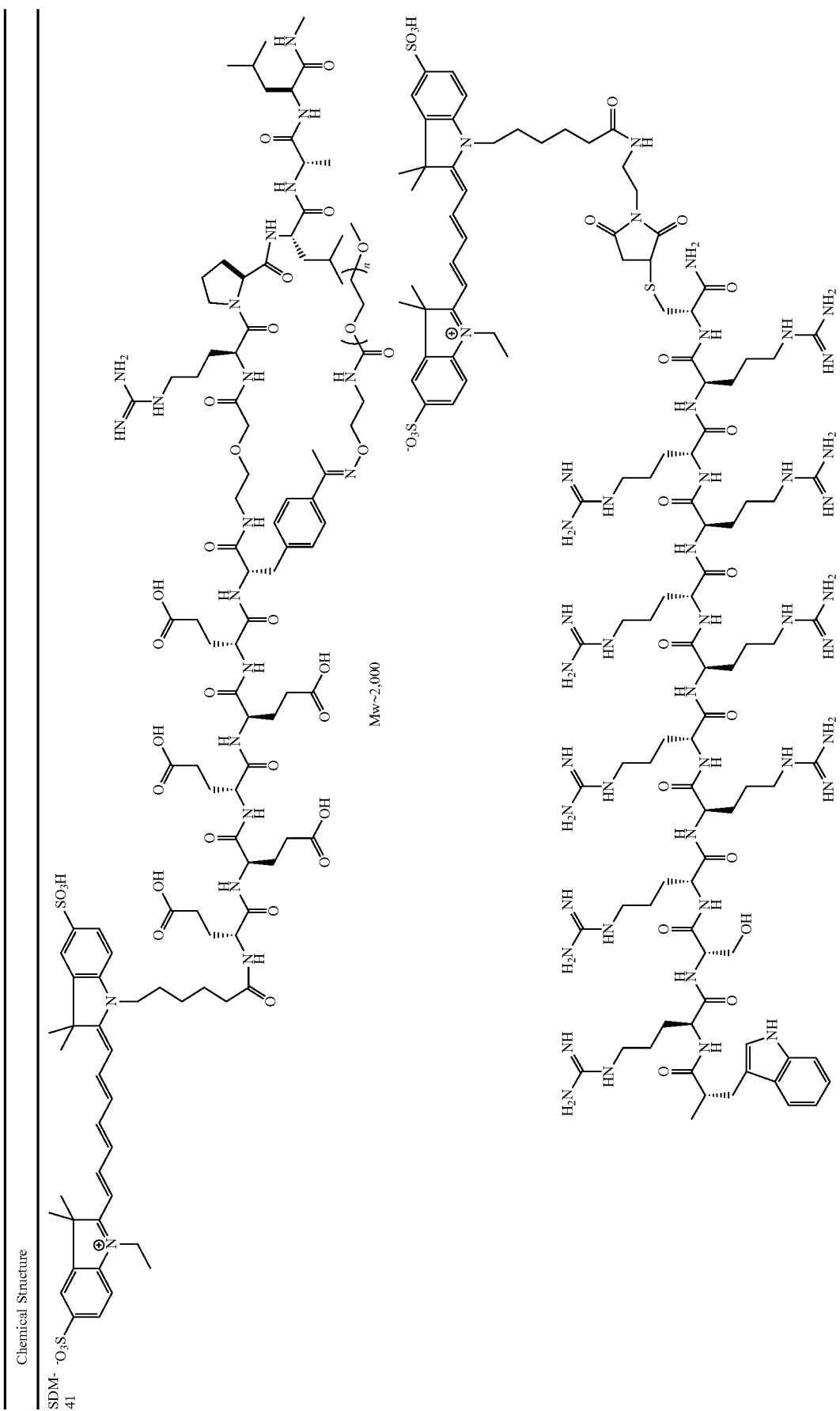 |

| | Chemical Structure |
|---|---|
| SDM-42 | 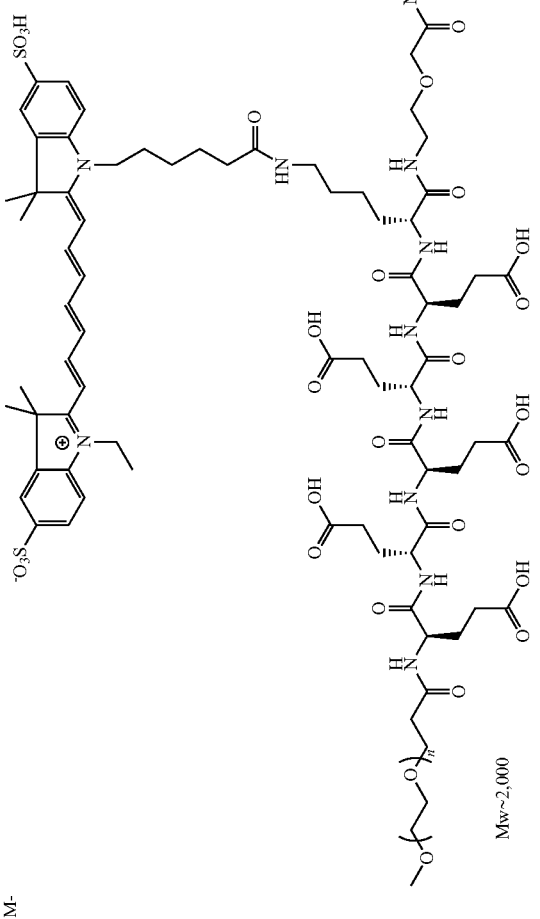 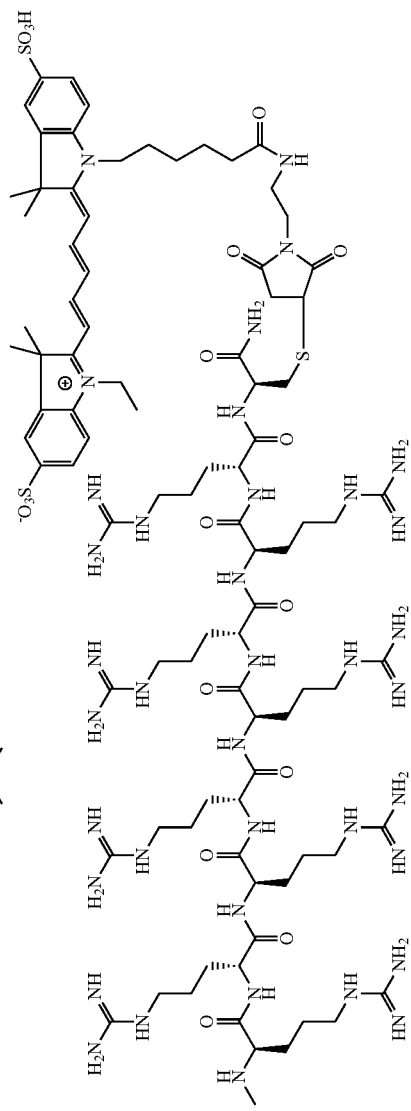 |

| Chemical Structure |
|---|
| SDM-43 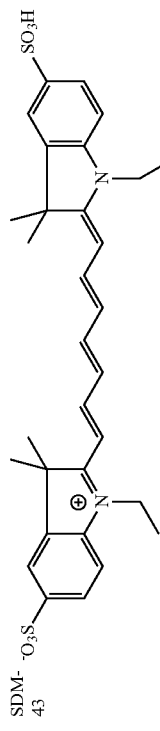 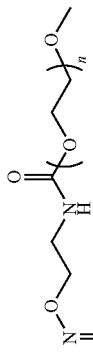 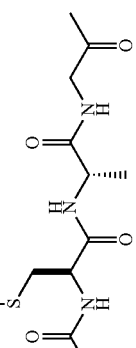 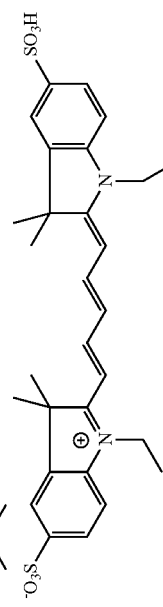 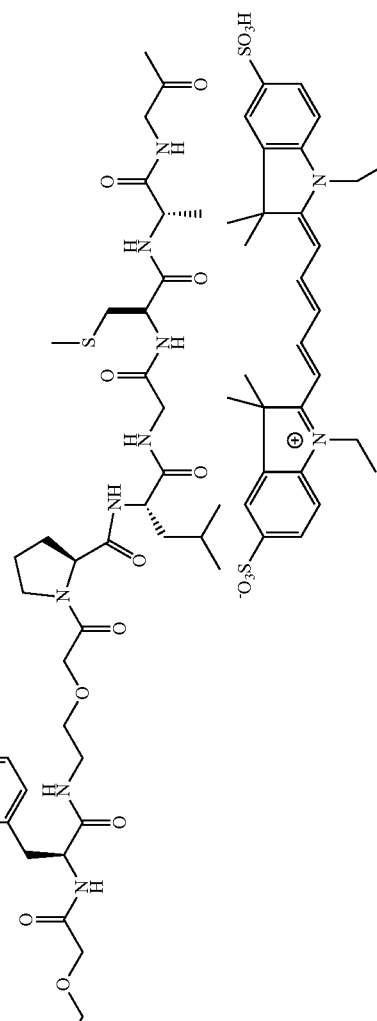 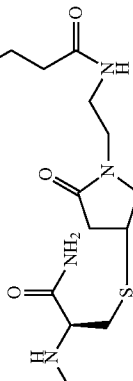 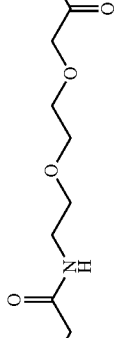 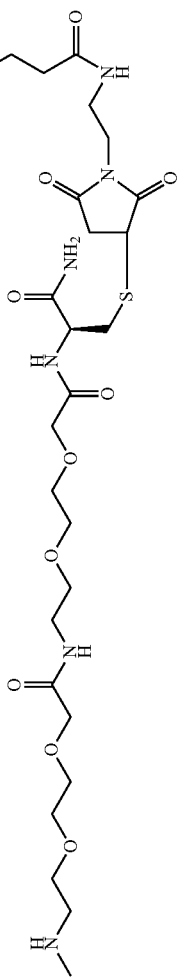 |

-continued
| Chemical Structure |
|---|
| SDM-44 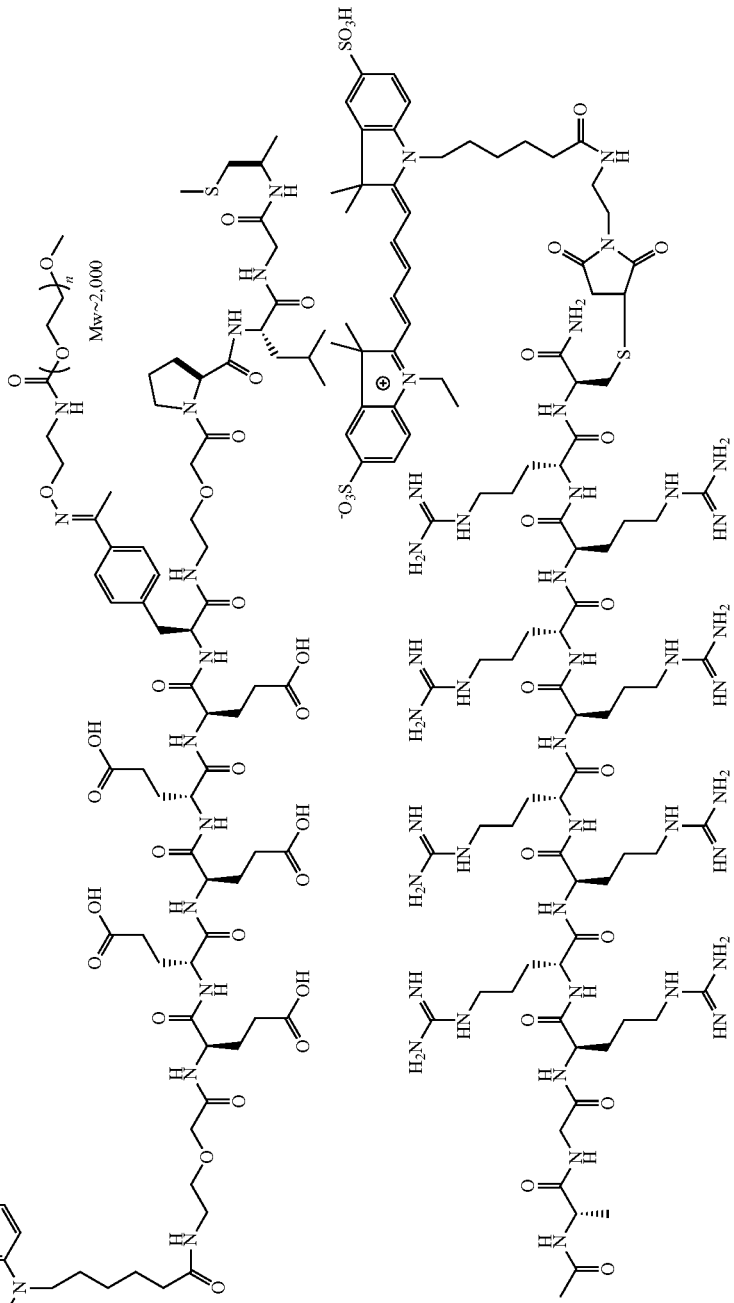 |

| Chemical Structure |
|---|
| SDM-45 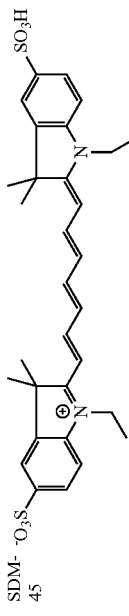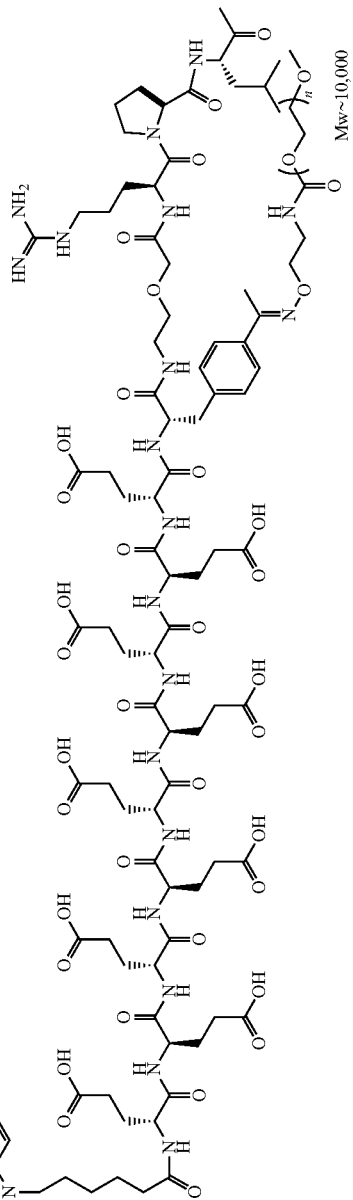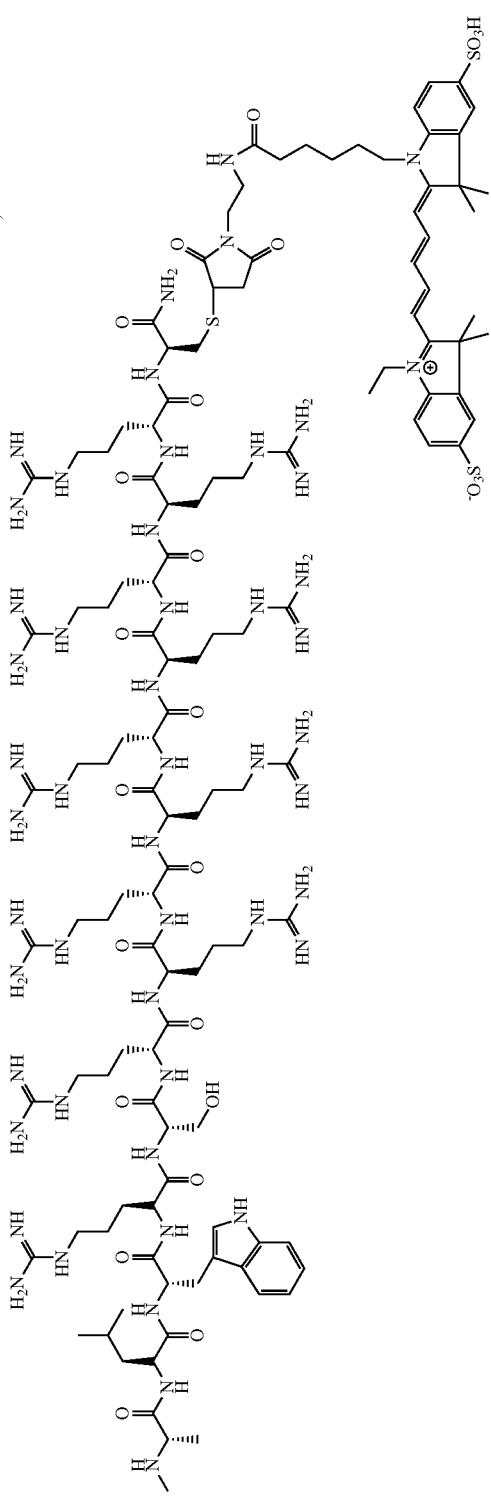 |

| Chemical Structure |
|---|
| SDM-46 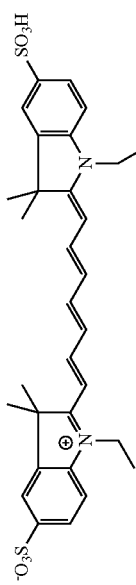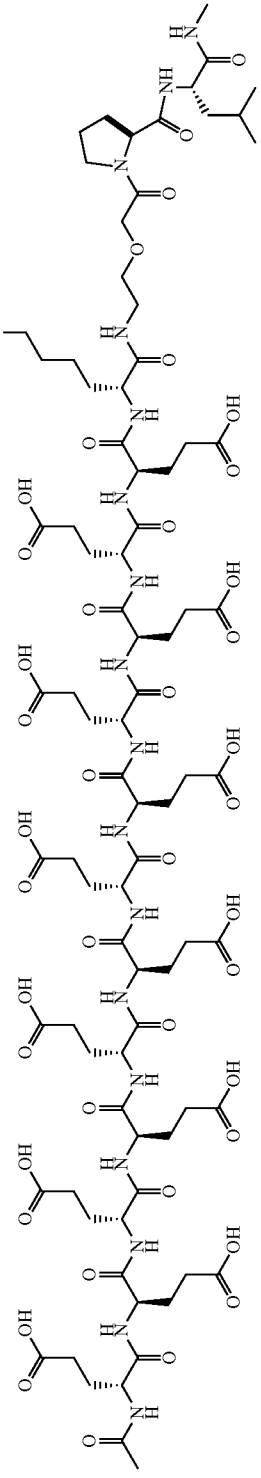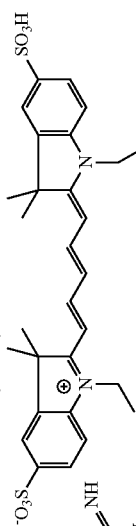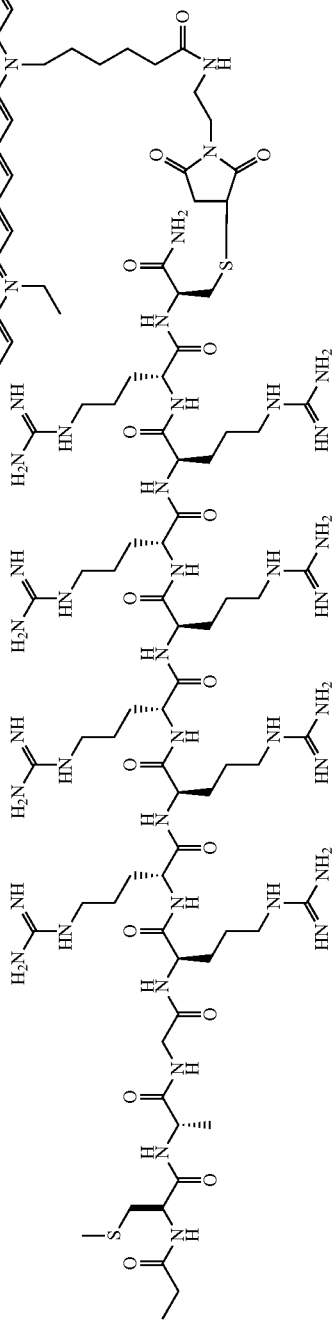 |

| | Chemical Structure |
|---|---|
| SDM-47 | (chemical structure) |

| | Chemical Structure |
|---|---|
| SDM-48 | 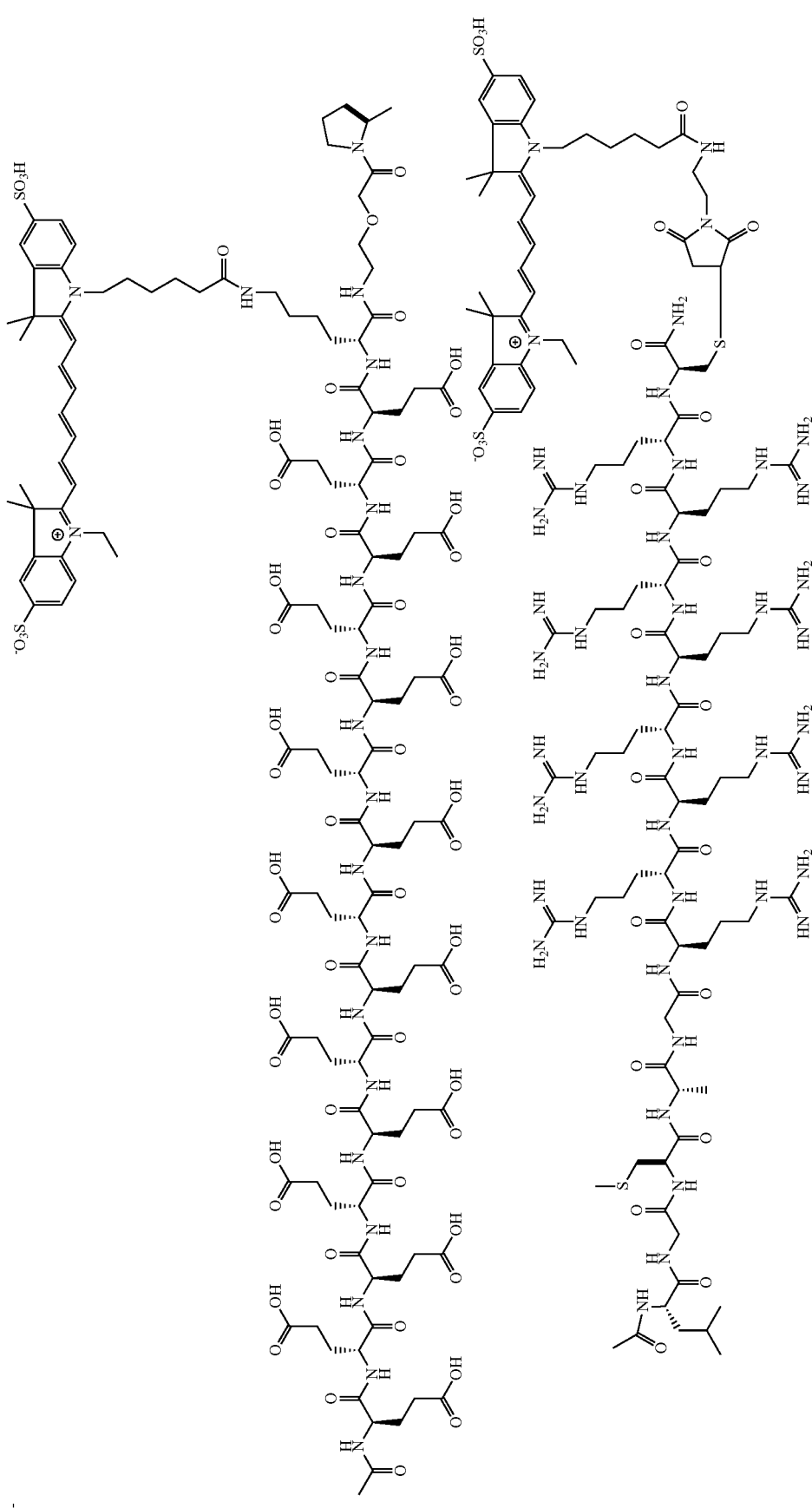 |

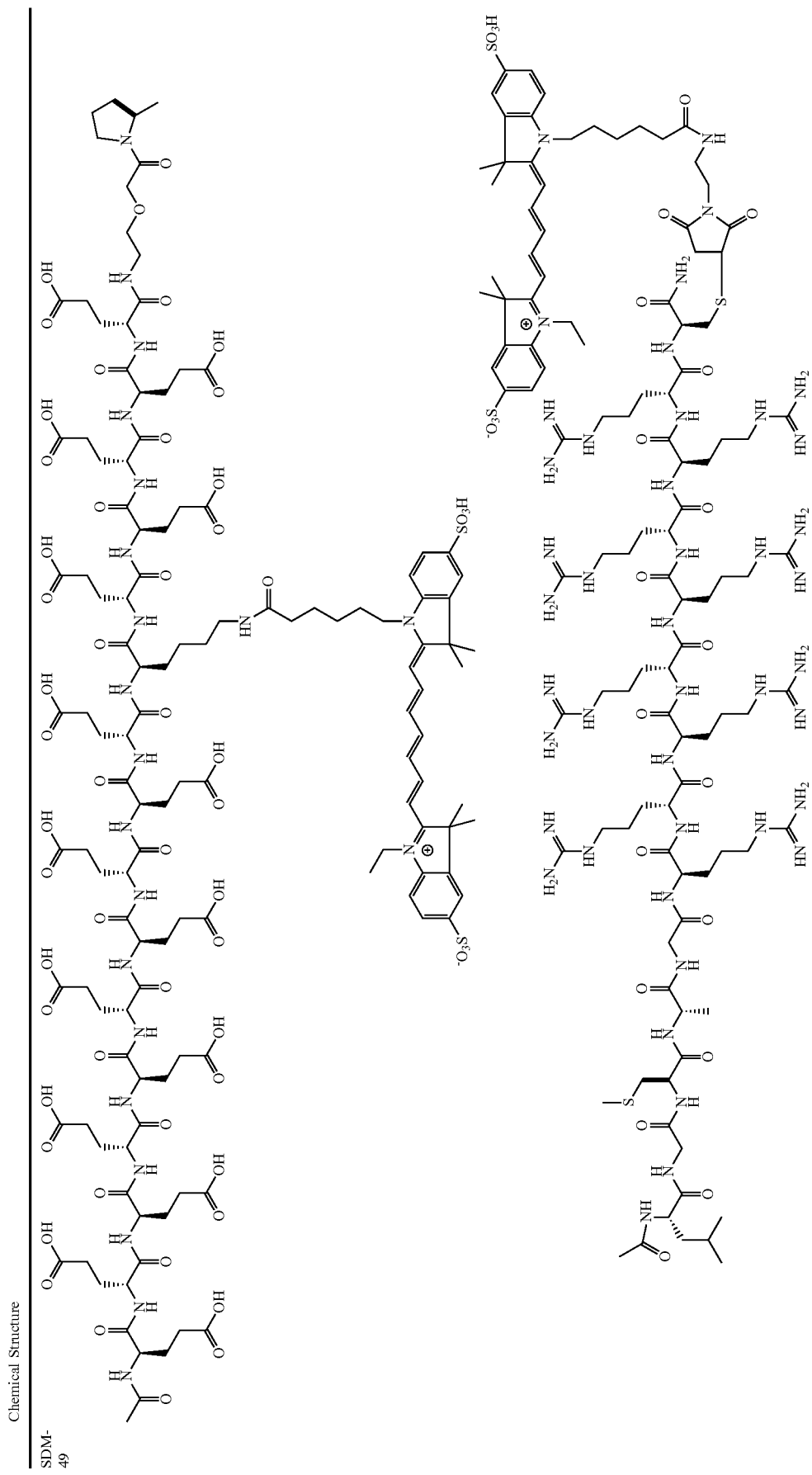

| | Chemical Structure |
|---|---|
| SDM-50 | 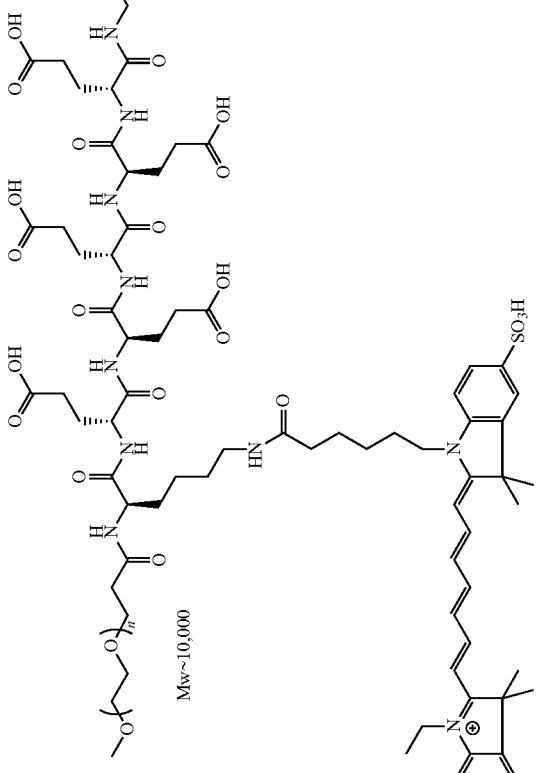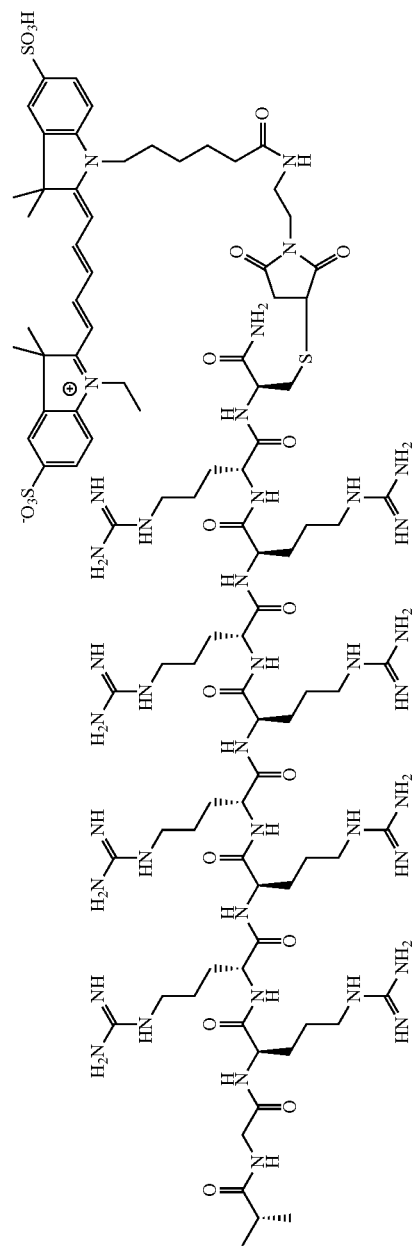 |

| | Chemical Structure |
|---|---|
| SDM-51 | 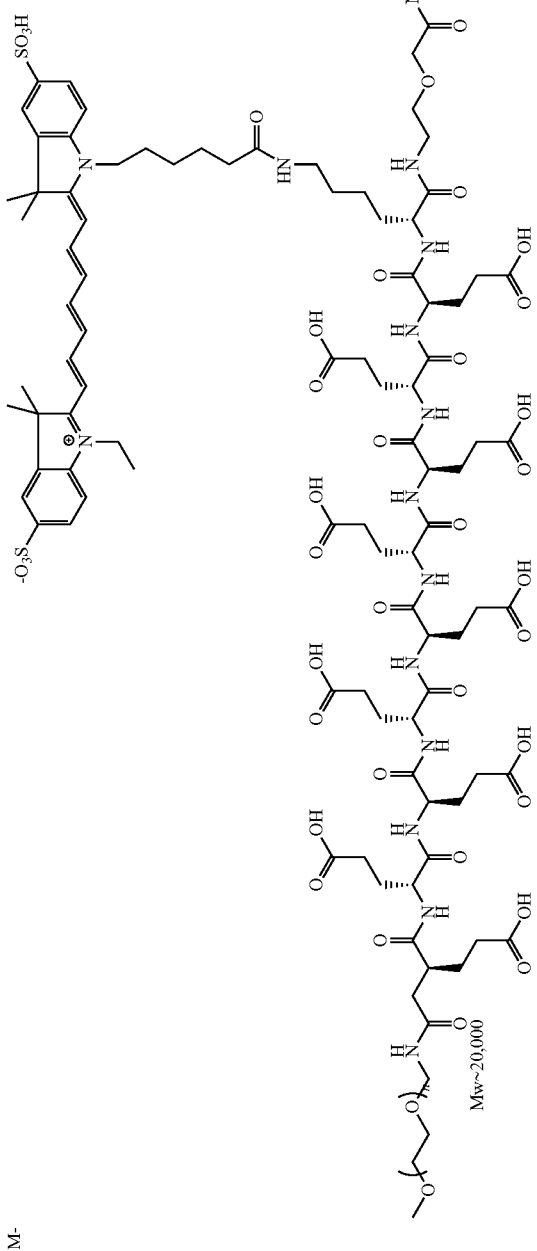 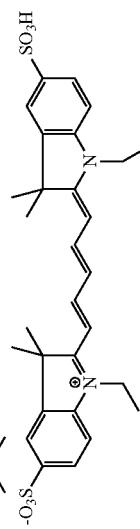 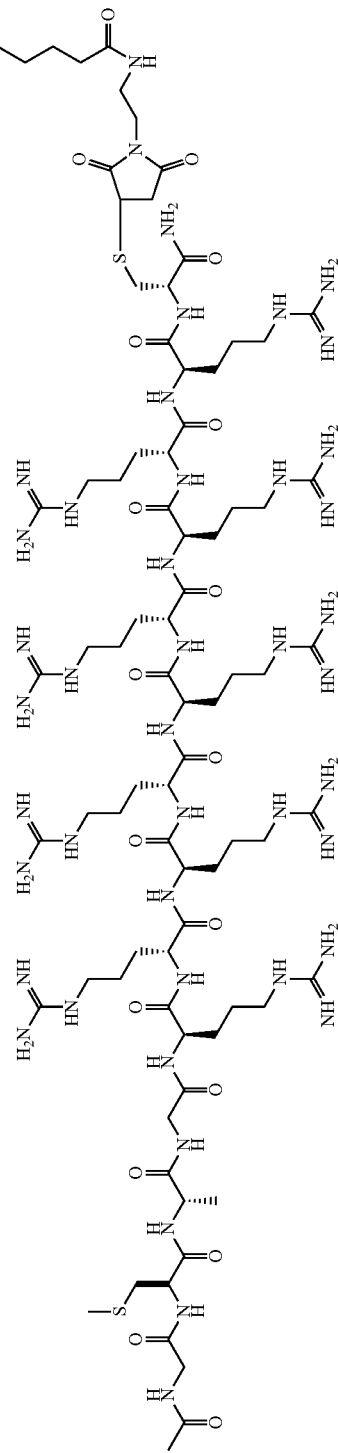 |

| | 51 | 52 |
|---|---|---|
| Chemical Structure | 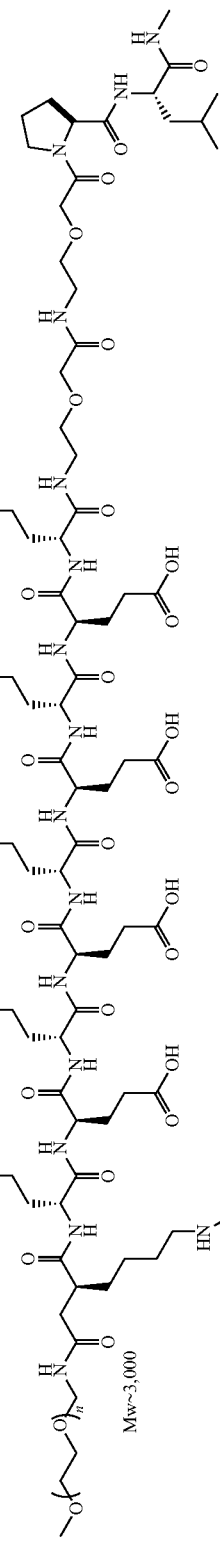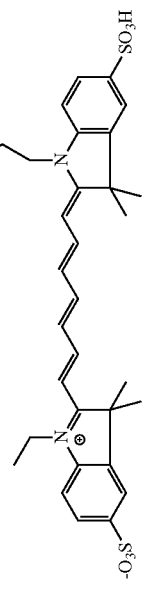 | 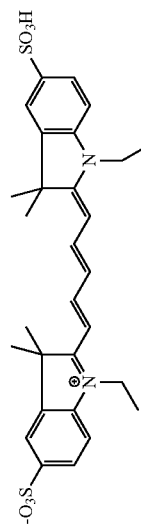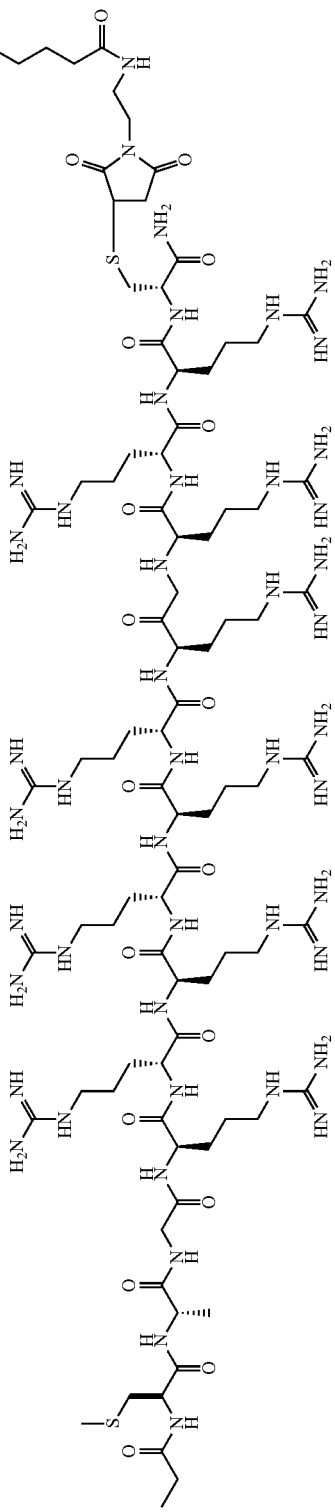 |
| SDM-52 | | |

| Chemical Structure |
|---|
| SDM-53 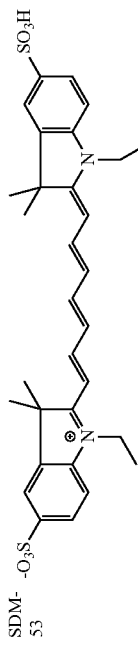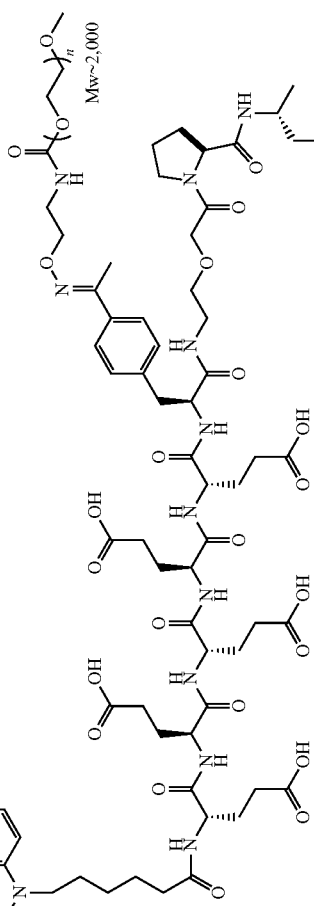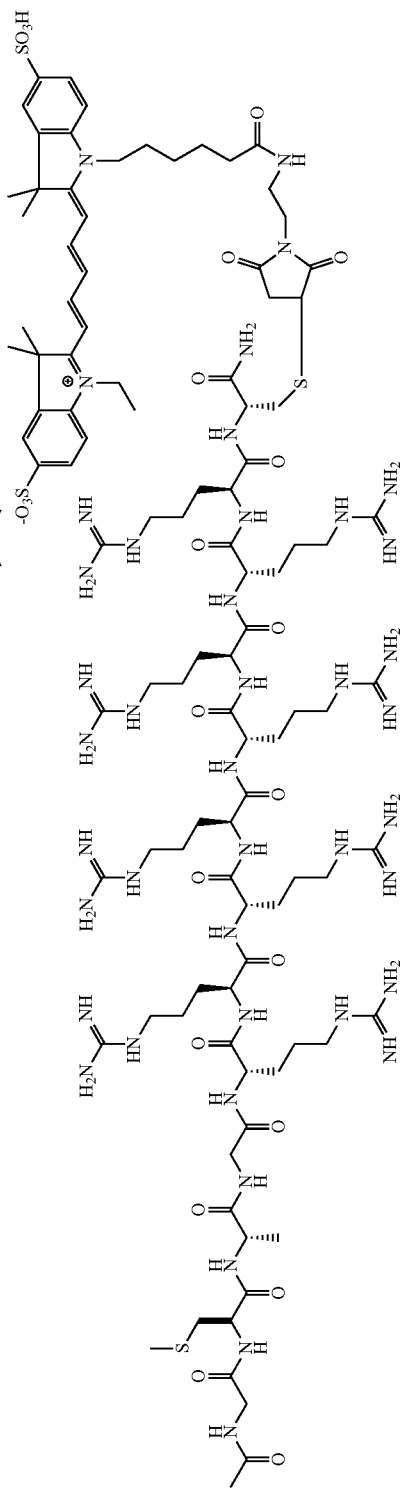 |

| | Chemical Structure |
|---|---|
| SDM-54 | 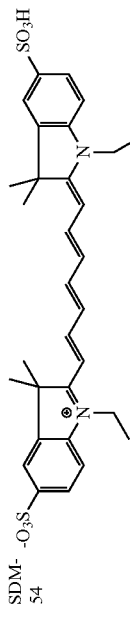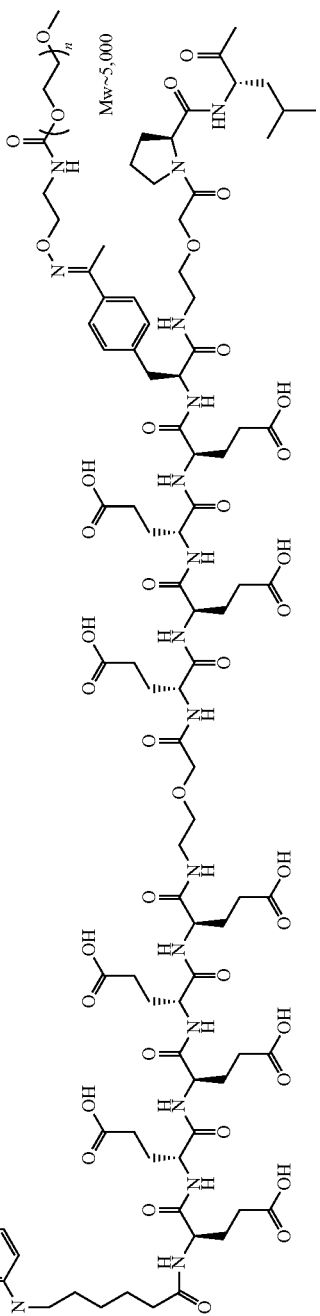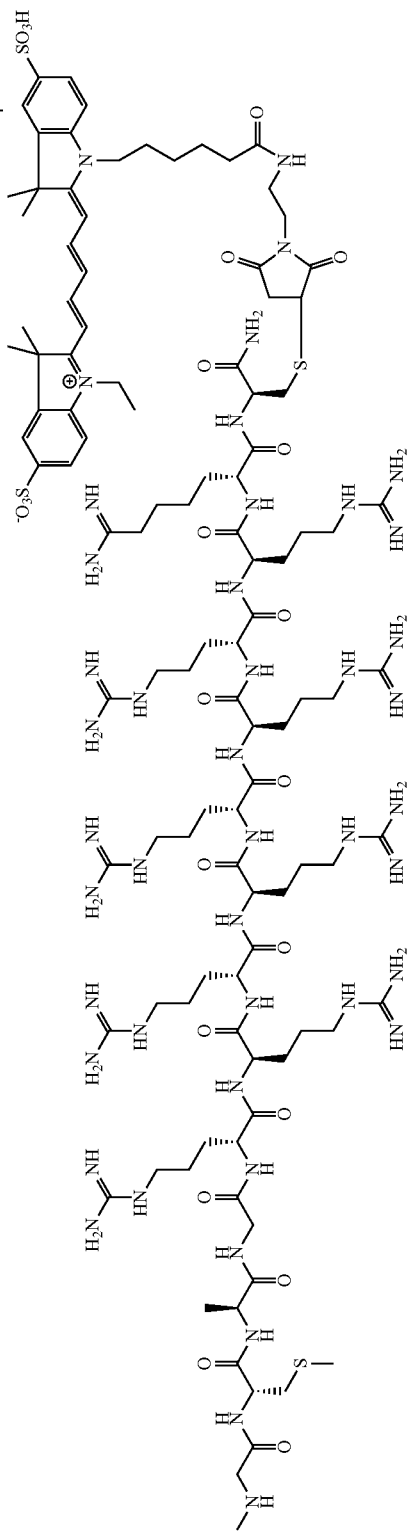 |

| | Chemical Structure |
|---|---|
| SDM-55 | 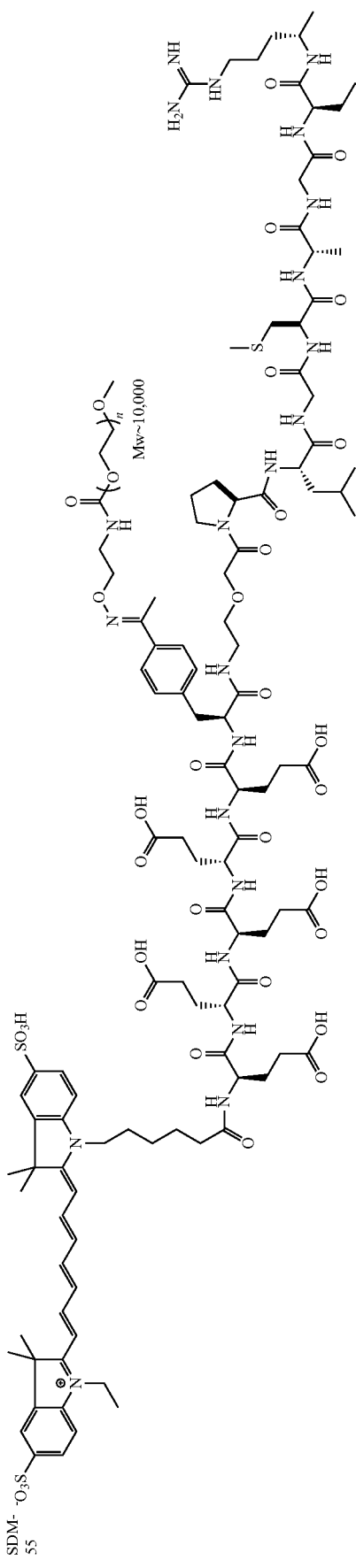 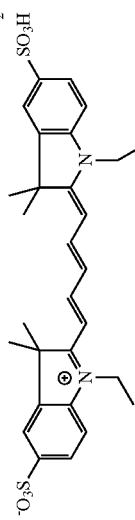 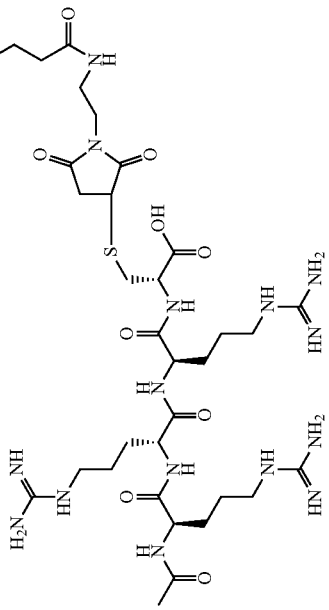 |

| Chemical Structure |
|---|
| SDM-56  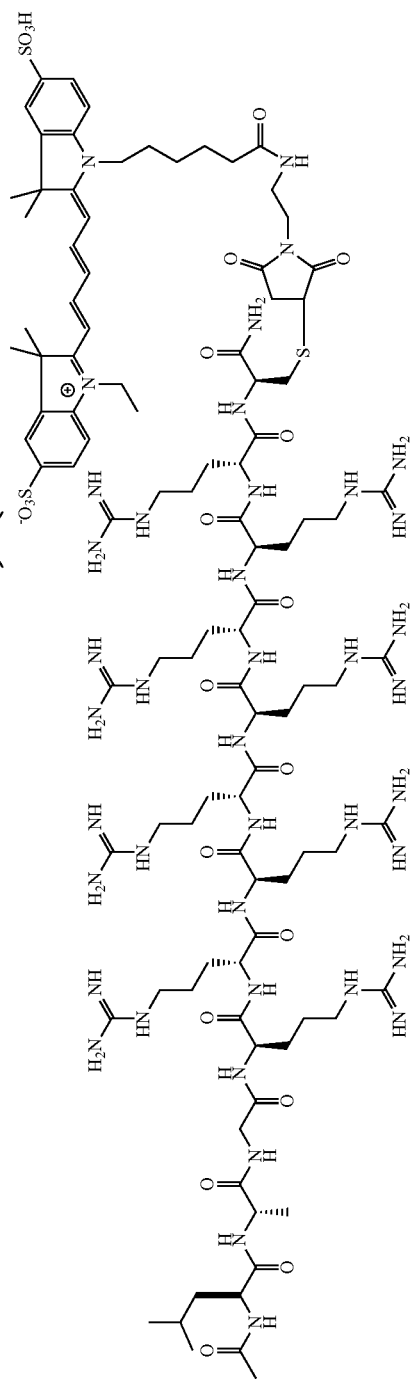 |

| Chemical Structure |
|---|
| SDM-57 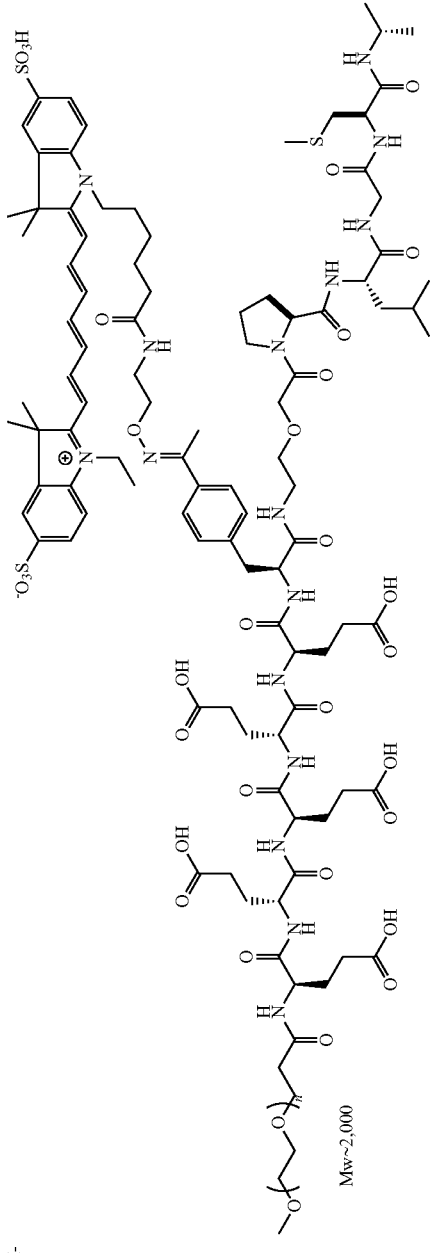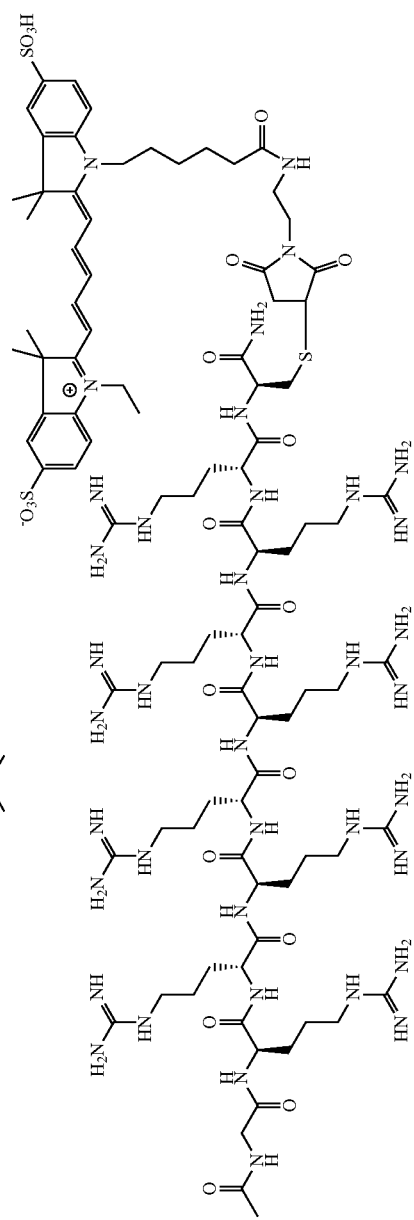 |

| Chemical Structure |
|---|
| SDM-58 | 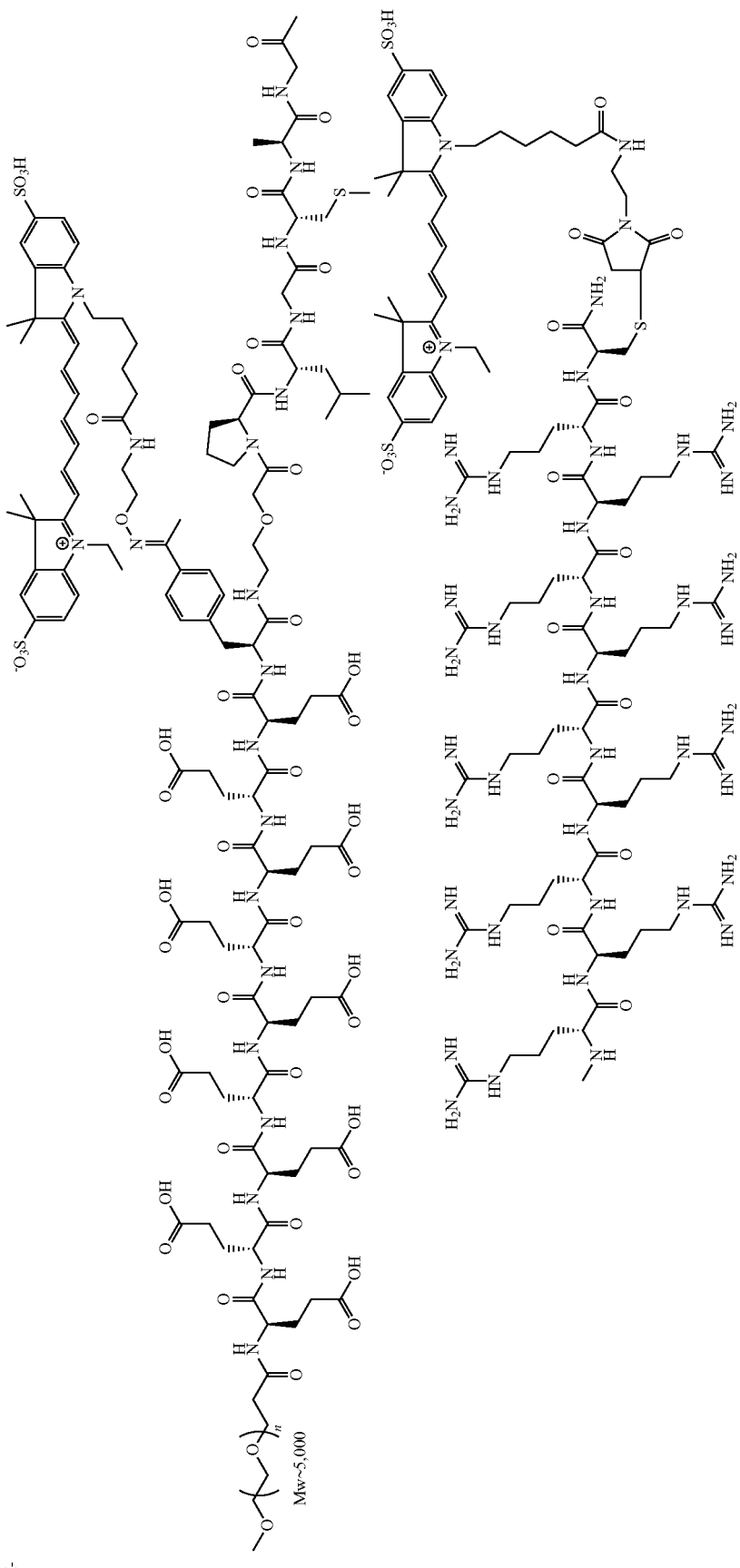 |

| Chemical Structure |
|---|
| SDM-59 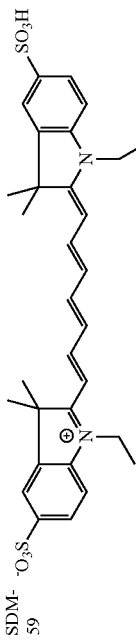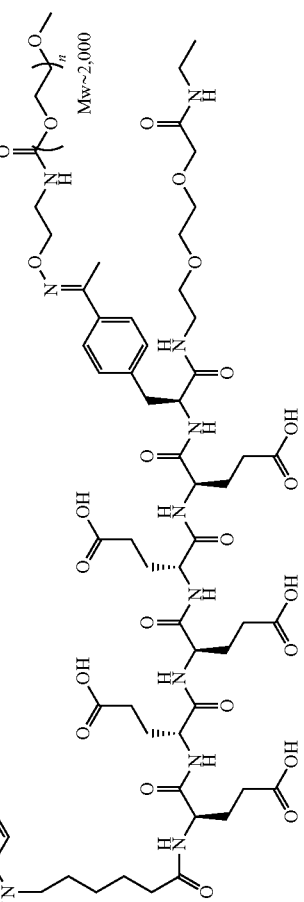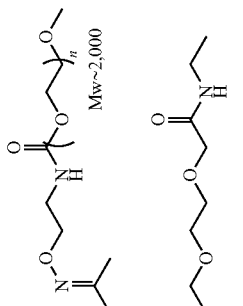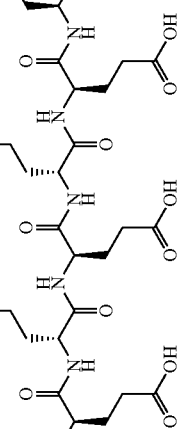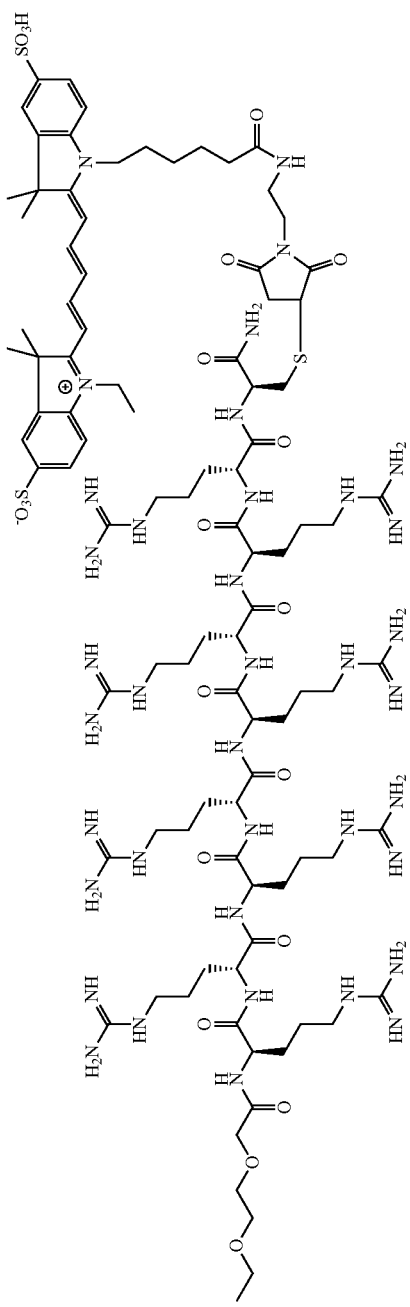 |

| | Chemical Structure |
|---|---|
| SDM-60 | 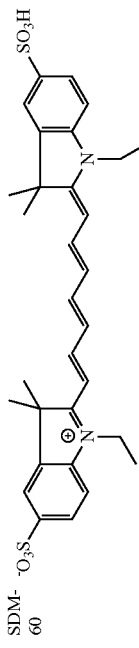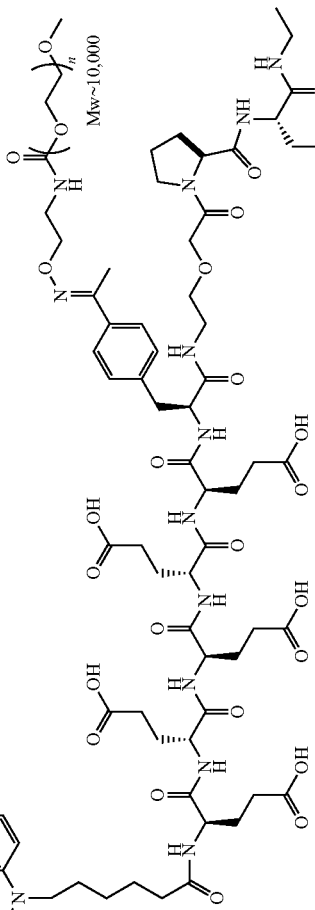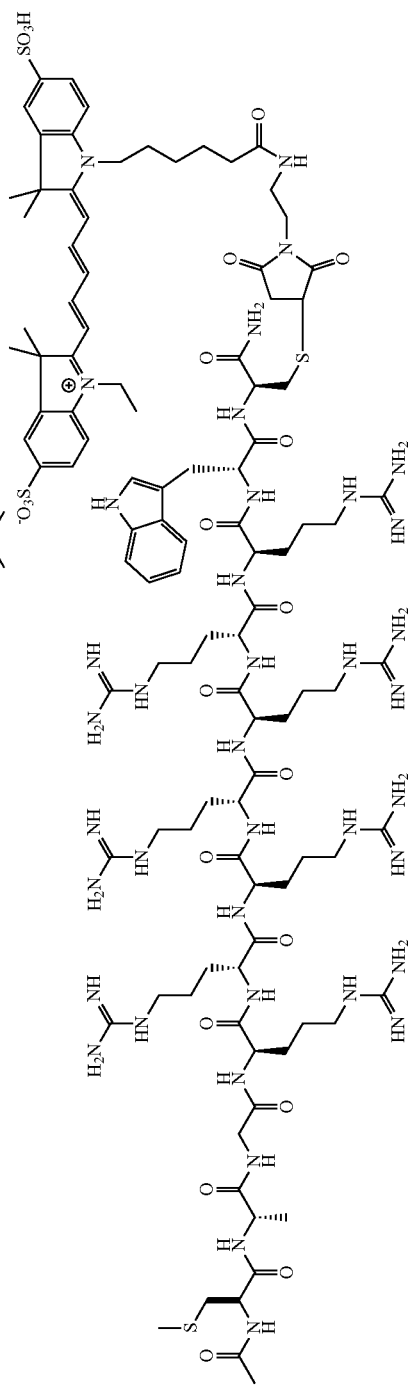 |

| | Chemical Structure |
|---|---|
| SDM-61 | |

| | Chemical Structure |
|---|---|
| SDM-62 | 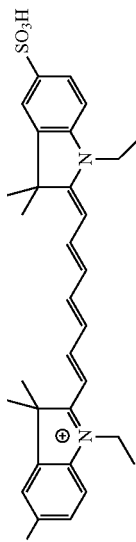 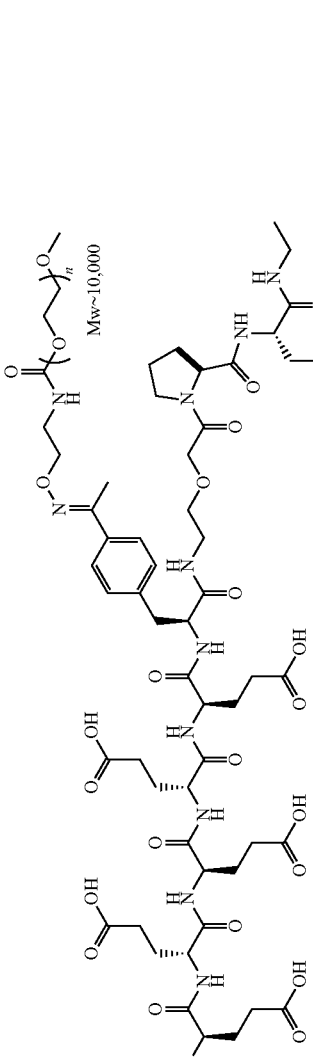 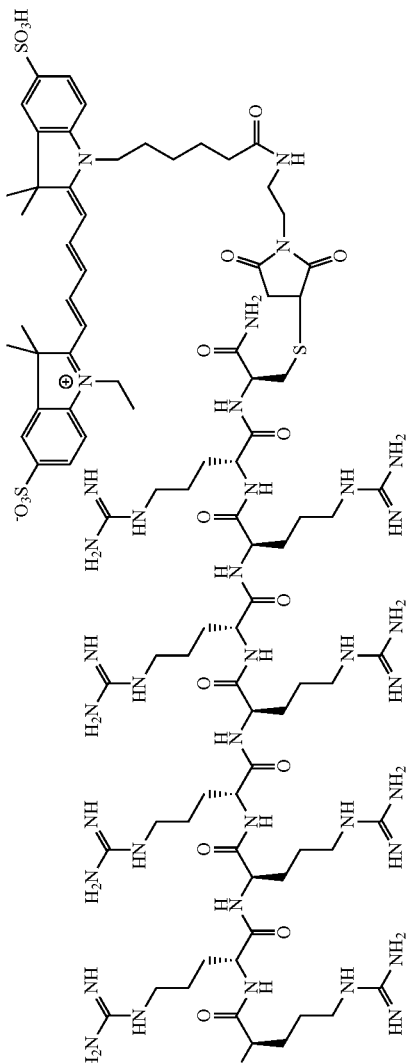 |

| | 73 | 74 |
|---|---|---|
| Chemical Structure | 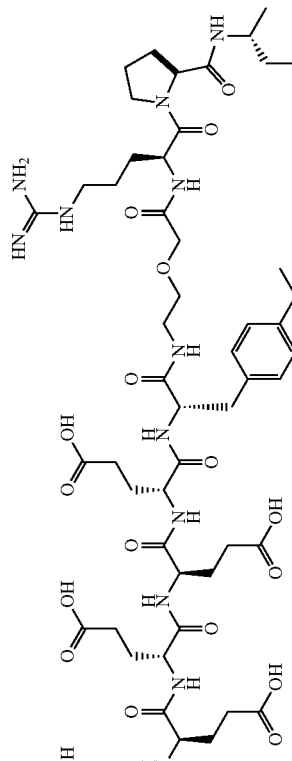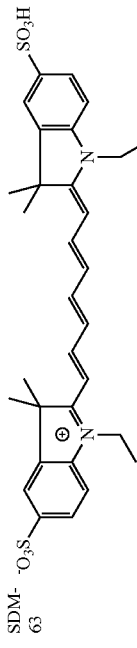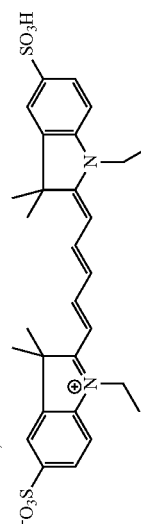 | 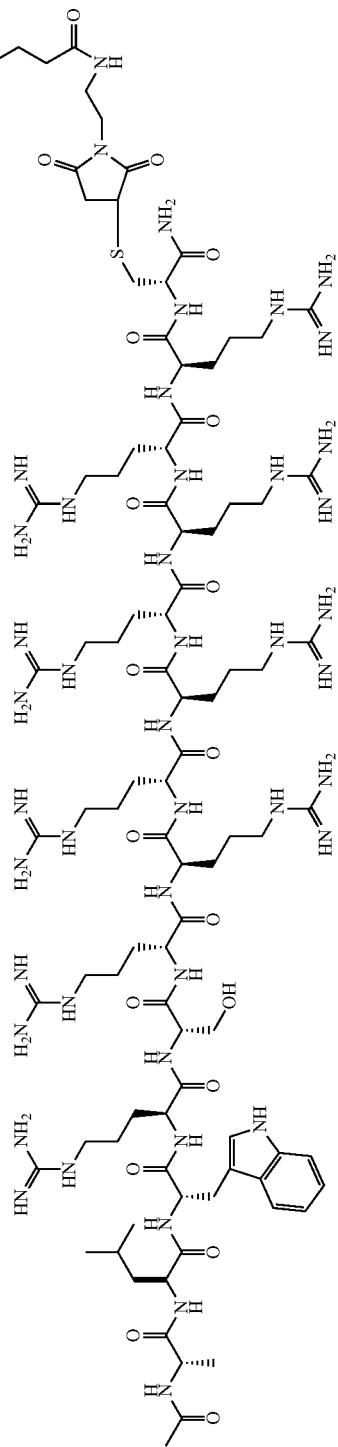 |
| SDM-63 | | |

| Chemical Structure |
|---|
| SDM-64 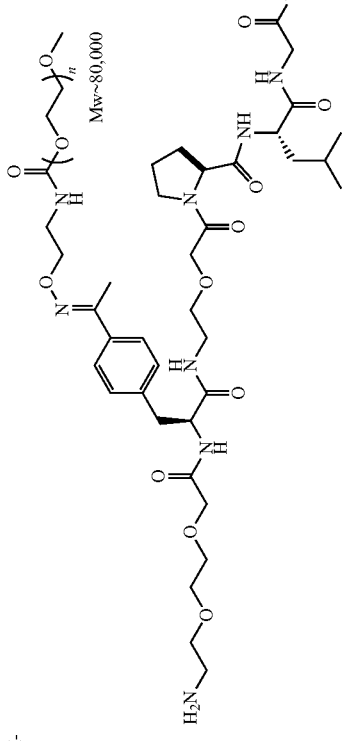 |

| | Chemical Structure |
|---|---|
| SDM-65 | 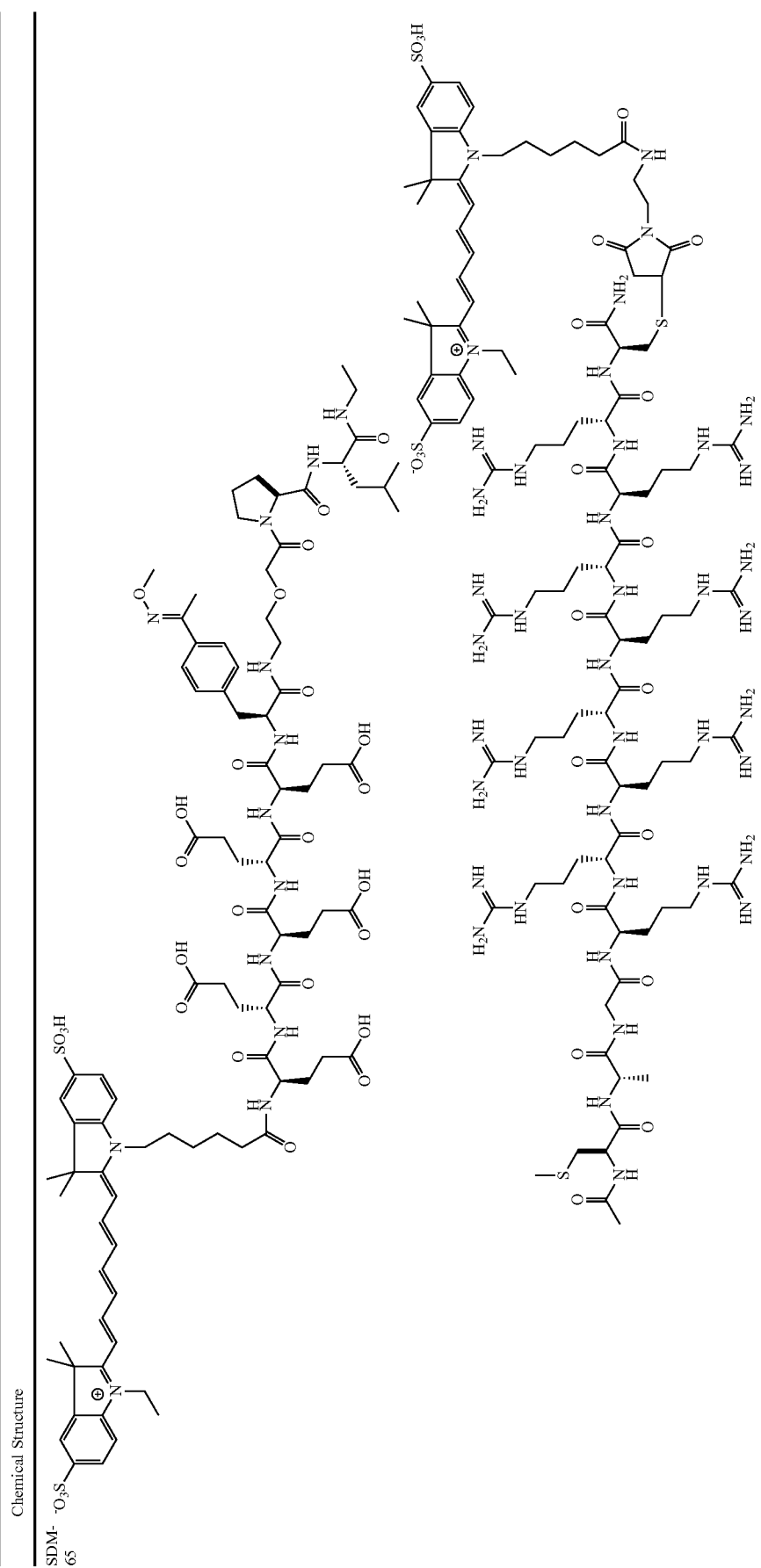 |

Further Modifications

In some embodiments, the targeting molecules of the present invention are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In some embodiments, the water-soluble polymer is dextran, polyethylene glycol (PEG), polyoxyalkylene, polysialic acid, starch, or hydroxyethyl starch. Any suitable method is used to conjugate peptides to water-soluble polymers (see Hermanson G., *Bioconjugate Techniques* 2$^{nd}$ Ed, Academic Press, Inc. 2008).

Pharmaceutical Compositions

Disclosed herein, in certain embodiments, are pharmaceutical compositions comprising a selective delivery molecule according to SDM-41. Disclosed herein, in certain embodiments, are pharmaceutical compositions comprising a selective delivery molecule according to SDM-42. Disclosed herein, in certain embodiments, are pharmaceutical compositions comprising a selective delivery molecule according to SDM-43. Disclosed herein, in certain embodiments, are pharmaceutical compositions comprising a selective delivery molecule according to SDM-44. Disclosed herein, in certain embodiments, are pharmaceutical compositions comprising a selective delivery molecule according to SDM-45. Disclosed herein, in certain embodiments, are pharmaceutical compositions comprising a selective delivery molecule according to SDM-46. Disclosed herein, in certain embodiments, are pharmaceutical compositions comprising a selective delivery molecule according to SDM-47. Disclosed herein, in certain embodiments, are pharmaceutical compositions comprising a selective delivery molecule according to SDM-48. Disclosed herein, in certain embodiments, are pharmaceutical compositions comprising a selective delivery molecule according to SDM-49. Disclosed herein, in certain embodiments, are pharmaceutical compositions comprising a selective delivery molecule according to SDM-50. Disclosed herein, in certain embodiments, are pharmaceutical compositions comprising a selective delivery molecule according to SDM-51. Disclosed herein, in certain embodiments, are pharmaceutical compositions comprising a selective delivery molecule according to SDM-52. Disclosed herein, in certain embodiments, are pharmaceutical compositions comprising a selective delivery molecule according to SDM-53. Disclosed herein, in certain embodiments, are pharmaceutical compositions comprising a selective delivery molecule according to SDM-54. Disclosed herein, in certain embodiments, are pharmaceutical compositions comprising a selective delivery molecule according to SDM-55. Disclosed herein, in certain embodiments, are pharmaceutical compositions comprising a selective delivery molecule according to SDM-56. Disclosed herein, in certain embodiments, are pharmaceutical compositions comprising a selective delivery molecule according to SDM-57. Disclosed herein, in certain embodiments, are pharmaceutical compositions comprising a selective delivery molecule according to SDM-58. Disclosed herein, in certain embodiments, are pharmaceutical compositions comprising a selective delivery molecule according to SDM-59. Disclosed herein, in certain embodiments, are pharmaceutical compositions comprising a selective delivery molecule according to SDM-60. Disclosed herein, in certain embodiments, are pharmaceutical compositions comprising a selective delivery molecule according to SDM-61. Disclosed herein, in certain embodiments, are pharmaceutical compositions comprising a selective delivery molecule according to SDM-62. Disclosed herein, in certain embodiments, are pharmaceutical compositions comprising a selective delivery molecule according to SDM-63. Disclosed herein, in certain embodiments, are pharmaceutical compositions comprising a selective delivery molecule according to SDM-64. Disclosed herein, in certain embodiments, are pharmaceutical compositions comprising a selective delivery molecule according to SDM-65.

Disclosed herein, in certain embodiments, are pharmaceutical compositions comprising a selective delivery molecule of Formula I, having the structure:

$$[c_M\text{-M}]\text{-}[[D_A\text{-}c_A]\text{-}(A\text{-}X\text{-}B)\text{-}[c_B\text{-}D_B]] \qquad \text{Formula I}$$

wherein,

X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acid;

M is a macromolecule carrier; and $D_A$ and $D_B$ are each independently selected from an imaging agent and a therapeutic; and wherein $[c_M\text{-M}]$ is bound at any position on or between A, X, and B, $[D_A\text{-}c_A]$ is bound to any amino acid on A or X, and $[c_B\text{-}D_B]$ is bound to any amino acid on B.

In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NOS: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ ID NOS: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence RLQLKL (SEQ ID NO: 11). In some embodiments, X comprises the amino acid sequence RLQLK(Ac) (SEQ ID NO: 12). In some embodiments, M is selected from a protein, a natural polymer, a synthetic polymer, or a dendrimer. In some embodiments, M is selected from dextran, PEG polymers, albumin, or a combination thereof. In some embodiments, M is PEG polymers. In some embodiments, M is selected from PEG polymers having an average molecular weight of approximately 0.5 kDa (PEG 0.5 kDa), PEG polymers having an average molecular weight of approximately 2 kDa (PEG 2 kDa), PEG polymers having an average molecular weight of approximately 5 kDa (PEG 5 kDa), PEG polymers having an average molecular weight of approximately 12 kDa (PEG 12 kDa), PEG polymers having an average molecular weight of approximately 20 kDa (PEG 20 kDa), PEG polymers having an average molecular weight of approximately 30 kDa (PEG 30 kDa), and PEG polymers having an average molecular weight of approximately 40 kDa (PEG40 kDa). In some embodiments, $D_A$ and $D_B$ are a pair of acceptor and donor fluorescent moieties that are capable of undergoing Forsters/fluorescence resonance energy transfer with the other. In some embodiments, $D_A$ and $D_B$ are indocarbocyanine dyes. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the molecule of Formula I is SDM-42.

Disclosed herein, in certain embodiments, are pharmaceutical compositions comprising a selective delivery molecule of Formula I, having the structure:

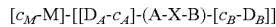

$[c_M\text{-M}]\text{-}[[D_A\text{-}c_A]\text{-}(A\text{-}X\text{-}B)\text{-}[c_B\text{-}D_B]]$   Formula I wherein, X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acids;

M is a polyethylene glycol (PEG) polymer; and $D_A$ and $D_B$ are each independently an imaging agent; and wherein $[c_M\text{-M}]$ is bound to at any position on A or X, [DA-cA] is bound to any amino acid on A or X, and $[c_B\text{-}D_B]$ is bound to any amino acid on B.

In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NO: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ ID NO: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG(SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence PPRSFL (SEQ ID NO: 10). In some embodiments, X comprises the amino acid sequence RLQLKL (SEQ ID NO: 11). In some embodiments, X comprises the amino acid sequence RLQLK(Ac) (SEQ ID NO: 12). In some embodiments, $D_A$ and $D_B$ are a pair of acceptor and donor fluorescent moieties that are capable of undergoing Forsters/fluorescence resonance energy transfer with the other. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the molecule of Formula I is SDM-42.

Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, peritumoral, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

Methods of Use

Selective delivery molecules SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65 allow the targeted delivery of cargo to specific cells and/or tissues.

Disclosed herein, in certain embodiments, are methods of delivering a cargo to a tissue of interest, comprising contacting the tissue of interest with a molecule selected from SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41.

Disclosed herein, in certain embodiments, are methods of delivering a cargo to a tissue of interest, comprising contacting the tissue of interest with a molecule of Formula I:

$$[c_M\text{-M}]\text{-}[[D_A\text{-}c_A]\text{-}(A\text{-}X\text{-}B)\text{-}[c_B\text{-}D_B]] \quad \text{Formula I}$$

wherein,

X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acid;

M is a macromolecule carrier; and $D_A$ and $D_B$ are each independently selected from an imaging agent and a therapeutic; and wherein $[c_M\text{-M}]$ is bound at any position on or between A, X, and B, $[D_A\text{-}c_A]$ is bound to any amino acid on A or X, and $[c_B\text{-}D_B]$ is bound to any amino acid on B. In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NOS: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ ID NOS: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ IDNO:1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence RLQLKL (SEQ ID NO: 11). In some embodiments, X comprises the amino acid sequence RLQLK(Ac) (SEQ ID NO: 12). In some embodiments, M is selected from a protein, a natural polymer, a synthetic polymer, or a dendrimer. In some embodiments, M is selected from dextran, PEG polymers, albumin, or a combination thereof. In some embodiments, M is PEG polymers. In some embodiments, M is selected from PEG polymers having an average molecular weight of approximately 0.5 kDa (PEG 0.5 kDa), PEG polymers having an average molecular weight of approximately 2 kDa (PEG 2 kDa), PEG polymers having an average molecular weight of approximately 5 kDa (PEG 5 kDa), PEG polymers having an average molecular weight of approximately 12 kDa (PEG 12 kDa), PEG polymers having an average molecular weight of approximately 20 kDa (PEG 20 kDa), PEG polymers having an average molecular weight of approximately 30 kDa (PEG 30 kDa), and PEG polymers having an average molecular weight of approximately 40 kDa (PEG40 kDa). In some embodiments, $D_A$ and $D_B$ are a pair of donor and acceptor fluorescent moieties that are capable of undergoing Forsters/fluorescence resonance energy transfer with the other. In some embodiments, $D_A$ and $D_B$ are indocarbocyanine dyes. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the molecule of Formula I is SDM-42.

Tissue of Interest

In some embodiments, the tissue of interest is casncerous tissue (or, cancer). In some embodiments, the cancerous tissue is: breast cancer tissue, colorectal cancer tissue, squamous cell carcinoma tissue, skin cancer tissue, prostate cancer tissue, melanoma tissue, ovarian cancer tissue, cancerous lymph node tissue, or thyroid cancer tissue. In some embodiments, the cancerous tissue is breast cancer tissue. In some embodiments, the cancerous tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue.

In some embodiments, the cancer is AIDS-related cancers (e.g., AIDS-related lymphoma), anal cancer, basal cell carcinoma, bile duct cancer (e.g., extrahepatic), bladder cancer, bone cancer, (osteosarcoma and malignant fibrous histiocytoma), breast cancer, cervical cancer, colorectal cancer, endometrial cancer (e.g., uterine cancer), ependymoma, esophageal cancer, eye cancer (e.g., intraocular melanoma and retinoblastoma), gastric (stomach) cancer, germ cell tumor, (e.g., extracranial, extragonadal, ovarian), head and neck cancer, leukemia, lip and oral cavity cancer, liver cancer, lung cancer (e.g., small cell lung cancer, non-small cell lung cancer, adenocarcinoma of the lung, and squamous carcinoma of the lung), ovarian cancer, pancreatic cancer, pituitary tumor, prostate cancer, renal cancer, skin cancer, small intestine cancer, squamous cell cancer, testicular cancer, throat cancer, thyroid cancer, urethral cancer, and post-transplant lymphoproliferative disorder (PTLD).

In some embodiments, the cancer is a lymphoid cancer (e.g., lymphoma).

In some embodiments, the cancer is a B-cell cancer. In some embodiments, the cancer is precursor B-cell cancers (e.g., precursor B-lymphoblastic leukemia/lymphoma) and peripheral B-cell cancers (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type +/− monocytoid B cells) and/or Nodal (e.g., +/− monocytoid B cells)), splenic marginal zone lymphoma (e.g., +/− villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments, the cancer is a T-cell and/or putative NK-cell cancer. In some embodiments, the cancer is precursor T-cell cancer (precursor T-lymphoblastic lymphoma/leukemia) and peripheral T-cell and NK-cell cancers (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/− enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like).

In some embodiments, the cancer is Hodgkin's disease.

In some embodiments, the cancer is leukemia. In some embodiments, the cancer is chronic myelocytic I (granulocytic) leukemia, chronic myelogenous, and chronic lymphocytic leukemia (CLL), acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is a liquid tumor or plasmacytoma. In some embodiments, the cancer is extramedullary plasmacytoma, a solitary myeloma, and multiple myeloma. In some embodiments, the plasmacytoma is multiple myeloma.

In some embodiments, the cancer is lung cancer.

In some embodiments, the cancer is prostate cancer. In some embodiments, the prostate cancer is an adenocarcinoma. In some embodiments, the prostate cancer is a sarcoma, neuroendocrine tumor, small cell cancer, ductal cancer, or a lymphoma. In some embodiments, the prostate cancer is stage A prostate cancer (the cancer cannot be felt during a rectal exam). In some embodiments, the prostate cancer is stage B prostate cancer (i.e., the tumor involves more tissue within the prostate, it can be felt during a rectal exam, or it is found with a biopsy that is done because of a high PSA level). In some embodiments, the prostate cancer is stage C prostate cancer (i.e., the cancer has spread outside the prostate to nearby tissues). In some embodiments, the prostate cancer is stage D prostate cancer. In some embodiments, the prostate cancer is androgen independent prostate cancer (AIPC). In some embodiments, the prostate cancer is androgen dependent prostate cancer. In some embodiments, the prostate cancer is refractory to hormone therapy. In some embodiments, the prostate cancer is substantially refractory to hormone therapy. In some embodiments, the prostate cancer is refractory to chemotherapy. In some embodiments, the prostate cancer is metastatic prostate cancer. In some embodiments, the individual is a human who has a gene, genetic mutation, or polymorphism associated with prostate cancer (e.g., RNASEL/HPC1, ELAC2/HPC2, SR-A/MSR1, CHEK2, BRCA2, PON1, OGG1, MIC-1, TLR4, and PTEN) or has one or more extra copies of a gene associated with prostate cancer. In some embodiments, the prostate cancer is HER2 positive. In some embodiments, the prostate cancer is HER2 negative.

In some embodiments, the cancer has metastasized and is characterized by circulating tumor cells.

Imaging Uses

The selective delivery molecules SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, and SDM-65 allow the targeted delivery of imaging agents to specific cells and/or tissues (e.g., cancerous tissues). In some embodiments, the selective delivery molecules enable targeted delivery of one or more imaging agents to a cell or tissue. In some embodiments, targeted delivery of an imaging agent to a cell or tissue enables a medical professional to visualize/image a specific tissue.

Disclosed herein, in certain embodiments, are methods of delivering imaging agents to a tissue of interest, comprising contacting the tissue of interest with a molecule selected from the group consisting of: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, and SDM-65. In some embodiments, the molecule is SDM-41.

Disclosed herein, in certain embodiments, are methods of delivering imaging agents to a tissue of interest, comprising contacting the tissue of interest with a molecule of Formula I:

$$[c_M\text{-M}]\text{-}[[D_A\text{-}c_A]\text{-}(A\text{-}X\text{-}B)\text{-}[c_B\text{-}D_B]] \qquad \text{Formula I}$$

wherein,

X is a peptide linker cleavable by a matrix metalloproteinase;

A is a peptide with a sequence comprising 5 or 9 consecutive glutamates (SEQ ID NOS: 4-5, respectively);

B is a peptide with a sequence comprising 8 or 9 consecutive arginines (SEQ ID NOS: 6-7, respectively);

$c_A$, $c_B$, and $c_M$ are independently 0-1 amino acid;

M is a polyethylene glycol (PEG) polymer; and $D_A$ and $D_B$ are each independently an imaging agent; and wherein [$c_M$-M] is bound to at any position on A or X, [DA-cA] is bound to any amino acid on A or X, and [$c_B$-$D_B$] is bound to any amino acid on B.

In some embodiments, A and B do not have an equal number of acidic and basic amino acids. In some embodiments, $c_A$, $c_B$, and $c_M$ are each independently a 0-1 amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence PPRSFL (SEQ ID NO: 10). In some embodiments, X comprises the amino acid sequence RLQLKL (SEQ ID NO: 11). In some embodiments, X comprises the amino acid sequence RLQLK(Ac) (SEQ ID NO: 12). In some embodiments, $D_A$ and $D_B$ are a pair of acceptor and donor fluorescent moieties that are capable of undergoing Forsters/fluorescence resonance energy transfer with the other. In some embodiments, $D_A$ and $D_B$ are indocarbocyanine dyes. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with a molecule of Formula I:

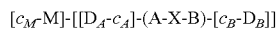

Formula I wherein,

X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acid;

M is a polyethylene glycol (PEG) polymer; and $D_A$ and $D_B$ are a pair of acceptor and donor fluorescent moieties that are capable of undergoing Forsters/fluorescence resonance energy transfer with the other; and wherein [$c_M$-M] is bound to at any position on A or X, [DA-cA] is bound to any amino acid on A or X, and [$c_B$-$D_B$] is bound to any amino acid on B. In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NOS: 4-5, respectively). In some embodiments, B is a peptide comprising 8 or 9 consecutive arginines (SEQ ID NOS: 6-7, respectively). In some embodiments, A is a peptide comprising 5 or 9 consecutive glutamates (SEQ ID NOS: 4-5, respectively) and B is a peptide comprising 8 or 9 consecutive arginines (SEQ IDNOS: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence PPRSFL (SEQ ID NO: 10). In some embodiments, X comprises the amino acid sequence RLQLKL (SEQ ID NO: 11). In some embodiments, X comprises the amino acid sequence RLQLK(Ac) (SEQ ID NO: 12). In some embodiments, $D_A$ and $D_B$ are a pair of acceptor and donor fluorescent moieties that are capable of undergoing Forsters/fluorescence resonance energy transfer with the other. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the molecule of Formula I is SDM-42.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-41.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-42.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-43.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-44.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-45.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-46.

Disclosed herein, in certain embodiments, are methods of delivering a pair of acceptor and donor fluorescent moieties that are capable of undergoing Forsters/fluorescence resonance energy transfer with the other o to a tissue of interest, comprising contacting the tissue of interest with SDM-47.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-48.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-49.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-50.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-51.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-52.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-53.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-54.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-55.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-56.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-57.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-58.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-59.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-60.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-61.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-62.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-63.

Disclosed herein, in certain embodiments, are methods of delivering a pair of donor and acceptor fluorescent moieties that are capable of undergoing Forsters/fluorescence resonance energy transfer with the other to a tissue of interest, comprising contacting the tissue of interest with SDM-64.

Disclosed herein, in certain embodiments, are methods of delivering a pair of acceptor and donor fluorescent moieties that are capable of undergoing Forsters/fluorescence resonance energy transfer with the other to a tissue of interest, comprising contacting the tissue of interest with SDM-65.

Disclosed herein, in certain embodiments, are methods of visualizing a tissue of interest in an individual in need thereof, comprising: (a) administering to the individual a molecule selected from SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65; and (b) visualizing at least one of the imaging agents.

Disclosed herein, in certain embodiments, are methods of visualizing a tissue of interest in an individual in need thereof, comprising:

(a) administering to the individual a molecule of Formula I that localizes to the tissue of interest in the individual, $$[c_M\text{-}M]\text{-}[[D_A\text{-}c_A]\text{-}(A\text{-}X\text{-}B)\text{-}[c_B\text{-}D_B]] \quad \text{Formula I}$$

wherein,

X is a cleavable linker;

A is a peptide with a sequence comprising 5 to 9 acidic amino acids;

B is a peptide with a sequence comprising 7 to 9 basic amino acids;

$c_A$, $c_B$, and $c_M$ are independently 0-1 amino acid;

M is a polyethylene glycol (PEG) polymer; and $D_A$ and $D_B$ are each independently an imaging agent; and wherein $[c_M\text{-}M]$ is bound at any position on or between A, X, and B, $[D_A\text{-}c_A]$ is bound to any amino acid on A or X, and $[c_B\text{-}D_B]$ is bound to any amino acid on B; and (b) visualizing at least one of the imaging agents.

In some embodiments, the tissue is cancerous. In some embodiments, the cancerous tissue is: breast cancer tissue, colorectal cancer tissue, squamous cell carcinoma tissue, skin cancer tissue, prostate cancer tissue, melanoma tissue, thyroid cancer tissue, ovarian cancer tissue, or cancerous lymph node tissue. In some embodiments, the cancerous cell or tissue is breast cancer tissue. In some embodiments, the cancerous cell or tissue is colorectal cancer tissue. In some embodiments, the cancerous tissue is cancerous lymph node tissue. In some embodiments, the cancerous tissue is squamous cell carcinoma tissue. In some embodiments, the cancerous tissue is skin cancer tissue. In some embodiments, the method further comprises surgically removing the tissue of interest from the individual. In some embodiments, the surgical margin surrounding the tissue of interest is decreased. In some embodiments, the method further comprises preparing a tissue sample from the removed cell or tissue of interest. In some embodiments, the method further comprises staging the cancerous tissue. In some embodiments, A and B do not have an equal number of acidic and basic amino acids. In some embodiments, the number of basic amino acids in B is greater than the number of acidic amino acids in A. In some embodiments, A is a peptide comprising 5 or 9 consecutive glutamates (SEQ ID NO: 4-5, respectively). In some embodiments, B is a peptide comprising 8 or 9 consecutive arginines (SEQ ID NO: 6-7, respectively). In some embodiments, A is a peptide comprising 5 or 9 consecutive glutamates (SEQ ID NO: 4-5, respectively) and B is a peptide comprising 8 or 9 consecutive arginines (SEQ ID NO: 6-7, respectively). In some embodiments, A is a peptide comprising 5 consecutive glutamates (SEQ ID NO: 4) and B is a peptide comprising 8 consecutive arginines (SEQ ID NO: 6). In some embodiments, $c_A$, $c_B$, and $c_M$ are each independently a 0-1 amino acid. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X is cleavable by a protease. In some embodiments, X is cleavable by a matrix metalloproteinase. In some embodiments, X comprises an amino acid sequence that is cleavable by MMP2, MMP7, MMP9, or MMP14. In some embodiments, X comprises a peptide linkage. In some embodiments, X comprises an amino acid sequence selected from: PLGLAG (SEQ ID NO: 2), PLG-C(me)-AG (SEQ ID NO: 1), RPLALWRS (SEQ ID NO: 3), ESPAYYTA (SEQ ID NO: 8), DPRSFL (SEQ ID NO: 9), PPRSFL (SEQ ID NO: 10), RLQLKL (SEQ ID NO: 11), and RLQLK(Ac) (SEQ ID NO: 12). In some embodiments, X comprises the amino acid sequence PLGLAG (SEQ ID NO: 2). In some embodiments, X comprises the amino acid sequence PLG-C(me)-AG (SEQ ID NO: 1). In some embodiments, X comprises the amino acid sequence RPLALWRS (SEQ ID NO: 3). In some embodiments, X comprises the amino acid sequence DPRSFL (SEQ ID NO: 9). In some embodiments, X comprises the amino acid sequence PPRSFL (SEQ ID NO: 10). In some embodiments, X comprises the amino acid sequence RLQLKL (SEQ ID NO: 11). In some embodiments, X comprises the amino acid sequence RLQLK(Ac) (SEQ ID NO: 12). In some embodiments, $D_A$ and $D_B$ are a pair of acceptor and donor fluorescent moieties that are capable of undergoing Försters/fluorescence resonance energy transfer with the other. In some embodiments, $D_A$ and $D_B$ are Cy5 and Cy7. In some embodiments, $D_A$ and $D_B$ are Cy5 and IRDye750. In some embodiments, $D_A$ and $D_B$ are Cy5 and IRDye800. In some embodiments, $D_A$ and $D_B$ are Cy5 and ICG. In some embodiments, the method further comprises visualizing Forsters/fluorescence resonance energy transfer between $D_A$ and $D_B$. In some embodiments, $D_A$ and $D_B$ are a fluorescent moiety and a fluorescence-quenching moiety. In some embodiments, the molecule of Formula I is: SDM-41, SDM-42, SDM-43, SDM-44, SDM-45, SDM-46, SDM-47, SDM-48, SDM-49, SDM-50, SDM-51, SDM-52, SDM-53, SDM-54, SDM-55, SDM-56, SDM-57, SDM-58, SDM-59, SDM-60, SDM-61, SDM-62, SDM-63, SDM-64, or SDM-65. In some embodiments, the molecule is SDM-41. In some embodiments, the molecule of Formula I is SDM-42.

Disclosed herein, in certain embodiments, are methods of visualizing a tissue of interest in an individual in need thereof, comprising, comprising (a) administering SDM-41 to the individual, and (b) visualizing at least one of the imaging agents.

Disclosed herein, in certain embodiments, are methods of visualizing a tissue of interest in an individual in need thereof, comprising, comprising (a) administering SDM-42 to the individual, and (b) visualizing at least one of the imaging agents.

Disclosed herein, in certain embodiments, are methods of visualizing a tissue of interest in an individual in need thereof, comprising, comprising (a) administering SDM-43 to the individual, and (b) visualizing at least one of the imaging agents.

Disclosed herein, in certain embodiments, are methods of visualizing a tissue of interest in an individual in need thereof, comprising, comprising (a) administering SDM-44 to the individual, and (b) visualizing at least one of the imaging agents.

Disclosed herein, in certain embodiments, are methods of visualizing a tissue of interest in an individual in need thereof, comprising, comprising (a) administering SDM-45 to the individual, and (b) visualizing at least one of the imaging agents.

Disclosed herein, in certain embodiments, are methods of visualizing a tissue of interest in an individual in need thereof, comprising, comprising (a) administering SDM-46 to the individual, and (b) visualizing at least one of the imaging agents.

Disclosed herein, in certain embodiments, are methods of visualizing a tissue of interest in an individual in need thereof, comprising, comprising (a) administering SDM-47 to the individual, and (b) visualizing at least one of the imaging agents.

Disclosed herein, in certain embodiments, are methods of visualizing a tissue of interest in an individual in need thereof, comprising, comprising (a) administering SDM-48 to the individual, and (b) visualizing at least one of the imaging agents.

Disclosed herein, in certain embodiments, are methods of visualizing a tissue of interest in an individual in need thereof, comprising, comprising (a) administering SDM-49 to the individual, and (b) visualizing at least one of the imaging agents.

Disclosed herein, in certain embodiments, are methods of visualizing a tissue of interest in an individual in need thereof, comprising, comprising (a) administering SDM-50 to the individual, and (b) visualizing at least one of the imaging agents.

Disclosed herein, in certain embodiments, are methods of visualizing a tissue of interest in an individual in need thereof, comprising, comprising (a) administering SDM-51 to the individual, and (b) visualizing at least one of the imaging agents.

Disclosed herein, in certain embodiments, are methods of visualizing a tissue of interest in an individual in need thereof, comprising, comprising (a) administering SDM-52 to the individual, and (b) visualizing at least one of the imaging agents.

Disclosed herein, in certain embodiments, are methods of visualizing a tissue of interest in an individual in need thereof, comprising, comprising (a) administering SDM-53 to the individual, and (b) visualizing at least one of the imaging agents.

Disclosed herein, in certain embodiments, are methods of visualizing a tissue of interest in an individual in need thereof, comprising, comprising (a) administering SDM-54 to the individual, and (b) visualizing at least one of the imaging agents.

Disclosed herein, in certain embodiments, are methods of visualizing a tissue of interest in an individual in need thereof, comprising, comprising (a) administering SDM-55 to the individual, and (b) visualizing at least one of the imaging agents.

Disclosed herein, in certain embodiments, are methods of visualizing a tissue of interest in an individual in need thereof, comprising, comprising (a) administering SDM-56 to the individual, and (b) visualizing at least one of the imaging agents.

Disclosed herein, in certain embodiments, are methods of visualizing a tissue of interest in an individual in need thereof, comprising, comprising (a) administering SDM-57 to the individual, and (b) visualizing at least one of the imaging agents.

Disclosed herein, in certain embodiments, are methods of visualizing a tissue of interest in an individual in need thereof, comprising, comprising (a) administering SDM-58 to the individual, and (b) visualizing at least one of the imaging agents.

Disclosed herein, in certain embodiments, are methods of visualizing a tissue of interest in an individual in need thereof, comprising, comprising (a) administering SDM-59 to the individual, and (b) visualizing at least one of the imaging agents.

Disclosed herein, in certain embodiments, are methods of visualizing a tissue of interest in an individual in need thereof, comprising, comprising (a) administering SDM-60 to the individual, and (b) visualizing at least one of the imaging agents.

Disclosed herein, in certain embodiments, are methods of visualizing a tissue of interest in an individual in need thereof, comprising, comprising (a) administering SDM-61 to the individual, and (b) visualizing at least one of the imaging agents.

Disclosed herein, in certain embodiments, are methods of visualizing a tissue of interest in an individual in need thereof, comprising, comprising (a) administering SDM-62 to the individual, and (b) visualizing at least one of the imaging agents.

Disclosed herein, in certain embodiments, are methods of visualizing a tissue of interest in an individual in need thereof, comprising, comprising (a) administering SDM-63 to the individual, and (b) visualizing at least one of the imaging agents.

Disclosed herein, in certain embodiments, are methods of visualizing a tissue of interest in an individual in need thereof, comprising, comprising (a) administering SDM-64 to the individual, and (b) visualizing at least one of the imaging agents.

Disclosed herein, in certain embodiments, are methods of visualizing a tissue of interest in an individual in need thereof, comprising, comprising (a) administering SDM-65 to the individual, and (b) visualizing at least one of the imaging agents.

In some embodiments, targeted delivery of an imaging agent to a cell or tissue enables a medical professional to visualize/image a specific tissue (e.g., cancerous tissue). In some embodiments, targeted delivery of an imaging agent to a cell or tissue enables a medical professional to remove (or, surgically excise) the tissue of interest (e.g., cancerous tissue). In some embodiments, targeted delivery of an imaging agent to a cell or tissue enables a medical professional to remove (or, surgically excise) the tissue of interest (e.g., cancerous tissue) with a decrease in surgical margins. In some embodiments, targeted delivery of an imaging agent to a cell or tissue enables a medical professional to remove (or, surgically excise) a tumor/cancerous tissue and decreases the chance that some of the tumor/cancerous tissue will not be removed. In some embodiments, targeted delivery of an imaging agent to a cell or tissue enables a medical professional to maximally debulk a tumor/cancerous tissue. In some embodiments, targeted delivery of an imaging agent to cancerous breast tissue decreases the chances of an unnecessary operations and re-operations.

In some embodiments, targeted delivery of an imaging agent to a cell or tissue enables a medical professional to more accurately sample (e.g., biopsy (e.g., excision biopsy, incision, biopsy, aspiration biopsy, or needle biopsy)) tissue of interest (e.g., cancerous tissue). In some embodiments, targeted delivery of an imaging agent to a cell or tissue enables a medical professional to visualize/image a specific tissue (e.g., cancerous tissue) within an excised tissue containing healthy tissue. Enabling identification of target tissue (e.g., cancerous tissue) can guide the pathologist on where to section for pathological evaluation and decreases the chances of a pathologist missing unhealthy tissue (e.g., cancerous tissue) and sampling healthy tissue which may produce a false negative. In some embodiments, tissue (e.g., cancerous tissue) removed following use of a compound of Formula I is used to prepare a pathology section or slide. In some embodiments, cancerous tissue removed following use of a compound of Formula I is used to prepare a pathology section or slide which is used to diagnose a tissue as malignant or benign.

In some embodiments, targeted delivery of an imaging agent to cancerous breast tissue enables a medical professional to accurately stage cancer enabling medical treatment decisions. In some embodiments, targeted delivery of an imaging agent to cancerous tissue enables a medical professional to observe the size of a tumor (cancerous tissue) or the spread (e.g., metastatic lesions) of cancerous tissue. In some embodiments, targeted delivery of an imaging agent to a cell or tissue enables a medical professional to design an efficacious treatment regimen.

In some embodiments, a selective delivery molecule according to Formula I comprising an imaging agent is employed in guided surgery. In some embodiments, the selective delivery molecule preferentially localized to cancerous, or other pathological tissues with up-regulated protease activity (e.g. tissues undergoing inflammatory response). In some embodiments, a selective delivery molecule according to Formula I comprising an imaging agent is employed in a guided surgery to remove colorectal cancer. In some embodiments, guided surgery employing the selective delivery molecule allows a surgeon to excise as little healthy (i.e., non-cancerous) tissue as possible. In some embodiments, guided surgery employing the selective delivery molecule allows a surgeon to visualize and excise more cancerous tissue than the surgeon would have been able to excise without the presence of the selective delivery molecule. In some embodiments, the surgery is fluorescence-guided surgery.

Imaging Agents

In some embodiments, an imaging agent is a dye. In some embodiments, an imaging agent is a fluorescent moiety. In some embodiments, a fluorescent moiety is selected from: a fluorescent protein, a fluorescent peptide, a fluorescent dye, a fluorescent material or a combination thereof.

All fluorescent moieties are encompassed within the term "fluorescent moiety." Specific examples of fluorescent moieties given herein are illustrative and are not meant to limit the fluorescent moieties for use with the targeting molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 5-carboxyfluorescein, fluorescein-5-isothiocyanate, fluorescein-6-isothiocyanate and 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

Examples of cyanine dyes include, but are not limited to, Cy3, Cy3B, Cy3.5, Cy5, Cy5.5, Cy7, IRDYE680, Alexa Fluor 750, IRDye800CW, ICG.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the imaging agent is labeled with a positron-emitting isotope (e.g., $^{18}$F) for positron emission tomography (PET), gamma-ray isotope (e.g., $^{99m}$Tc) for single photon emission computed tomography (SPECT), or a paramagnetic molecule or nanoparticle (e.g., $Gd^{3+}$ chelate or coated magnetite nanoparticle) for magnetic resonance imaging (MRI).

In some embodiments, the imaging agent is labeled with: a gadolinium chelate, an iron oxide particle, a super paramagnetic iron oxide particle, an ultra small paramagnetic particle, a manganese chelate or gallium containing agent.

Examples of gadolinium chelates include, but are not limited to diethylene triamine pentaacetic acid (DTPA), 1,4,7,10-tetraazacyclododecane-1,4,7,10-tetraacetic acid (DOTA), and 1,4,7-triazacyclononane-N,N',N"-triacetic acid (NOTA).

In some embodiments, the imaging agent is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, the imaging agent is a nuclear probe. In some embodiments, the imaging agent is a SPECT or PET radionuclide probe. In some embodiments, the radionuclide probe is selected from: a technetium chelate, a copper chelate, a radioactive fluorine, a radioactive iodine, a indiuim chelate.

Examples of Tc chelates include, but are not limited to HYNIC, DTPA, and DOTA.

In some embodiments, the imaging agent contains a radioactive moiety, for example a radioactive isotope such as 211At, $^{131}$I, $^{125}$I, $^{90}$Y, $^{186}$Re, $^{188}$Re, $^{153}$Sm, $^{212}$Bi, $^{32}$P, $^{64}$Cu radioactive isotopes of Lu, and others.

Starting Materials

Disclosed herein, in certain embodiments, are molecules of Formula II, having the structure:

$A_1$-$X_1$-$B_1$;  Formula II wherein, $X_1$ is a cleavable linker;

$A_1$ is a peptide with a sequence comprising 5 to 9 acidic amino acids and having a first reactive amino acid moiety $c_A$;

$B_1$ is a peptide with a sequence comprising 7 to 9 basic amino acids and having a second reactive amino acid moiety $c_B$; and $A_1$-$X_1$-$B_1$ has a third reactive amino acid moiety $c_M$ on $A_1$ or $X_1$; and wherein $c_A$ is capable of reacting with a first cargo moiety comprising $D_A$, $C_B$ is capable of reacting with a second cargo moiety comprising $D_B$, and $c_M$ is capable of reacting with a macromolecular carrier comprising M to form a molecule of Formula I.

In some embodiments, the $c_A$, $c_B$, and $c_M$ have functional groups that are orthogonally reactive. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently selected from any amino acid having a free thiol group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine.

As used herein, "orthogonally reactive" means a plurality of groups can be attached to a molecule via a sequence of reactions that do not cross react enabling specific attachment of each group in the presence of the others. In some embodiments, the three groups ($D_A$, $D_B$, and $D_M$) are able to be attached to $A_1$-$X_1$-$B_1$ via $c_A$, $c_B$, and $c_M$ using a sequence of 3 independent reactions that do not cross react so that each group is attached to only one site on $A_1$-$X_1$-$B_1$.

Disclosed herein, in certain embodiments, is a molecule having the amino acid sequence:

(D-Glu)$_5$-F(4-Ac)-o-Pro-Leu-Gly-Cys$_{(Me)}$-Ala-Gly-(D-Arg)$_8$-(D-Cys)

wherein o represent 5-(amino-3-oxapentanoyl); $F_{(4-Ac)}$ representpara-acetyl-(L)-phenylalanine; and $C_{(Me)}$ represents S-methyl-(L)-cysteine.

In some embodiments, the molecule further comprises a polyethylene glycol (PEG) polymer. In some embodiments, the PEG polymer is covalently linked to the molecule at the F(4-Ac) subunit. In some embodiments, the molecule comprises groups that can be orthogonally reacted. In some embodiments, the groups that can be orthogonally reacted are chosen from: an amine, thiol and an acetyl phenylalanine. In some embodiments, the molecule comprises an amine, a thiol, and an acetyl phenylalanine.

In some embodiments, the PEG polymer has an average molecular weight of approximately 0.5 kDa. In some embodiments, the PEG polymer has an average molecular weight of approximately 2 kDa. In some embodiments, the PEG polymer has an average molecular weight of approximately 5 kDa. In some embodiments, the PEG polymer has an average molecular weight of approximately 10 kDa. In some embodiments, the PEG polymer has an average molecular weight of approximately 20 kDa. In some embodiments, the PEG polymer has an average molecular weight of approximately 40 kDa. Disclosed herein, in certain embodiments, is the use of the molecule in the synthesis of a molecule according to Formula I.

Disclosed herein, in certain embodiments, is a molecule having the amino acid sequence:

(D-Glu)$_5$-o-Pro-Leu-Glys-Cys$_{(me)}$-Ala-Gly-(D-Arg)$_8$-(D-Cys)-[PEG$_{(2k)}$]

wherein all glutamates and arginines are D-amino acids; o represents 5-(amino-3-oxapentanoyl); Cys$_{(me)}$ represents S-methyl-(L)-cysteine; and PEG$_{(2k)}$ represents α-amino-ω-amide poly(ethylene glycol) with an average molecular weight of approximately two kDa. In some embodiments, the molecule further comprises a fluorescent moiety. Disclosed herein, in certain embodiments, is the use of the molecule in the synthesis of a molecule according to Formula I.

Peptide P-1

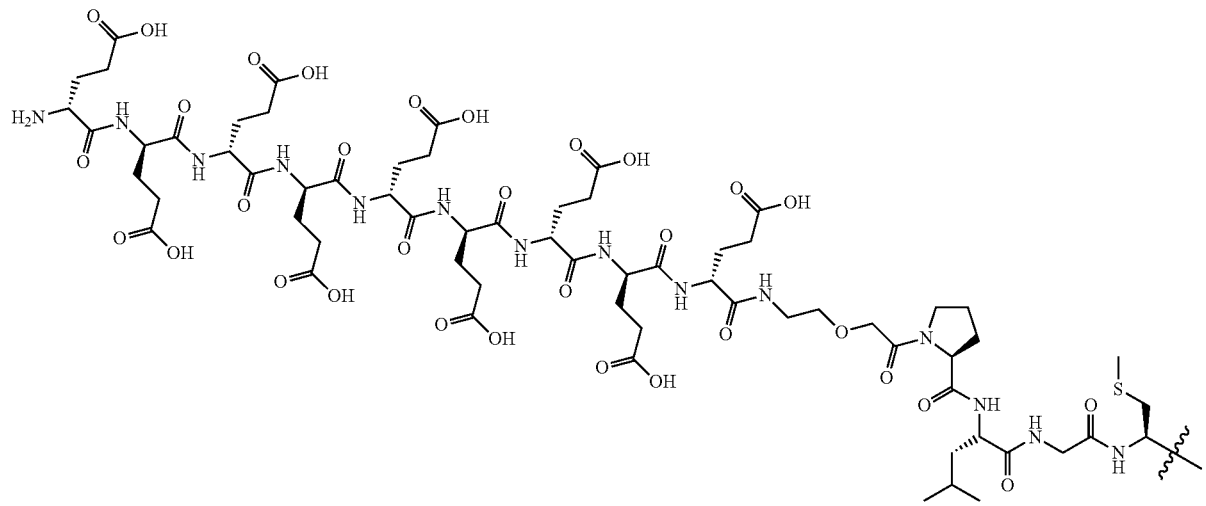

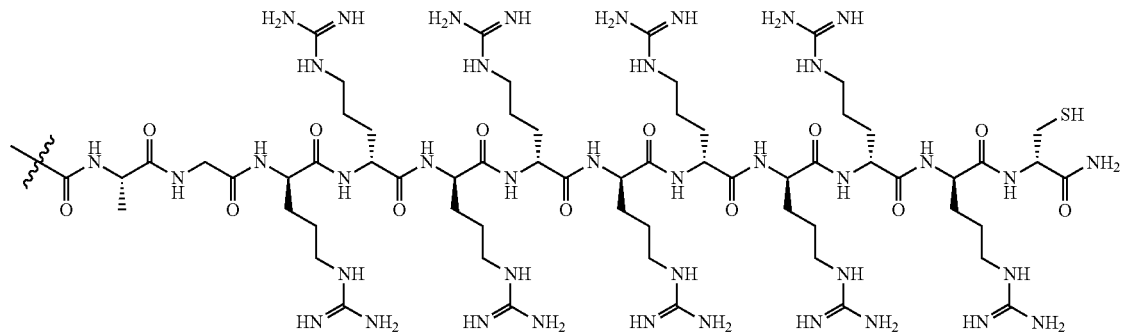

Peptide P-2
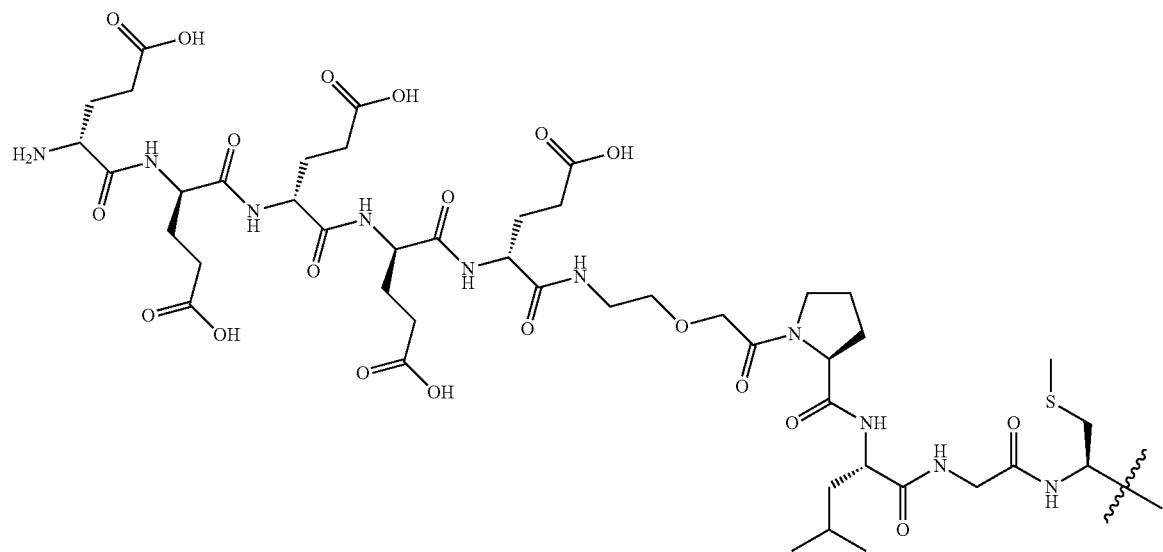
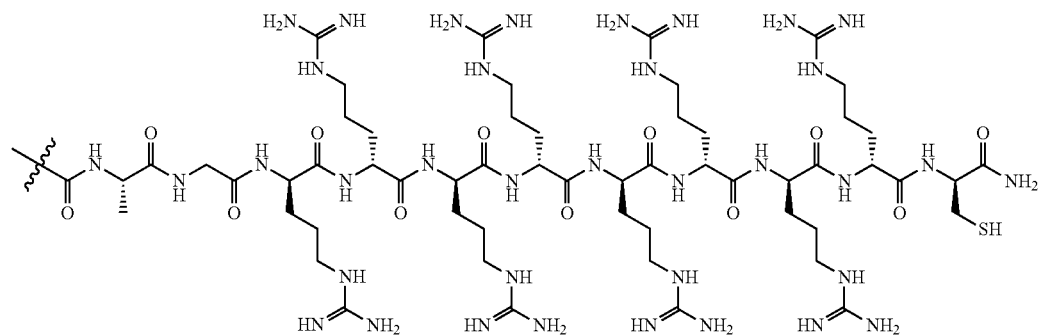
Peptide P-3
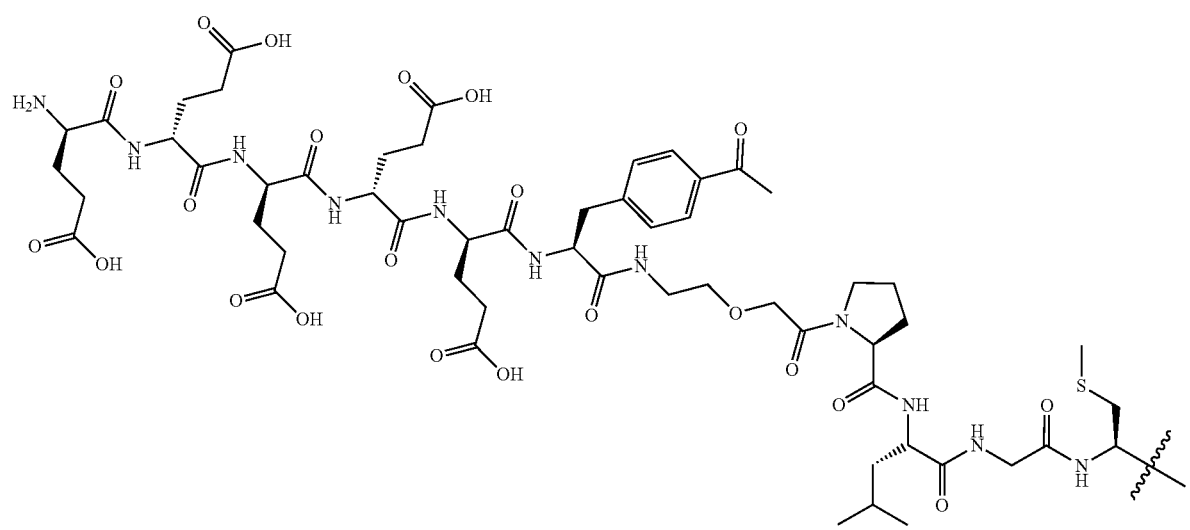

-continued
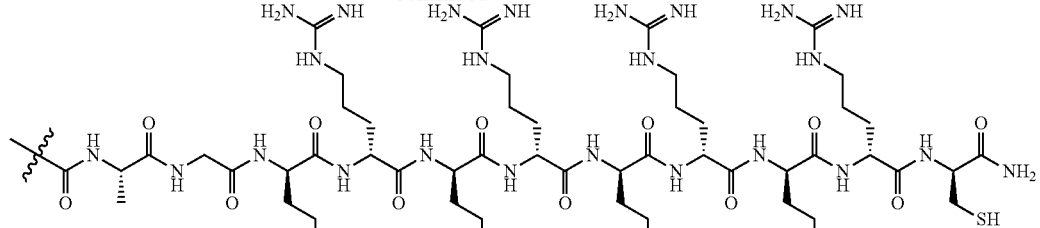
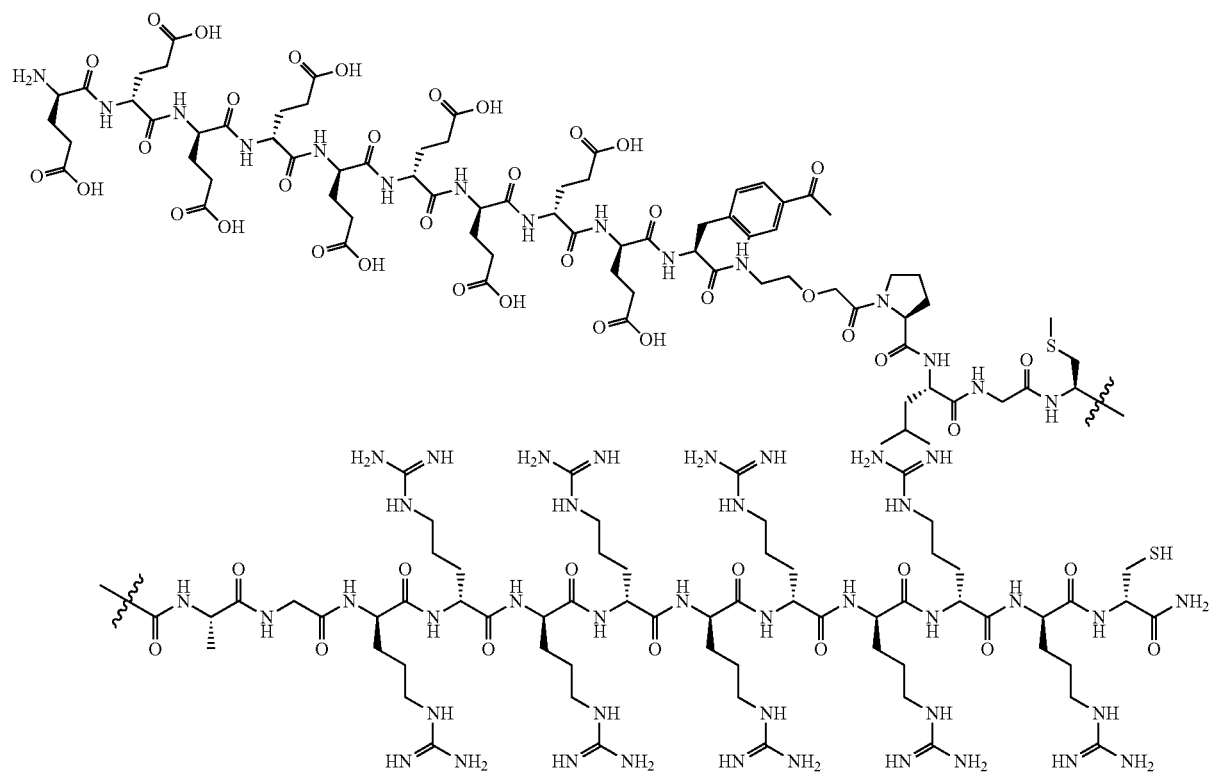
Peptide P-4
Peptide P-5
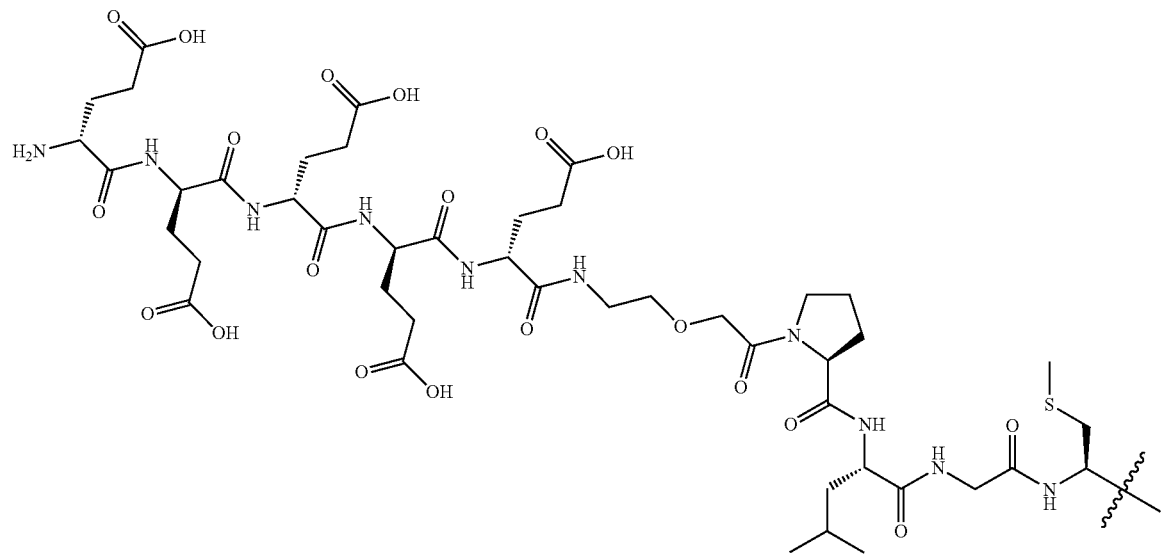

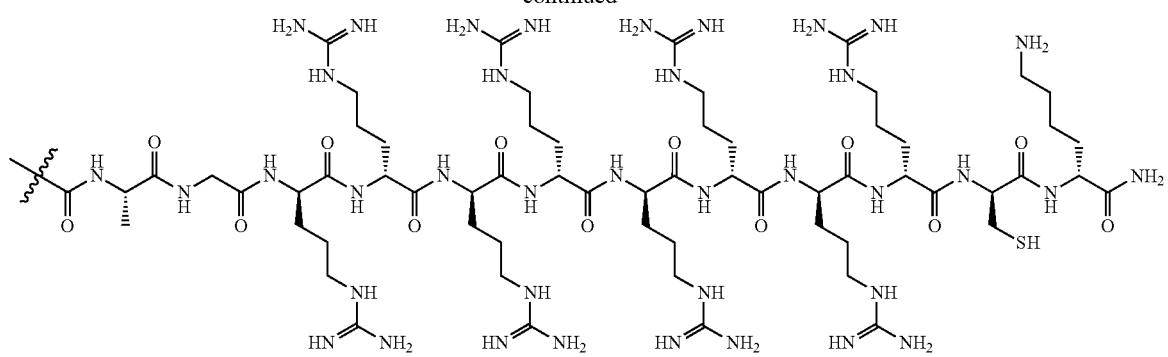
Peptide P-6
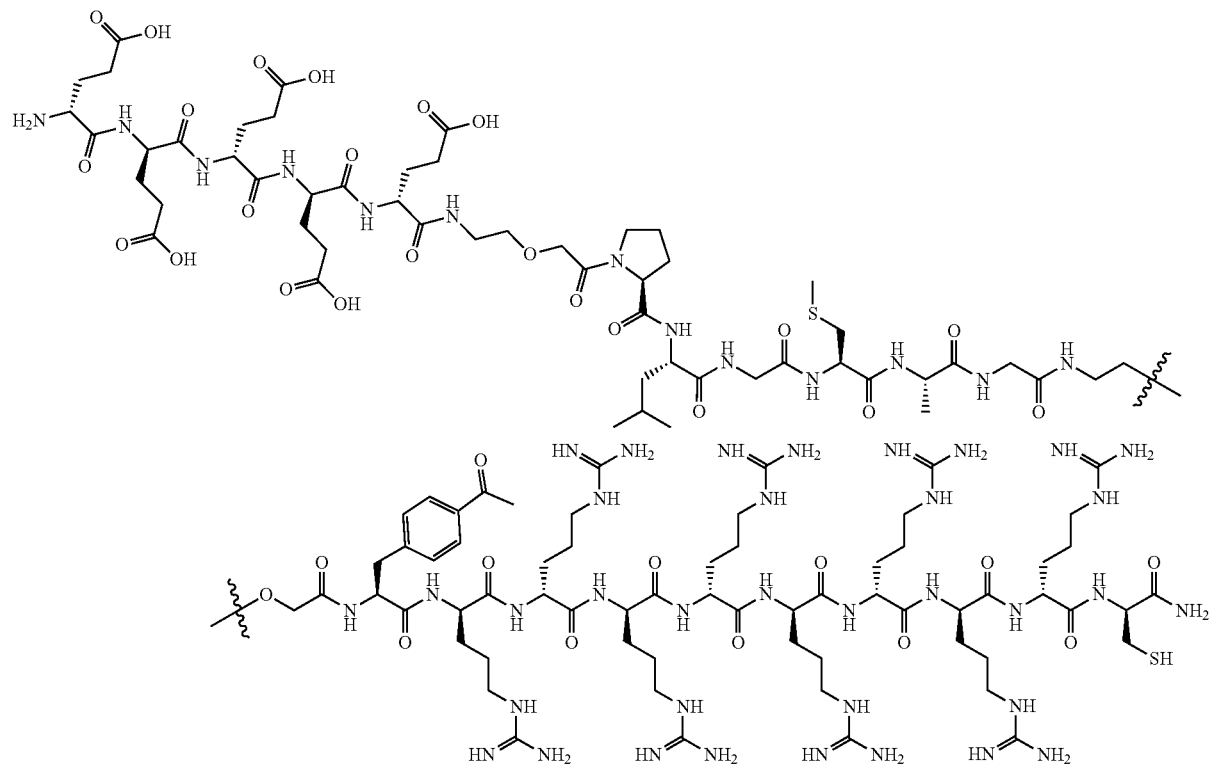
Peptide P-7
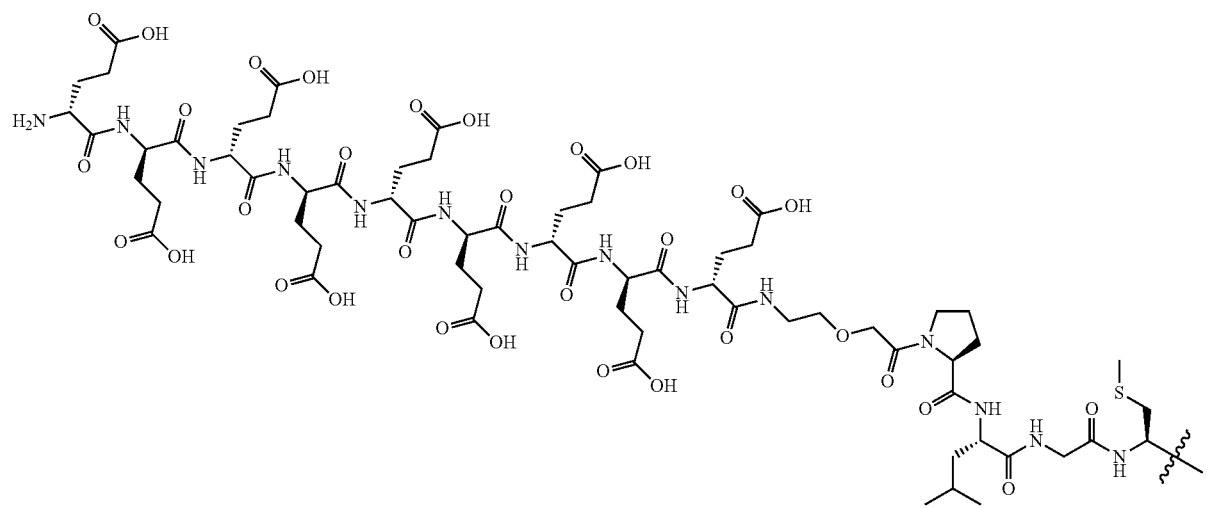

-continued
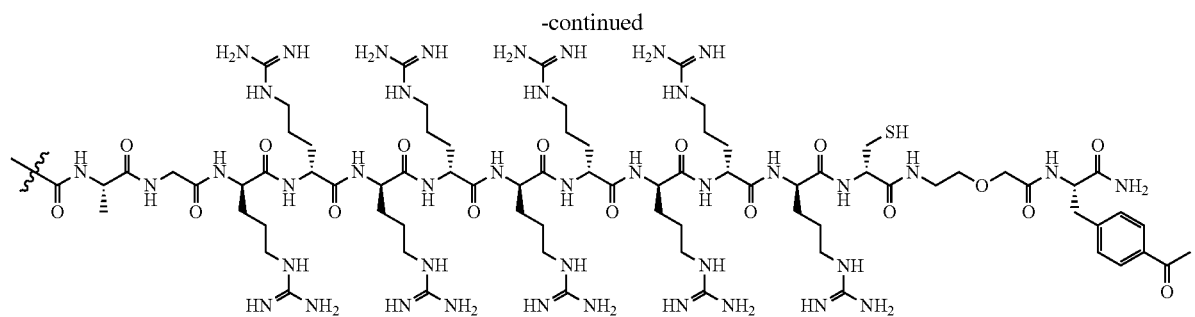
Peptide P-8
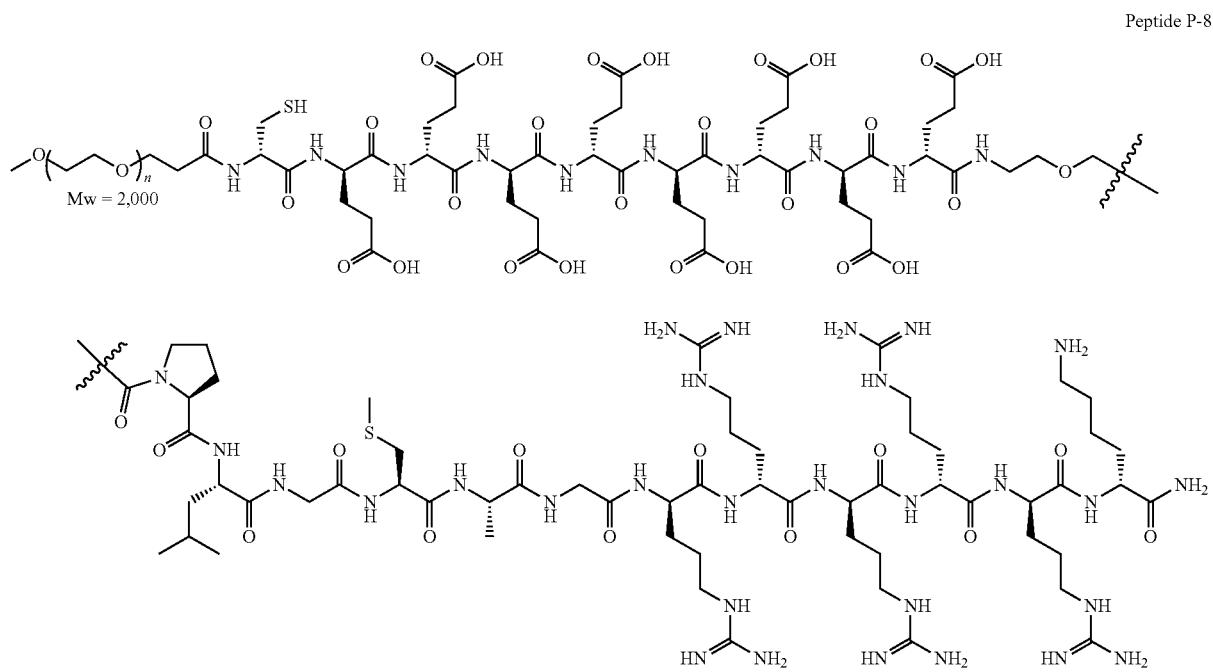
Peptide P-9
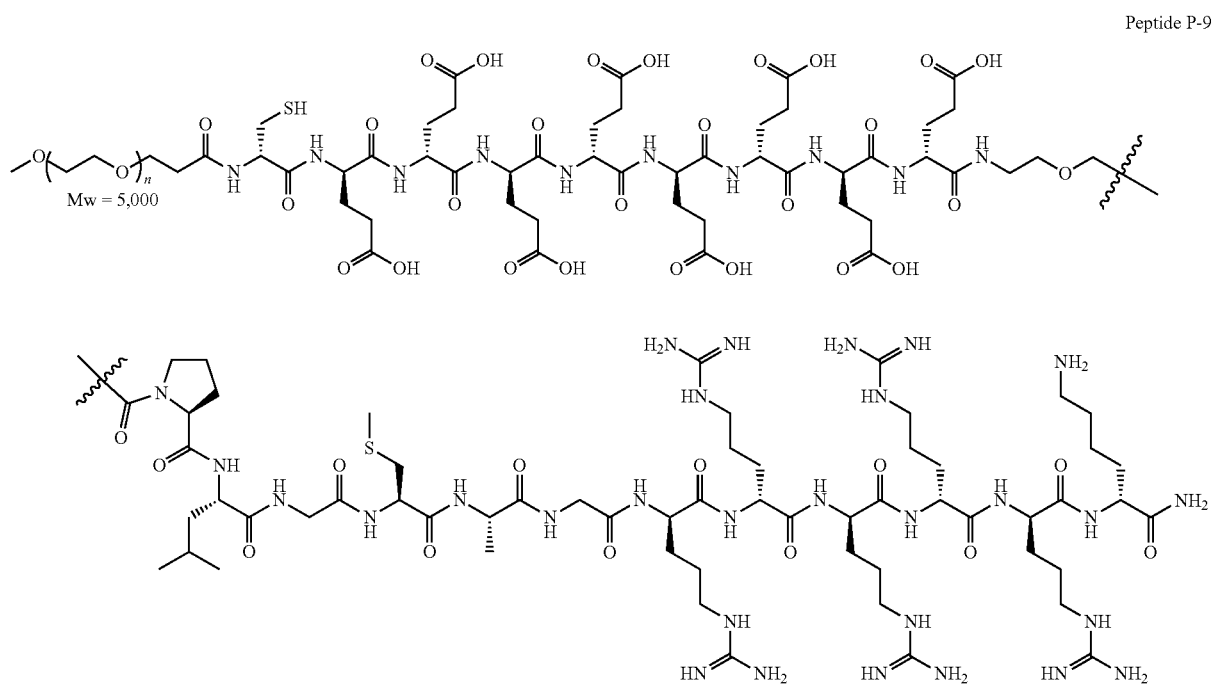

-continued
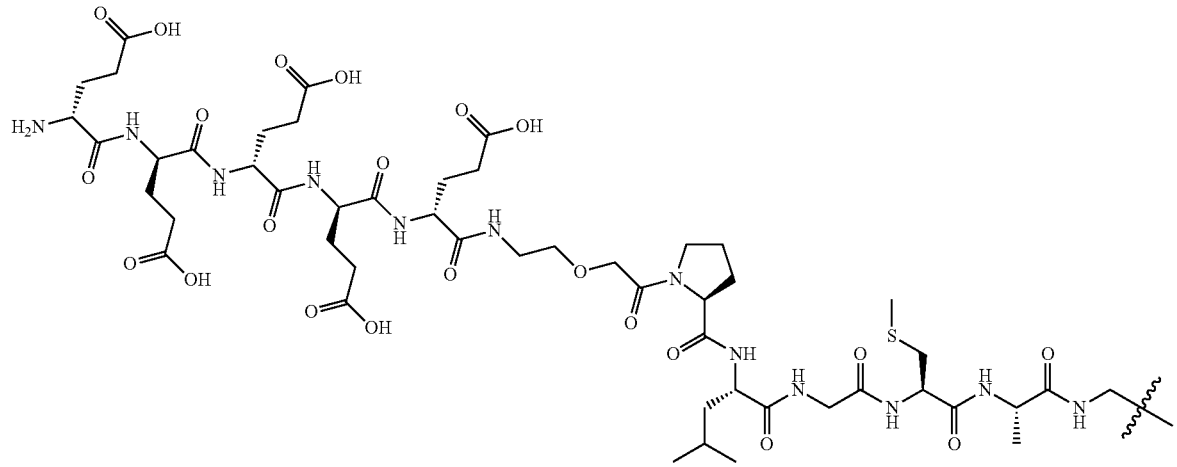
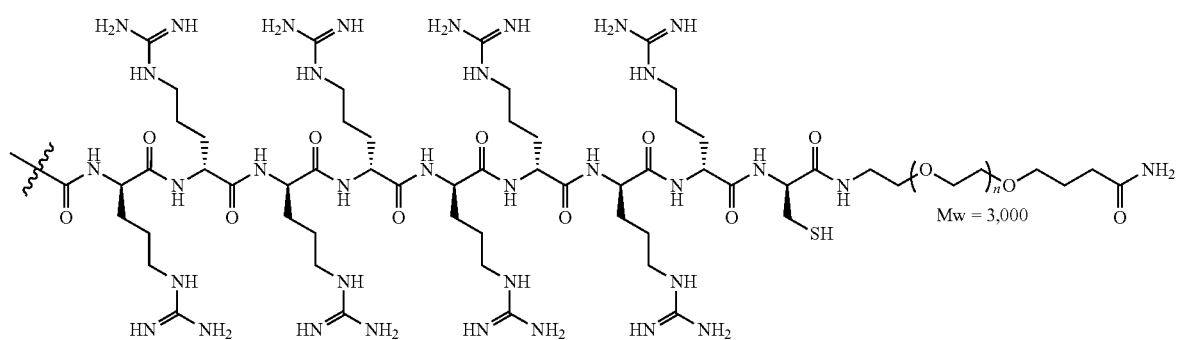
Peptide P-11
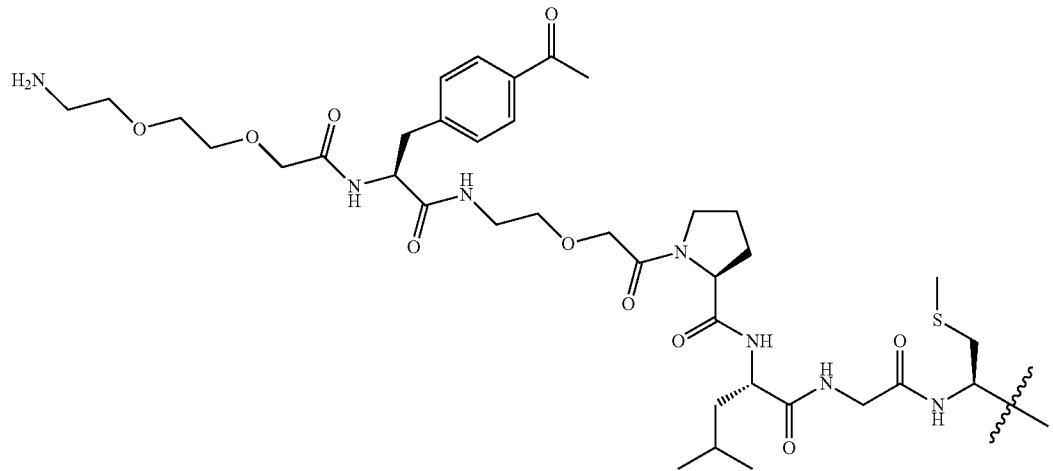
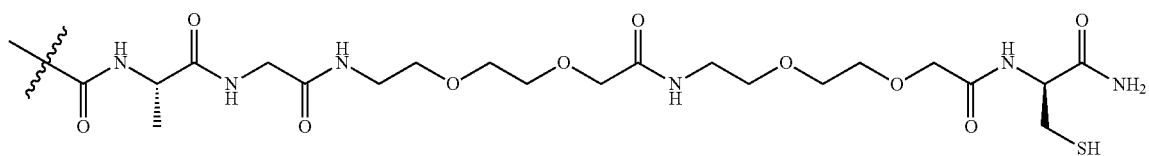

-continued
Peptide P-12
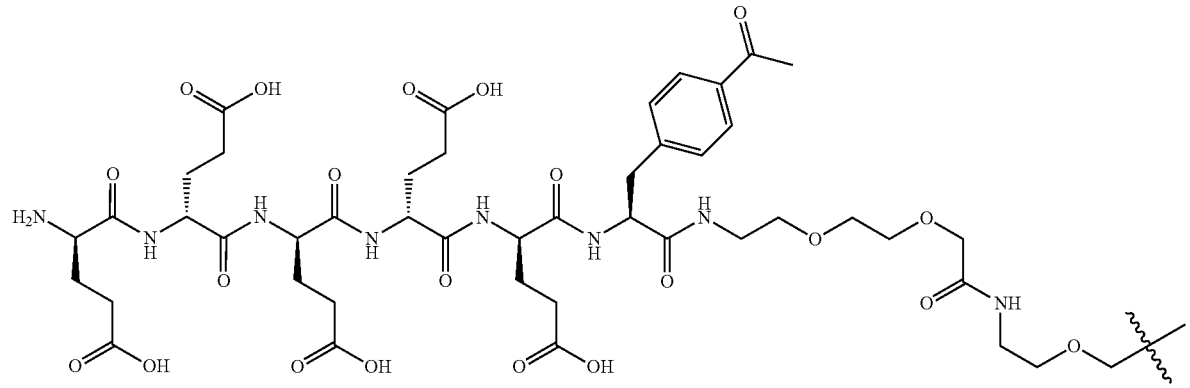
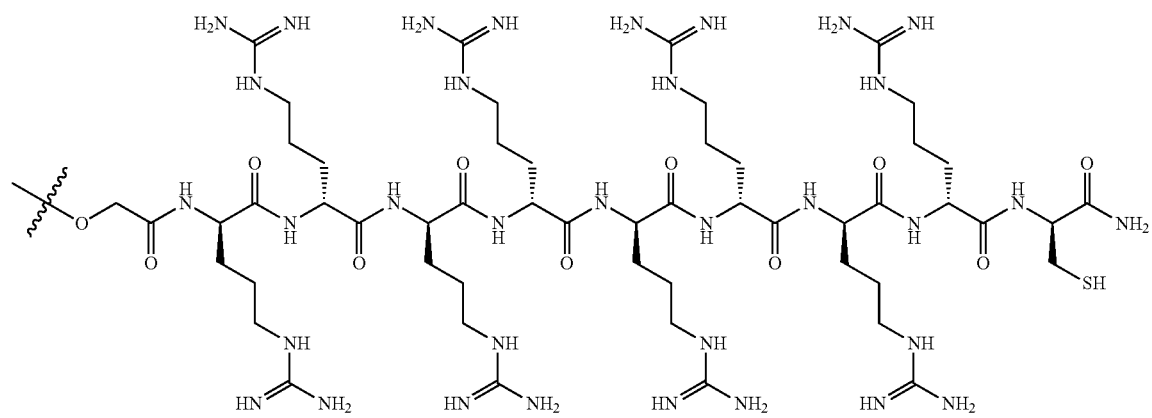
Peptide P-13
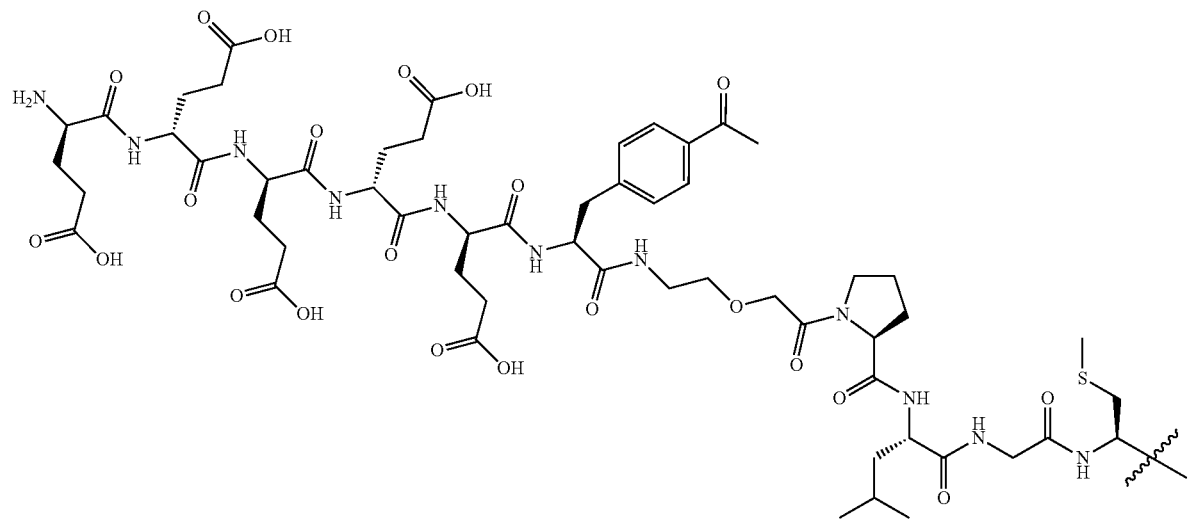

-continued
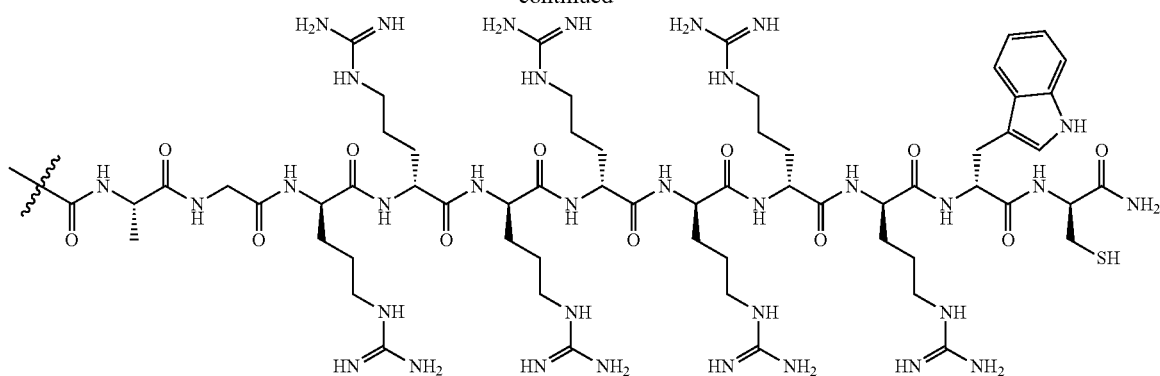
Peptide P-14
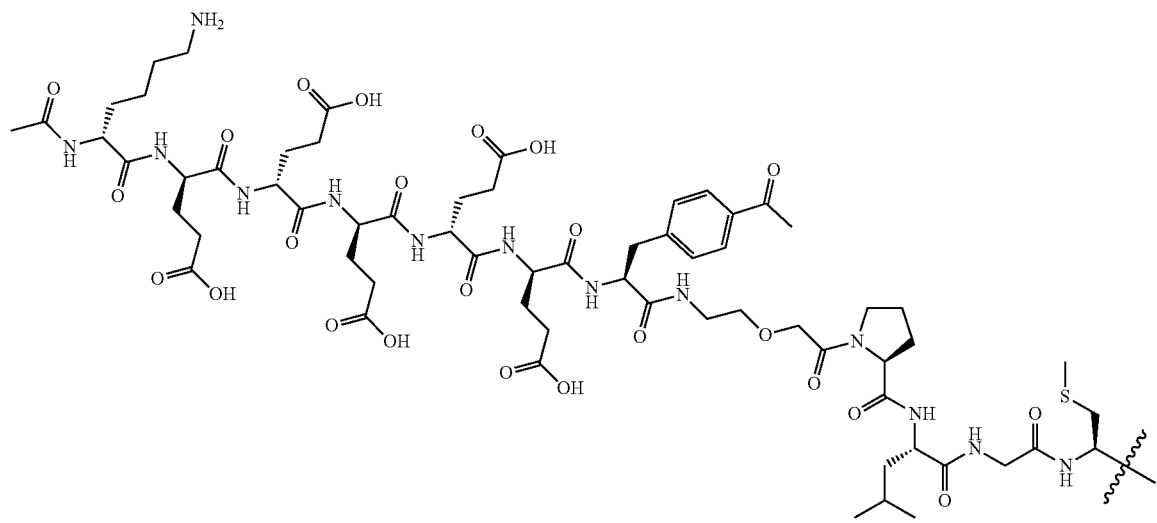
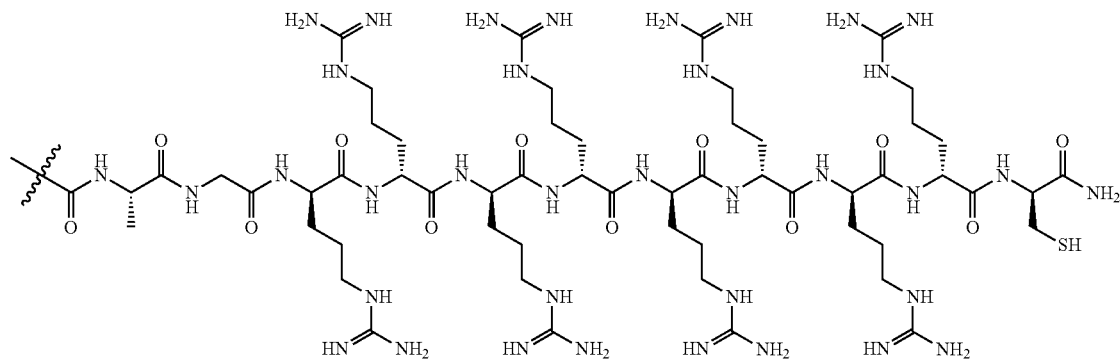

Peptide P-15
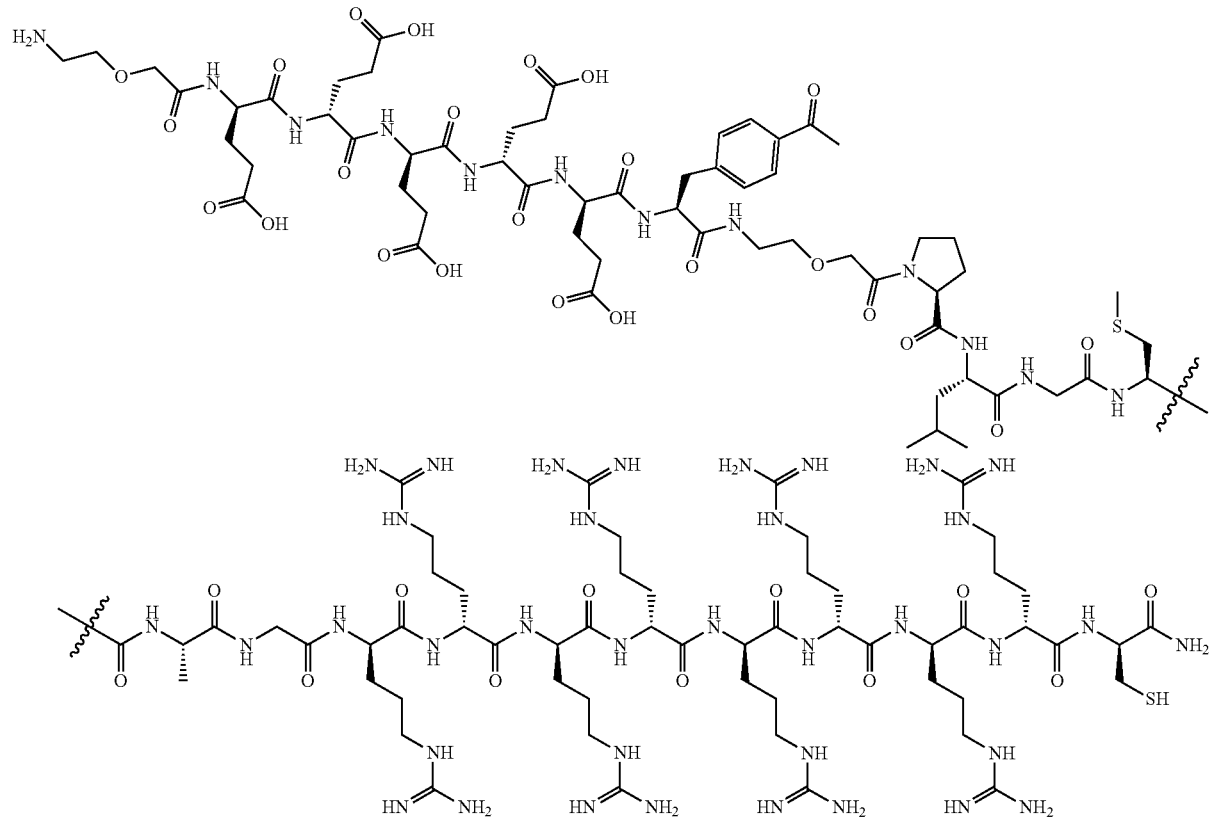
Peptide P-16
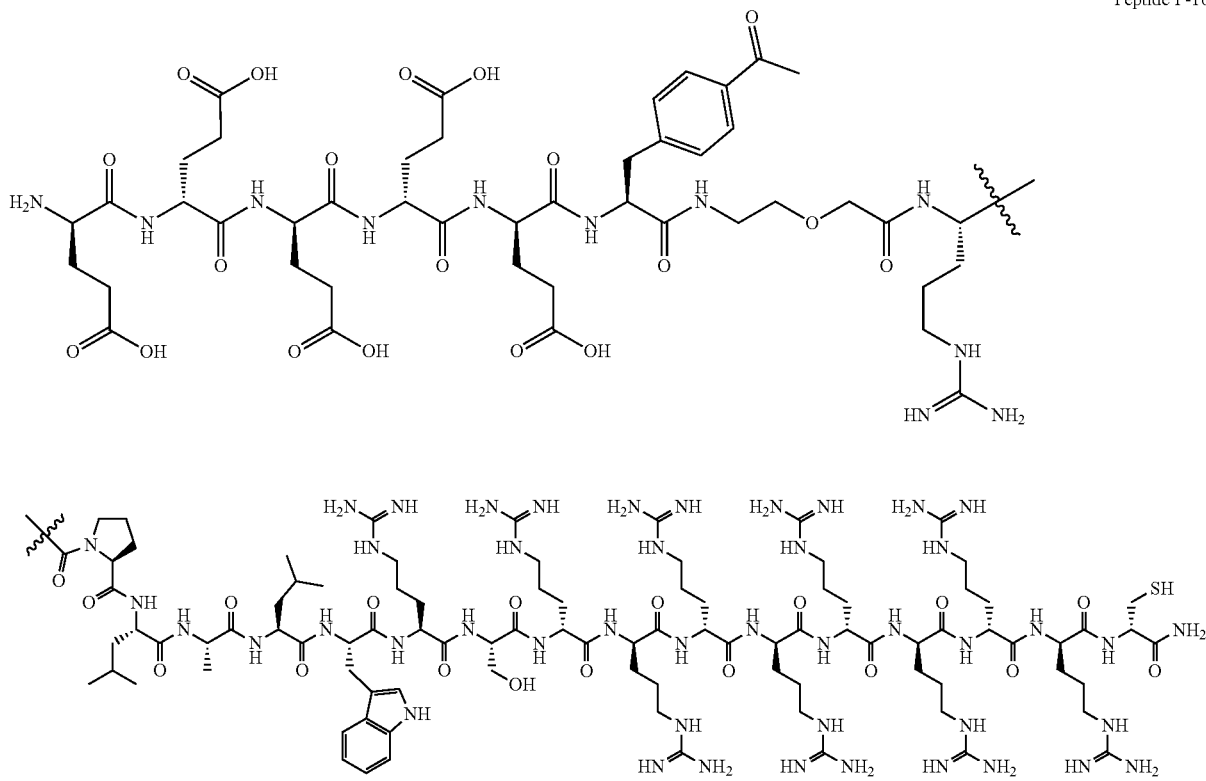

Peptide P-17
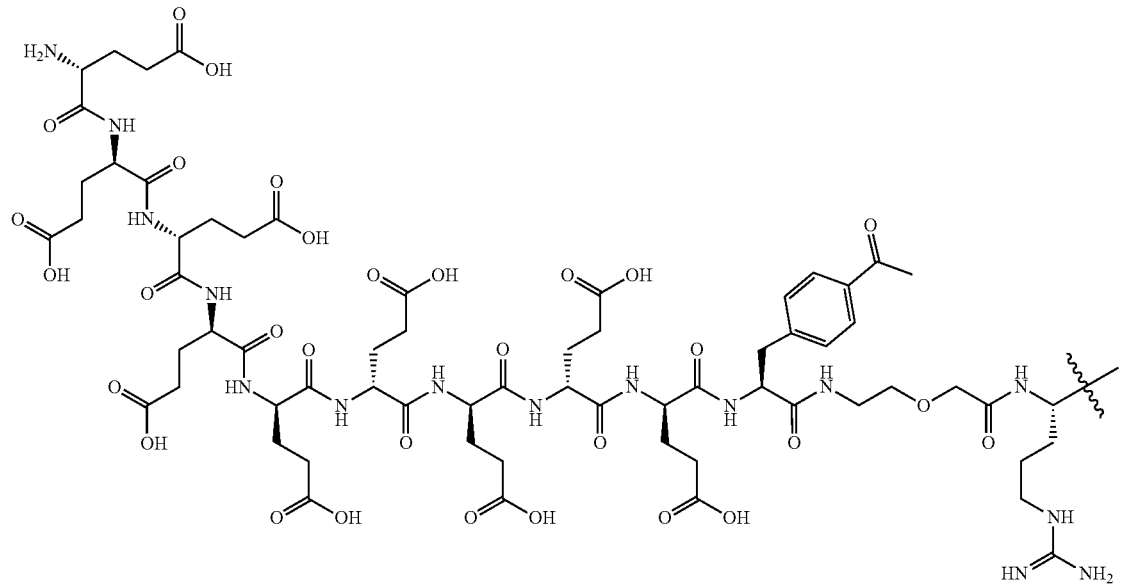
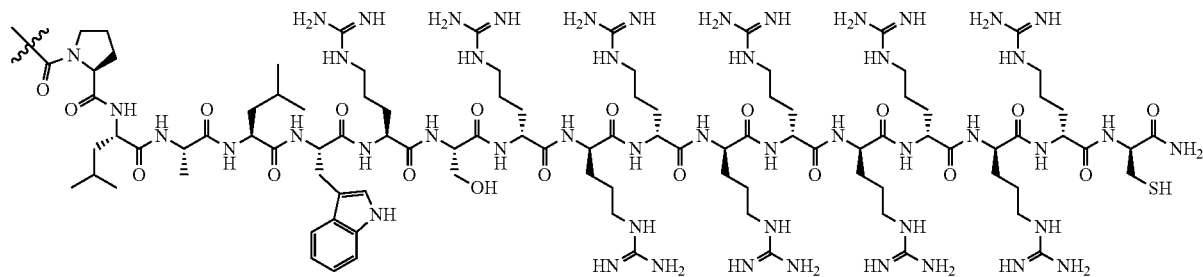
Peptide P-18
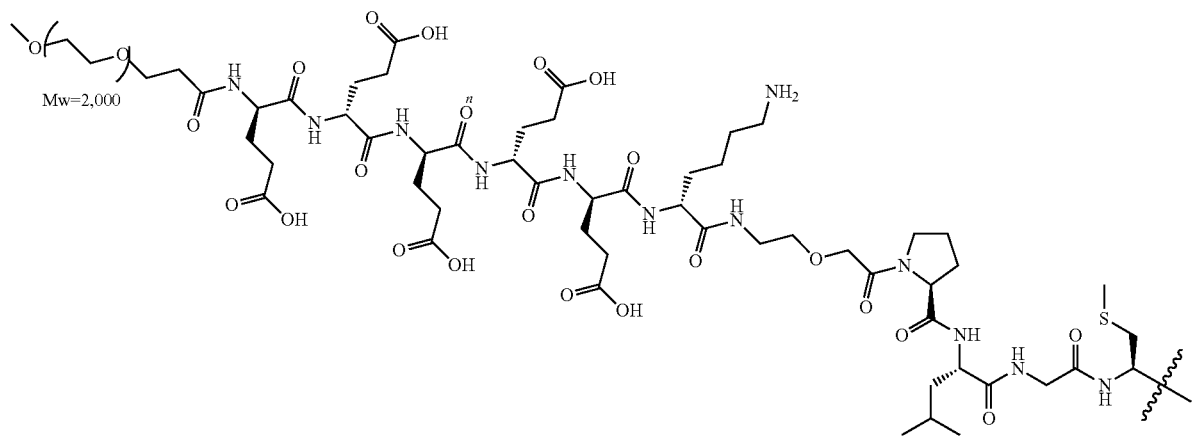

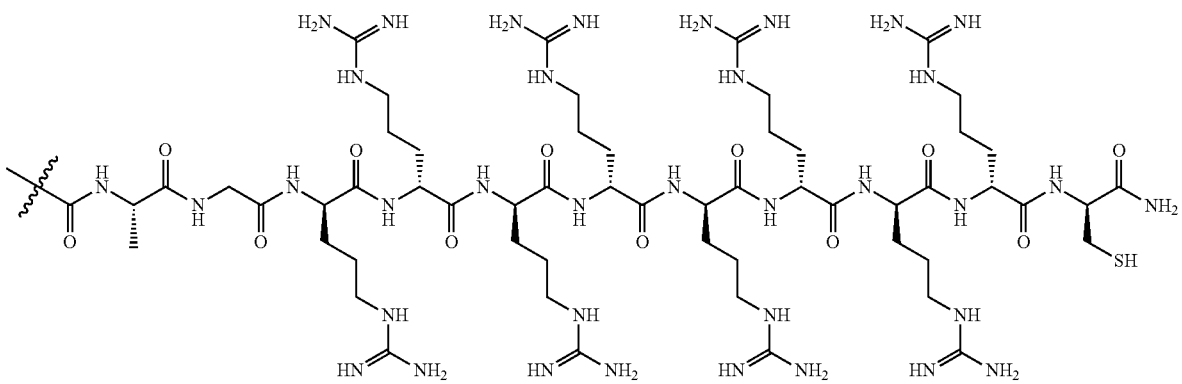

EXAMPLES

Materials and Methods

HPLC-grade acetonitrile, glycine, acetophenone and aniline were purchased from Thermo Fisher Scientific (Waltham, Mass.). Purified water was collected through Milli-Q water purification system (Millipore, Bedford, Mass.). 3-Maleimidopropionic acid-Pfp ester was purchased from Molecular Biosciences (Boulder, Colo.). PBS-EDTA buffer was purchased from Teknova (Hollister, Calif.). PBS buffer (pH 8.5, 0.5 M) was purchased from Boston Bioproducts (Ashland, Mass.). Trifluoroacetic acid (TFA) was purchased from Alfa Aesar (Ward Hill, Mass.). Dimethylformamide (DMF) and N-methylmorpholine (NMM) were supplied by Sigma-Aldrich (Milwaukee, Wis.). α-Mercaptoethyl-ω-methoxy, poly-oxyethylene (Mw ~2,000, ~5,000, ~20,000 and ~40,000) [mPEG(2K)-SH, mPEG(5K)-SH, mPEG(20K)-SH, mPEG(40K)-SH] and α-aminoxyl-ω-methoxy, polyoxyethylene (Mw ~2,000, ~5,000, ~10,000, ~20,000 and ~40,000) [mPEG(2K)-ONH$_2$, mPEG(5K)-ONH$_2$, mPEG (10K)-ONH$_2$, mPEG(20K)-ONH$_2$, mPEG (40K)-ONH$_2$] were purchased from NOF America Corporation (Irvine, Cali.f). mPEG(1K)-NHNH$_2$ (Mw ~1,000) was purchased from Nanocs (New York). IRDye 800CW maleimide (Mal-IRDye) and IRDye 750 succinimidyl ester were supplied by Li-Cor Biosciences (Lincoln, Nebr.). Lyophilized peptides P-1 to P-18 were supplied by PolyPeptide Group (San Diego, Calif.).

LC-MS analysis was carried out on an Agilent 1200 SL series in combination with AB SCIEX API 3200, equipped with CTC PAL autosampler operating at 4° C., a vacuum degasser, binary pump, UV-VIS detector, associated Analyst 1.5 analytical software and a Phenomenex column (Kinetex 2.6μ C18 100A, 100×2.1 mm) or a Waters 2695 separation module equipped with a Waters 2487 dual X absorbance detector in combination with Finnigan LCQ Deca XP mass spectrometer. The equipment is associated with Xcalibur analytical software and Peeke Scientific columns (Titan 200 5 μm, C18-MC, 50/100×2.1 mm).

Preparation HPLC were carried out on an Agilent system (Agilent 1200 series) and a Thermo Scientific column (Hypersil Gold C18, 5μ, 250×10 mm), or a Waters Delta Prep preparative HPLC System and a Varian column (F75L, C18, 15μ, 1200 g), or a Waters PrepLC System equipped with a Waters 2487 dual λ absorbance detector, Fraction Collector III, Masslynx software and a Thermo Scientific column (Hypersil Gold C18, 5μ, 250×10 mm) or a Phenomenex column (luna, C18(2), 5μ, 100A AX 150×30 mm). The mobile phase consisted of a water (0.05% TFA)(solvent A)/acetonitrile (0.05% TFA)(solvent B) gradient.

Centrifugation was carried out at 4° C. with an Eppendorf centrifuge 5810R or a Beckman Microfuge® 18.

Exemplary materials for synthesis of the selective delivery molecules disclosed herein include, but are not limited to, any of peptides P-1, P-2, P-3, P-4, P-5, P-6, P-7, P-8, P-9, P-10, P-11, P12, P-13, P-14, P-15, P-16, P-17 and P-18.

The above starting materials are summarized below:

| | Peptide Sequences |
|---|---|
| Peptide P-1 | eeeeeeeeeoPLGC$_{(Me)}$AGrrrrrrrrrc |
| Peptide P-2 | eeeeeoPLGC$_{(Me)}$AGrrrrrrrrc |
| Peptide P-3 | eeeeeF$_{(4-Ac)}$oPLGC$_{(Me)}$AGrrrrrrrrrc |
| Peptide P-4 | eeeeeeeeeF$_{(4-Ac)}$oPLGC$_{(Me)}$AGrrrrrrrrrc |
| Peptide P-5 | (Ac)eeeeeoPLGC$_{(Me)}$AGrrrrrrrrck |
| Peptide P-6 | eeeeeoPLGC$_{(Me)}$AGoF$_{(4-Ac)}$rrrrrrrrc |
| Peptide P-7 | eeeeeeeeeoPLGC$_{(Me)}$AGrrrrrrrrrcoF$_{(4-Ac)}$ |
| Peptide P-8 | [mPEG$_{(2K)}$]crrrrrrrrrPLGC$_{(Me)}$AGoeeeeek |
| Peptide P-9 | [mPEG$_{(5K)}$]crrrrrrrrrPLGC$_{(Me)}$AGoeeeeek |
| Peptide P-10 | eeeeeoPLGC$_{(Me)}$AGrrrrrrrrrc[PEG$_{(3K)}$] |
| Peptide P-11 | (Aeo)F$_{(4-Ac)}$oPLGC$_{(Me)}$AG(Aeo)(Aeo)c |
| Peptide P-12 | eeeee F$_{(4-Ac)}$(Aeo)(Aeo)rrrrrrrrc |
| Peptide P-13 | eeeeeF$_{(4-Ac)}$oPLGC$_{(Me)}$AGrrrrrrrwc |
| Peptide P-14 | (Ac)keeeeeF$_{(4-Ac)}$oPLGC$_{(Me)}$AGrrrrrrrrrc |
| Peptide P-15 | oeeeeeF$_{(4-Ac)}$oPLGC$_{(Me)}$AGrrrrrrrrrc |

| Peptide Sequences | |
|---|---|
| Peptide P-16 | eeeeeF$_{(4-Ac)}$oRPLALWRSrrrrrrrrc |
| Peptide P-17 | eeeeeeeeeF$_{(4-Ac)}$oRPLALWRSrrrrrrrrrc |
| Peptide P-18 | [mPEG$_{(2K)}$]eeeeekoPLGC$_{(Me)}$AGrrrrrrrrc |

Abbreviations:
Standard 1 letter amino acid abbreviations were used in all the sequences.
Lowercase characters indicated D-amino acids.
All peptides were amidated at C-terminus.
o: 5-(amino-3-oxapentanoyl);
F$_{(4-Ac)}$: para-acetyl-(L)-phenylalanine;
C$_{(Me)}$: S-methyl-(L)-cysteine.
PEG(3k): α-amino-ω-amide poly(ethylene glycol) with an averaged three thousand Daltons molecular weight;
mPEG(2k): α-carboxy-ω-methoxy poly(ethylene glycol) with an averaged two thousand Daltons molecular weight;
mPEG(5k): α-carboxy-ω-methoxy poly(ethylene glycol) with an averaged five thousand Daltons molecular weight.
Ac: acetyl
(Aeo): 2-(2-2(aminoethoxy)ethoxy)acetyl

Example 1

Synthesis of SDM-41 from Peptide P-16

123
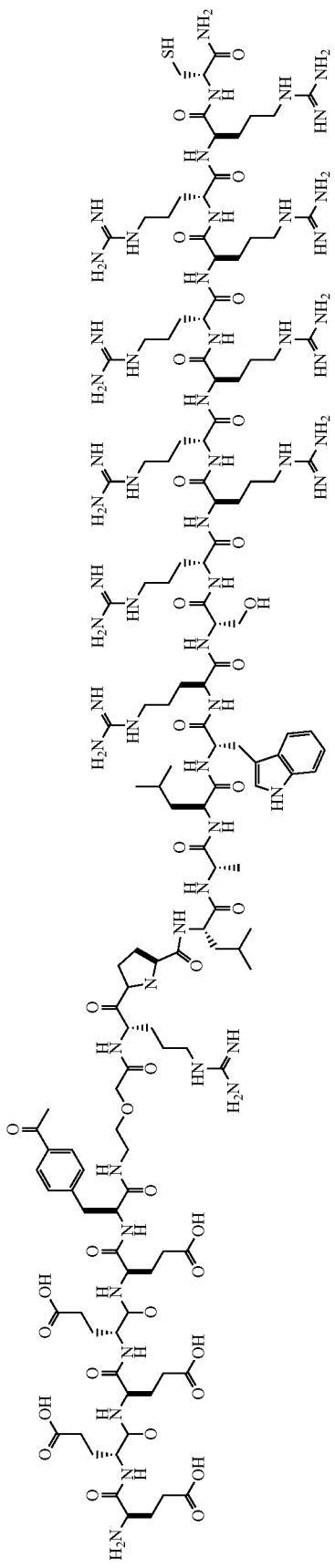
P-16
Cy5-MaI,
CH₃CN, pH 8.5,
40 min
⟶
124
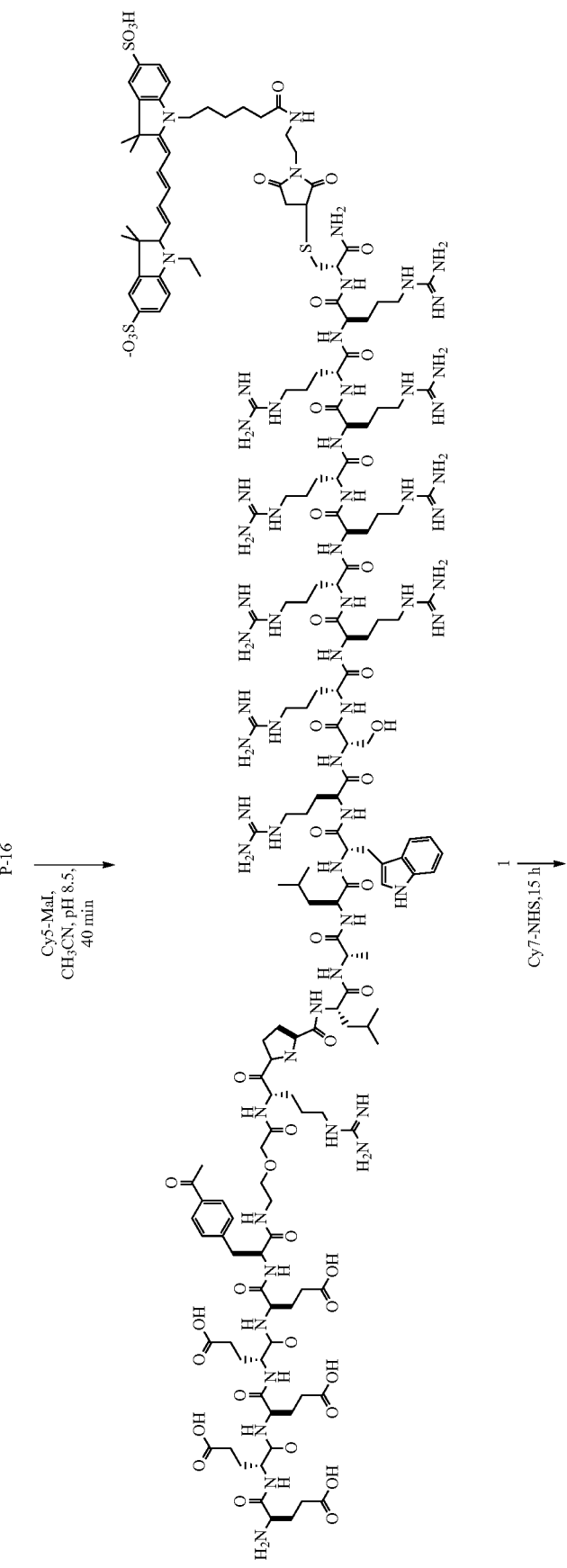
Cy7-NHS, 15 h
⟶

-continued
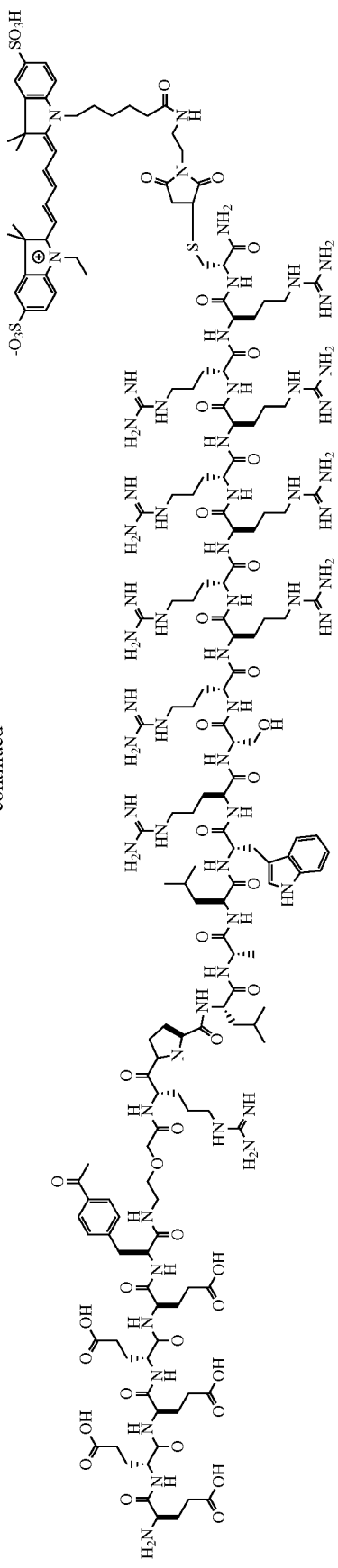
→ 1 Cy7-NHS, 15 h
→ 2 mPEG(2K)-ONH2 pH 3.0, 0.1 M Glycine 20 mM aniline, 15 h
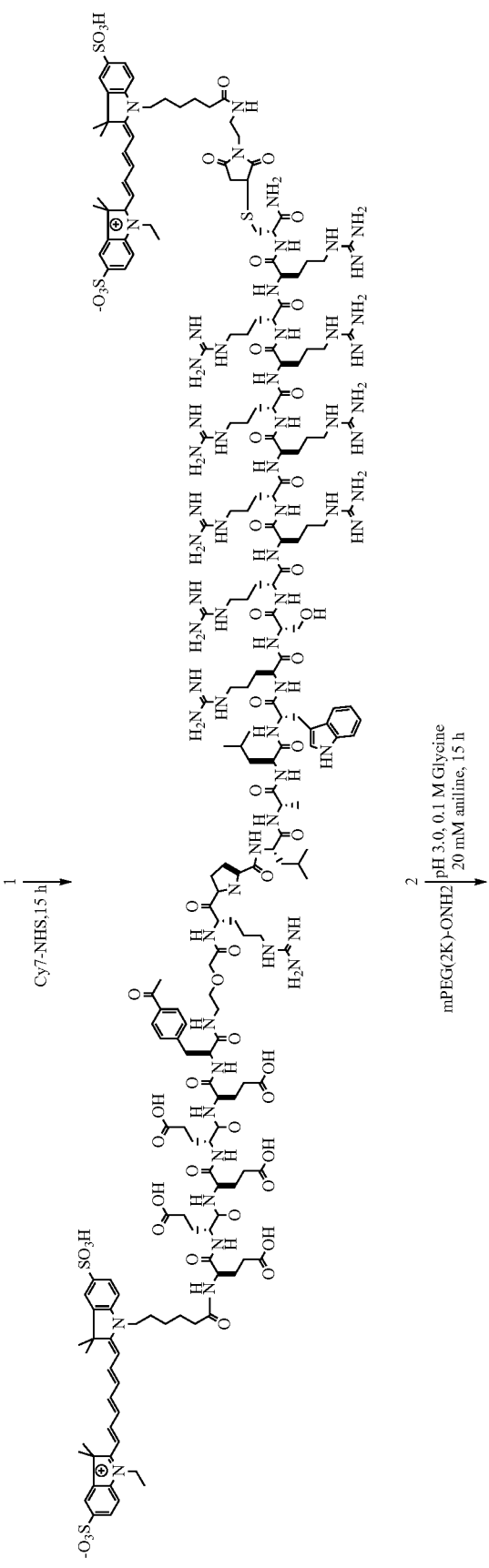

-continued
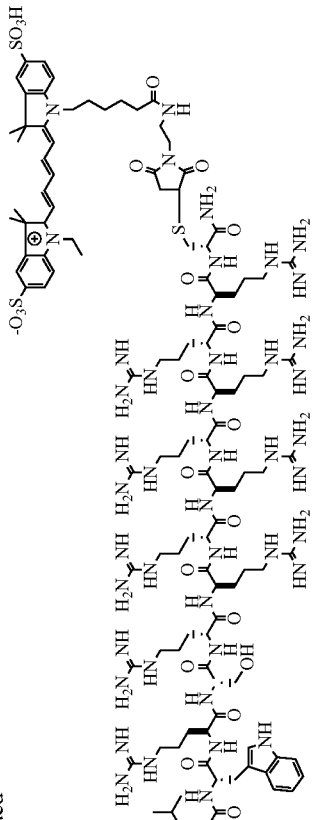
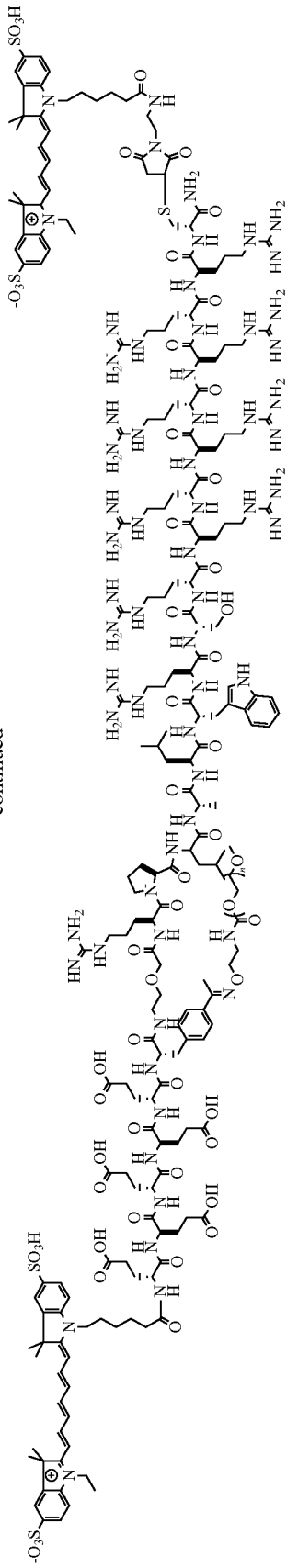
Mw ~ 2,000
SDM-41

Synthesis of Intermediate 2

To a solution of peptide P-16 (10 mg, 2.0 µmol) in acetonitrile (0.5 mL) and PBS buffer (0.5 mL, pH 8.5, 0.5 M) at room temperature in the dark was added Cy5 maleimide (2.3 mg, 2.7 µmol) with stirring. The reaction was followed by LC-MS and completed in 40 min. To the reaction mixture was added Cy7-NHS followed by PBS buffer (1.0 mL, pH 8.5, 0.5 M). After stirring for 15 h, the mixture was purified by HPLC to afford intermediate 2 (3.8 mg, 32%). Calculated: $[M+3H]^{3+}$ $(C_{211}H_{319}N_{62}O_{53}S_5)$ m/z=1577; Found ESI: $[M+3H]^{3+}$ $(C_{211}H_{319}N_{62}O_{53}S_5)$ m/z=1577.

Synthesis of Selective Delivery Molecule SDM-41

The mixture of intermediate 2 (3.8 mg, 0.65 µmop and mPEG(2K)-$ONH_2$ (2.5 mg, 1.1 µmol) in glycine buffer (1.0 mL, 0.1 M, 20 mM aniline, pH 3.0) and acetonitrile (0.5 mL) was stirred at room temperature in the dark for 15 h. After the reaction was complete, acetophenone (7 µL, 60 µmol) was added. The mixture was stirred at room temperature for 2 h. Purification by RP-HPLC afforded selective delivery molecule SDM-41 (2.1 mg, 40%).

Example 2a

Enzyme Dependent Fluorescence Enhancement and Color Changes

Selective delivery molecule 41 was dissolved in TCNB buffer (pH 7.5) at room temperature. Concentration of SDM-41 was 0.156 to 5 µM. Fluorescence intensity was measured on a Molecular Devices Spectromax M2 spectrophotometer. The sample was excited at 620 nm and the emission was measured at 670 nm (Cy5).

Peptide cleavage was initiated with addition of MMP-7 at a final concentration of 1 nM. Cleavage rate was measured as change in relative fluorescence intensity of Cy5 per minute, which was subsequently converted to concentration of Cy5-peptide with a standard curve in order to calculate $k_{cat}$ and $K_m$ for cleavage of SDM-41 by MMP-7 (FIG. 1). The data show that SDM-41 is substrate for MMP-7 and that it generates a fluorogenic FRET signal upon enzyme cleavage.

Example 2b

Enzyme Dependent Fluorescence Enhancement and Color Changes

Selective delivery molecule 42 is dissolved in TCNB buffer (pH 7.5) at room temperature at 1 µM. Fluorescence spectra are recorded on F-2500 fluorescence spectrometer. Excitation of the Cy5 fluorescence donor is excited at 625 nm and the emission is measured at 669 nm.

Peptide cleavage is initiated with addition of MMP-2 at a final concentration of 1 nM. The cleavage reaction is complete within 2 hours.

Example 3

Fluorogenic Response from Tumor Homogenates

HT1080 cells (Cat. #CCL-121; American Type Culture Collection, Va., USA) are grown under exponential growth conditions in humidified atmosphere of 5% $CO_2$ in air at 37° C. until reaching 80-100% confluence before harvesting for mouse implantation. Each nude mouse is hand restrained and injected with $2\times10^6$ HT-1080 cells into the mammary fat pad using a 25-G needle. HT-1080 tumors are harvested when they had reached 100-200 $mm^3$ in size (typically 1-2 weeks post-tumor cells implantation).

HT-1080 tumors are homogenized using ultrasonic disruption. 1 nM MMP-7 or 10 µL tumor tissue homogenates (TH2 and TH3) are mixed with 1 µM SDM-42 in 100 µL buffer for 24 h at 37° C. The samples are loaded on a polyacrylamide gel and separated using electrophoresis. After incubation with HT-1080 tumor homogenates, SDM-42 is cleaved and becomes highly fluorescent.

Example 4

In Vivo Imaging Assay for Tumor Contrast

HT-1080 xenograft model is generated as described in Example 3 and used to evaluate the ability of molecules to provide in vivo tumor fluorescence contrast compared to surrounding tissue. Fluorescent conjugates are tested in HT-1080 tumor-bearing mice once the tumors had reached 100-200 $mm^3$ in size (typically 1-2 weeks post-tumor cells implantation). Conscious HT-1080 tumor-bearing mice are restrained using a rotating tail injector (Cat.#RTI; Braintree Scientific, MA, USA) and dosed intravenously (tail vein) with SDM-43, SDM-44, SDM-45 or SDM-46 at between 0.1 and 5 nanomoles per mouse in 100 uL saline solution. In preparation for imaging, mice are lightly anesthetized with a mixture of ketamine/xylazine (Cat. #K-113; Sigma, Aldrich, Mo., USA) given intraperitoneally (14/gram body weight) to minimize movement.

Serial whole-body imaging (tumor included) is done using a whole-animal fluorescent visualization imaging system or Olympus stereo fluorescent microscope. The mice are positioned on their backs and imaging is performed from the top to image the ventral side of the animal. Excitation and emission wavelengths are selected based on the fluorescent dye used. Contrast is calculated using the following equation:

Contrast=(Fluorescence intensity of tumor−Fluorescence intensity of contralateral chest tissue)/Intensity of contralateral chest tissue).

Contrast greater than 0.4 in the whole animal is easily detected by eye in the whole animal image and is good contrast. Contrast >0.7 is high contrast.

The mice are imaged several times between 1-24 hours after injection.

Example 5

In Vivo Distribution and Compounds with Improved Tissue Accumulation

To determine the total dye accumulation in various organs, HT-1080 xenograft mice are sacrificed and tissue samples from blood, liver, kidney, and tumor are collected 6 hours after compounds are administered iv via the tail vein. 3-4 mice are used for each data point. Blood samples are stored at 4° C. overnight and then centrifuged at 15,000 rpm to separate out the serum. The organs are mixed in a ProK buffer (0.25 mg/ml Prok, 0.1 mg/ml DNAse, 150 mM NaCl, 10 mM Tris pH8.0, 0.2% SDS) at 104/mg tissue and cut into small pieces using scissors. The tissue/digest solution is then sonicated for 1 minute at 67% duty cycle and digested overnight at 37° C. After digestion, the sample is centrifuged at 15,000 rpm and the tissue homogenate is aspirated off and stored at 4° C.

The tissue concentration of fluorescent compounds is determined from fluorescence standard curves generated by spiking in know concentrations of administered compounds into serum and tissue homogenates (at various dilutions) from control animals that are not injected with compound. The linear range for each compound is determined for each tissue. Fluorescence measurements are done on either a fluorescent plate reader or fluorescence spectrometer.

Example 6a

In Vivo Detection of Cancer Metastases to Lymph Node with FRET SDMs

Fluorescence labeling of metastatic cervical lymph nodes following intravenous and peritumoral administration of fluorescent SDMs in tumor bearing mice.

The following model and assays were used to determine the ability of fluorescent SDMs to detect cancer metastases to lymph nodes in immunocomptent BALB/c mice (Charles River, Wilmington, Mass. 01887) bearing syngeneic ear tumors.

Mouse Model. The mice were housed in groups of 4 in individually ventilated IVC disposable cages (Innovive, Inc., San Diego, Calif. 92121) and had free access to standard laboratory chow (Cat. #2018, Harlan Laboratories, Inc. Indianapolis, Ind. 46250) and drinking water. Animals were kept under controlled environmental conditions (12-h/12-h light/dark cycle) for at least 5 days before tumor cell implantation. All experimental procedures were carried out under the approved IACUC protocol #EB11-002-009A. Murine 4T1 tumor (ATCC® Number: CRL-2539™) and mammary carcinoma (Polyoma Middle T 8119 subclone "PyMT 8119") cells from the American Type Culture Collection (ATCC, Manassas, Va. 20108) and the University of San Diego, Calif. (UCSD, La Jolla, Calif. 92093) respectively were grown separately using standard cell culture techniques. Tumor cells ($4 \times 10^5$ tumor cells/50 L/mouse) were suspended in DPBS/Matrigel™ (1:1 vol) and injected subcutaneously on the mouse ear pinna above the auricular cartilage for primary tumor induction. The in vivo imaging of metastatic cervical lymph nodes in ear tumor-bearing mice used as surrogate murine model of metastatic breast cancer took place seventeen to twenty days following tumor cell implantation.

Compound administration. For the intravenous administration (tail vein injection) of SDMs, mice were restrained in a rotating tail injector (Cat. #RTI, Braintree Scientific, Inc., Braintree, Mass. 02185) and the test article (5-120 μM; 100 μL/mouse) injected in mouse using a $28G^{1/2}$ insulin syringe (Cat. #14-826-79, Becton Dickinson and Company, Franklin Lakes, N.J. 07417). To perform the peritumoral injection of SDMs, each involved mouse was sedated using the ketamine/xylazine (Ketaject® & Xyla-ject®, Phoenix Pharmaceuticals, St. Joseph, Mo. 64506) mixture administered intraperitoneally and the test article (5-120 μM; 30-60 μL/ear) injected subcutaneously around the primary tumor and contralateral ear pinna using a 30G PrecisionGlide™ needle (Cat. #305106, Becton Dickinson and Company, Franklin Lakes, N.J. 07417). After dosing, each mouse was returned to the assigned cage and kept under controlled environmental conditions before being examined for the fluorescence imaging of cervical lymph nodes 1-24 hours later.

Fluorescence imaging. To image the cervical lymph nodes, each mouse was deeply anesthetized with a mixture of ketamine/xylazine administered intraperitoneally. The deeply anesthetized mouse was transferred on a piece of black cork (4×4 inches, Quartet®, ACCO Brands, Lincolnshire, Ill. 60069, USA) for blunt dissection and imaging of cervical lymph nodes using a computerized fluorescent stereomicroscope (SZX10, Olympus Optical, Colo., LTD, Japan) equipped with appropriate fluorescence filters for both single intensity and two fluorophore fluorescence ratio detection. For example, filters for Cy5 and Cy7 were used for FRET-based SDMs with Cy5 and Cy7. After in vivo fluorescence imaging (see below for ratio imaging method), the cervical lymph nodes were surgically removed, fixed in 10% buffered formalin and processed for histology (Hematoxylin & Eosin staining) to assess the fluorescence/cancer correlation and determine diagnostic performance of SDMs.

Emission Ratio Imaging Method. Fluorescence images were acquired using an Olympus SZX10 Research Stereo Microscope (Olympus America, Center Valley, Pa.). For Cy5 and Cy7 FRET-based SDMs an excitation filter centered at 620 nm (Chroma ET620/60x, Chroma Technology Corp. Bellows Falls, Vt.) and emission filters centered at 700 nm and 810 nm (Chroma filters ET700/75m and ET810/90m) were used to produce two images at different emission wavelengths. Images were acquired with an Orca-R2 camera (Hamamatsu, Bridgewater, N.J.) connected to a Windows-based computer. Two methods were used to determine emission ratios for lymph nodes. For one method the intensity was averaged over a region of interest (ROI) drawn to include part or all of the lymph node of interest. The Emission ratio was then calculated from the intensity data for each region of interest.

$$\text{Roi EmissionRatio}=(\text{roiInt1}/\text{Exp1})/(\text{Int2}/\text{Exp2}) \quad \text{(equation 1)}$$

where:
roiInt1=averaged intensity for ROI at emission wavelength 1 with ET700/75m filter
Exp1=exposure time used for Int1
roiInt 2=average intensity for ROI at emission wavelength 2 with ET810/90m filter
Exp 2=exposure time used for Int2

A second method used to determine emission ratios was based averaging the emission ratio from a region of interest (ROI) drawn to include part or all of the lymph node of interest taken from an emission ratio image. Emission ratio images were produced by using a modified form of equation 1 that included a scaling factor so that the pixel values would fall between 0 and 255 for an 8-bit image.

$$Px \text{ EmissionRatio}=k*(px \text{ Int1}/\text{Exp1})/(px\text{Int2}/\text{Exp2}) \quad \text{(equation 2)}$$

where:
k=scaling factor
pxInt1=pixel intensity at emission wavelength 1 with ET700/75m filter
Exp1=exposure time used for Int1
pxInt 2=pixel intensity at emission wavelength 2 with ET810/90m filter
Exp 2=exposure time used for Int2

Figure 2:
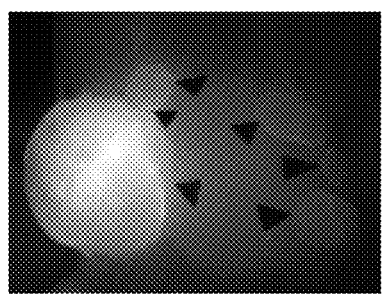
FIG. 2 depicts donor (left), acceptor (middle), and fluorescence emission ratio (right) images for SDM-41 (Example 6a).
Figure 2:
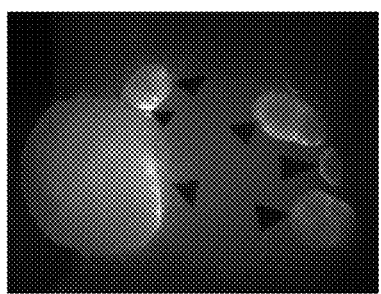
Figure 2:
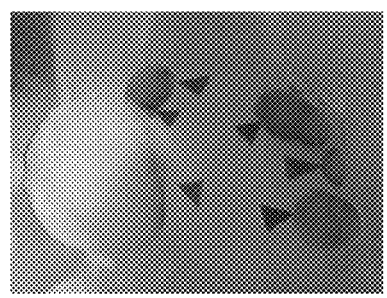

An example of an emission ratio images generated using equation 2 where Exp1=0.7 sec, Exp2=2.5 sec and k=24 for SDM-41 is shown in FIG. 2, which shows the donor (left), acceptor (middle) and fluorescence emission ratio (right) images for SDM-41.

Emission ratios for lymph nodes gave quantitatively similar results using either method.

Lymph nodes were identified as either metastatic or non-metastatic by a pathologist based on H&E staining. Emission ratio contrast for each SDM (selective delivery molecule) was then quantified by dividing the average emission ratio of the metastatic nodes by the average emission of the non-metastatic nodes and subtracting one as shown in equation 3:

$$ERC = MetAV/ConAV - 1 \quad \text{(equation 3)}$$

where:

ERC=emission ratio contrast

MetAV=average metastatic lymph node emission ratio

ConAV=average non-metastatic contralateral lymph node emission ratio

Although useful for detecting cancerous lymph nodes, a contrast of 20 to 50% was considered low, an increase of 50 to 100% was considered good, while an increase greater than 100% was considered excellent.

Example 6b

High Diagnostic Sensitivity and Specificity for SDM in Metastatic Lymph Node Model Key performance metrics of a diagnostic agent are sensitivity and specificity. Sensitivity relates to the ability to correctly diagnose test positives. While specificity relates to the ability to correctly diagnose test negatives.

The following model and assays were used to determine the ability of fluorescent SDMs to detect cancer metastases to lymph nodes in immunocomptent BALB/c mice (Charles River, Wilmington, Mass. 01887) bearing syngeneic ear tumors.

As an example of high diagnostic performance of a FRET SDM, data generated from SDM-41 in the 4T1 mouse metastatic lymph model was used. SDM-41 was administered via IV tail vein injection. After 3 to 6 hours, the mice lymph nodes were imaged using fluorescence ratio imaging as described previously to determine whether or not the lymph node had a high ratio (diagnosed cancer positive) or low ratio (diagnosed cancer negative). Sensitivity and specificity was determined using receiver operating characteristic (ROC) or ROC curves. For ROC curve analysis, data is divided into a binary classification of positives and negatives based on a threshold value for the emission ratio. The ROC curve plots true positive fraction of positives (true positive rate) versus false positive fraction of negatives (false positive rate).

Figure 3:
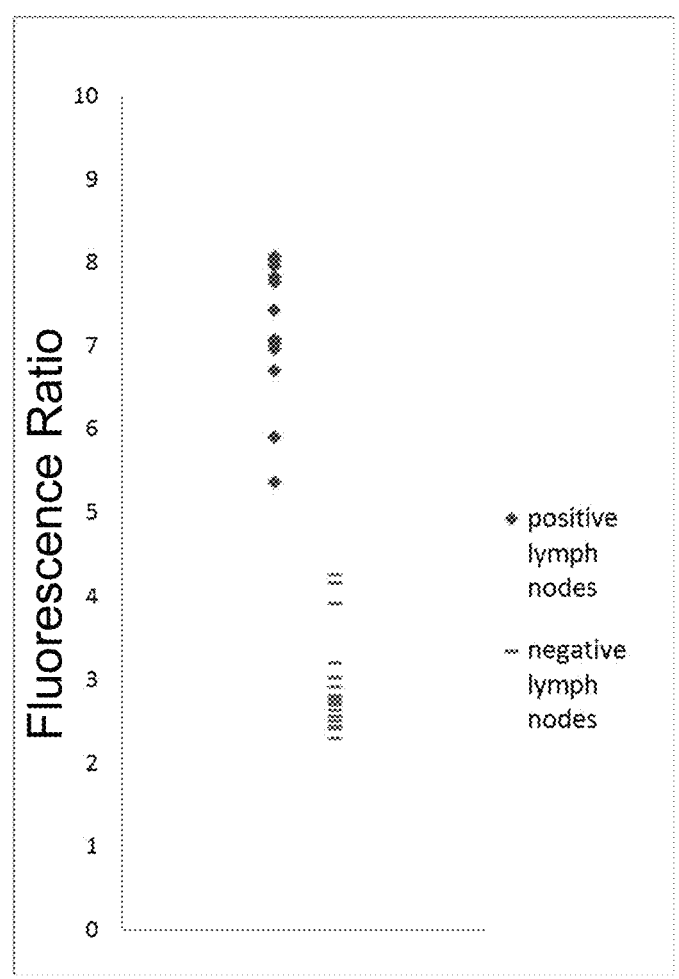
FIG. 3 shows a scatter plot of emission ratio data of positive and negative nodes using SDM-41 in mouse metastatic lymph node model (Example 6b).
Figure 4:
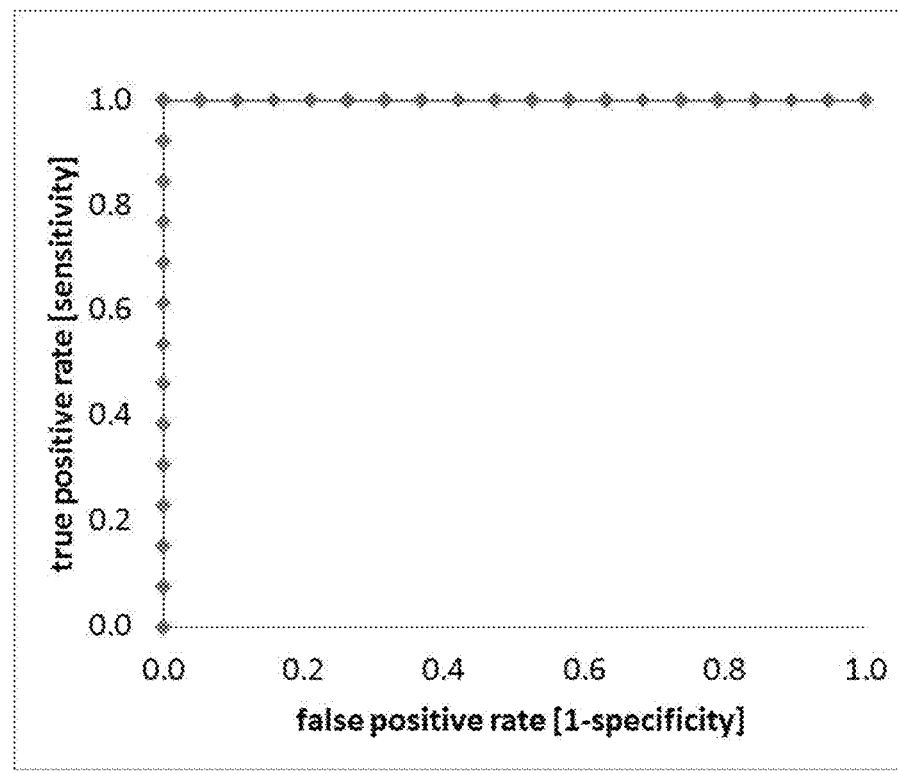
FIG. 4 shows a ROC curve generated by changing the threshold value used to assign either a positive or negative metastatic prediction from emission ratio data using SDM-41 in metastatic lymph node model (Example 6b).

True positives, false positives, true negatives, and false negatives were determined by comparing the prediction based on the fluorescence emission ratio data and threshold value with the positive or negative assignment made by a pathologist using H&E staining. The emission ratio values for the cancer positive and negatives (as determined by H&E staining by a certified pathologist) are shown in FIG. 3. The two populations are completely separated demonstrating 100% diagnostic sensitivity and specificity in this metastatic breast cancer lymph node model. The threshold value was gradually adjusted from low to high to obtain a full ROC curve from (1, 1) or all positives to (0, 0) or all negatives. A ROC curve is shown in FIG. 4. Data from ~32 lymph nodes were used to generate this curve. Note that sensitivity and specificity can be determined for each point in the ROC curve. This data illustrates 100% diagnostic sensitivity and specificity for separating cancerous lymph nodes from those without cancer. Sensitivity is the true positive rate while specificity is one minus the false positive rate. Equations used to generate the ROC curve are shown below.

$$TPR = TP/(TP+FN)$$

$$FPR = FP/(FP+TN)$$

where:

TPR=true positive rate

FPR=false positive rate

TP=# of true positives

TN=# of true negatives

FP=# of false positives

FN=# of false negatives

In this example both sensitivity and specificity are 100% for all threshold values between ~4.3 and ~5. This means that all lymph nodes were correctly identified with the FRET emission ratio method when compared to the gold standard histopathology. Generally, sensitivity and specificity values >90% are considered very high.

Example 7

Ex Vivo Mouse PyMT 8119 Tumor Activity Assay: SDM Cleavage and FRET Emission Ratio Response in Mouse Cancer Tissue Compared to Non Cancerous Tissue Tumor and muscle tissue samples from PyMT 8119 tumor bearing mice are collected and frozen at −80° C. The tissues are thawed and homogenized in cold TCNB buffer (pH 7.5, 50 mM Tris-HCl, 10 mM $CaCl_2$, 150 mM NaCl and 0.05% Brij35) at 100 mg/200 µL using ultrasonic disruption (VCX500, Sonics & Materials Inc, Newtown, Conn.). After homogenates are centrifuged at 15,000 g at 4° C. for 20 min, supernatants are collected. APMA (p-aminophenylmercuric acetate, 90 µL, 2 mM in TCNB buffer) is added to the supernatants (90 ∞L). The resulting mixtures are incubated at 37° C. for 1 h before use. 500 nM of SDM-42 is used for the cleavage of 45 µL of activated tissue supernatants (final volume: 50 µL). The assay is carried out using a SpectraMax M2 spectrometer with SoftMax Pro v4.5 software. Fluorescence signals of ($\lambda$ex, 620 nm, $\lambda$em, 670 nm), ($\lambda$ex, 620 nm, $\lambda$em, 773 nm) and ($\lambda$ex, 720 nm; $\lambda$em, 773 nm), where $\lambda$ex and $\lambda$em stand for excitation and emission wavelengths respectively, are measured as a function of time at room temperature. Samples are measured in triplicate.

Example 8

Figure 5:
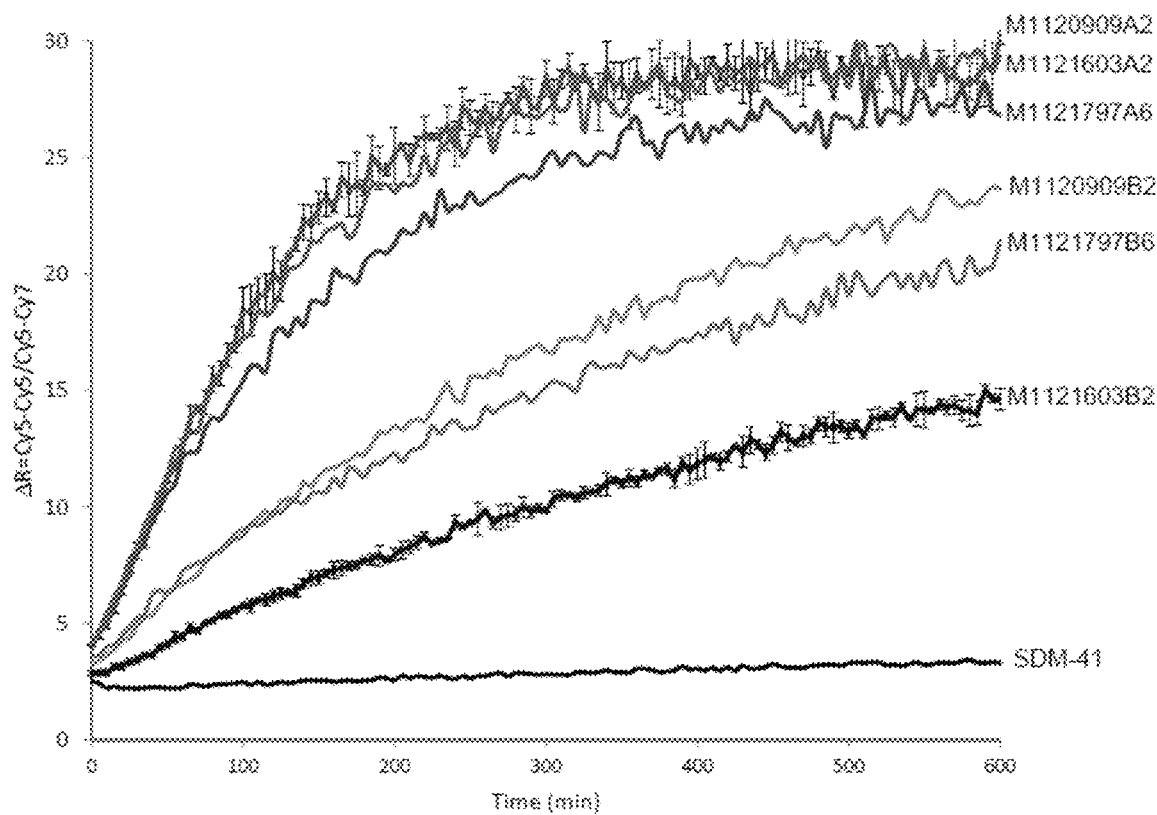
FIG. 5 depicts change in SDM-41 fluorescence ratio in homogenized cancerous tissue (M1120909A2, M1121603A2, M1121797A6) and healthy tissue (M1120909B2, M1121797B6, M1121603B2) from breast cancer patients, individual kinetic traces (Example 8). The cancerous tissue (M112090A2, M1121603A2, and M1121797A6) cleaves SDM-41 faster than normal tissue ((M112090B2, M1121603B2, and M1121797B6).
Figure 6:
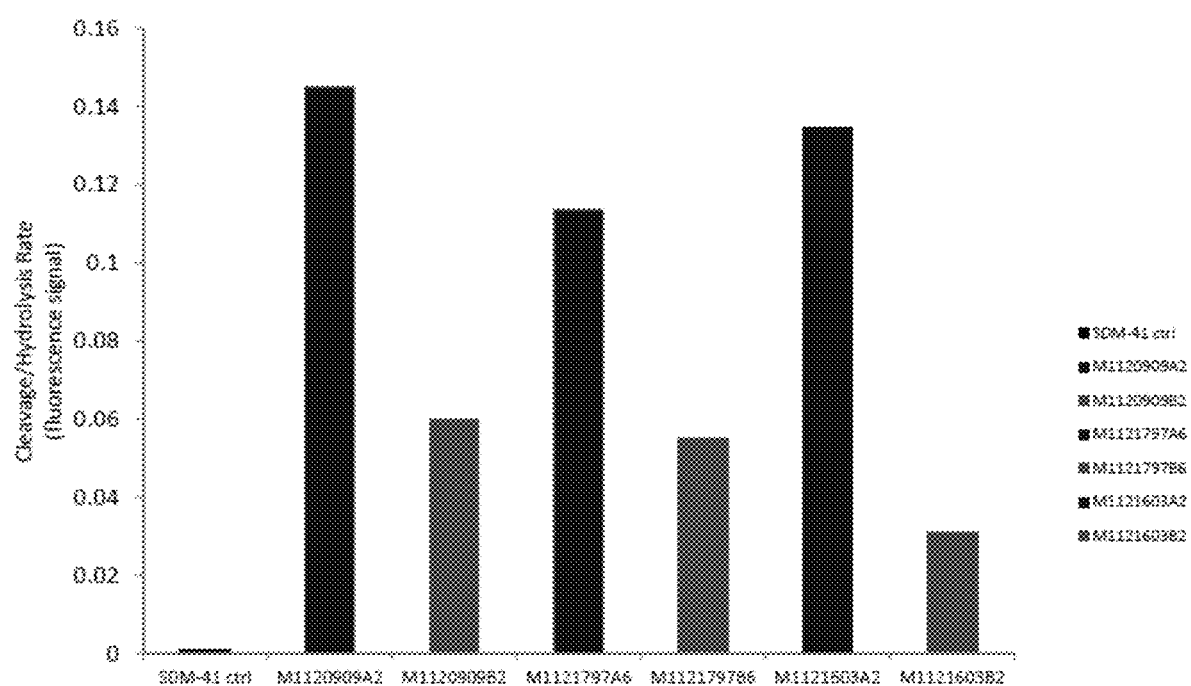
FIG. 6 exemplifies homogenized cancerous human breast tissue cleaving SDM-41 to a greater extent (~3-fold) than adjacent healthy tissue from the same patient (Example 8).

Human Ex Vivo Tissue Assay: SDM Cleavage and FRET Emission Ratio Response in Human Cancer Tissue Compared to Noncancerous Tissue Human breast cancer tissue samples and normal human breast tissue (provided by Cancer Human Tissue Network) were homogenized in cold TCNB buffer (pH 7.5, 50 mM Tris-HCl, 10 mM $CaCl_2$, 150 mM NaCl and 0.05% Brij35) at 100 mg/200 µL using ultrasonic disruption (VCX500, Sonics & Materials Inc, Newtown, Conn.). After homogenates were centrifuged at 15,000 g at 4° C. for 20 min, supernatants were collected. 500 nM of SDM-41 was used for the cleavage of 45 uL of tissue supernatant (final volume: 50 µL) in the assay unless otherwise noted. The assay was carried out using a SpectraMax M2 spectrometer with SoftMax Pro v4.5 software. Fluorescence signals of ($\lambda$ex, 620 nm, $\lambda$em, 670 nm), ($\lambda$ex, 620 nm, $\lambda$em, 773 nm) and ($\lambda$ex, 720 nm; $\lambda$em, 773 nm), where $\lambda$ex and $\lambda$em stand for excitation and emission wavelengths respectively, were measured as a function of time at room temperature. Samples were measured in triplicate. Table 1 shows the human breast cancer patient tissue used for the SDM-41 diagnostic fluorescence ex vivo assay. FIG. 5 shows the change in SDM-41 fluorescence ratio in homogenized cancerous and healthy tissue from breast cancer patients. The cancerous tissue (M112090A2, M1121603A2, and M1121797A6) cleaves SDM-41 faster than normal tissue ((M112090B2, M1121603B2, and M1121797B6) and enables diagnostic readout of cancerous breast cancer tissue. FIG. 6 shows the change in SDM-41 fluorescence ratio in homogenized cancerous and healthy tissue from the same breast cancer patients. The cancerous tissue cleaves SDM-41 faster and enables diagnostic readout of cancerous breast cancer tissue.

TABLE 1

|  | Age/Gender/Race | Diagnosis | Sample ID |
|---|---|---|---|
| Patient 1 | 63/female/white | Pleomorphic lobular carcinoma | Tumor: M1120909A2 Normal: M1120909B2 |
| Patient 2 | 69/female/white | Invasive ductal carcinoma | Tumor: M1121797A6 Normal: M1121797B6 |
| Patient 3 | 69/female/white | Invasive ductal carcinoma | Tumor: M1121603A2 Normal: M1121603B2 |

Example 9

Use of an SDM to to Visualize Cancer in Breast Cancer Patients

SDM-52 is delivered intravenously to a breast cancer patient. The fluorescent moieties on SDM-52 are taken up by cancerous cells and/or tissue after cleavage of the linker. A light source is shined onto the target tissue. The fluorescent moieties emit light wihich is detected by a camera or a detector. The data obtained by the camera or detector is processed to generate an image that allows the surgeon to visualize cancerous cells or tissue. The surgeon excises said tissue for biopsy.

Example 10

Use of an SDM to to Visualize Cancer in Prostate Cancer Patients

SDM-42 is delivered intravenously to a prostate cancer patient. The fluorescent moieties on SDM-42 are taken up by cancerous cells and/or tissue after cleavage of the linker. A light source is shined onto the target tissue. The fluorescent moieties emit light wihich is detected by a camera or a detector. The data obtained by the camera or detector is processed to generate an image that allows the surgeon to visualize cancerous cells or tissue. The surgeon excises said tissue for biopsy.

Example 11

Use of an SDM to to Visualize Cancer in Patients with Head and Neck (Squamous) Cancer SDM-48 is delivered intravenously to a head and neck cancer patient. The fluorescent moieties on SDM-48 are taken up by cancerous cells and/or tissue after cleavage of the linker. A light source is shined onto the target tissue. The fluorescent moieties emit light wihich is detected by a camera or a detector. The data obtained by the camera or detector is processed to generate an image that allows the surgeon to visualize cancerous cells or tissue. The surgeon excises said tissue for biopsy.

Example 12

Use of an SDM to to Visualize Cancer in Patients with Melanoma

SDM-60 is delivered intravenously to a patient having melanoma. The fluorescent moieties on SDM-60 are taken up by cancerous cells and/or tissue after cleavage of the linker. A light source is shined onto the target tissue. The fluorescent moieties emit light wihich is detected by a camera or a detector. The data obtained by the camera or detector is processed to generate an image that allows the surgeon to visualize cancerous cells or tissue. The surgeon excises said tissue for biopsy.

Example 13

Use of an SDM to to Visualize Cancer in Patients with Thyroid Cancer

SDM-62 is delivered intravenously to a thyroid cancer patient. The fluorescent moieties on SDM-62 are taken up by cancerous cells and/or tissue after cleavage of the linker. A light source is shined onto the target tissue. The fluorescent moieties emit light wihich is detected by a camera or a detector. The data obtained by the camera or detector is processed to generate an image that allows the surgeon to visualize cancerous cells or tissue. The surgeon excises said tissue for biopsy.

What is claimed is:
1. A peptide according to Peptide P-16, having the structure:
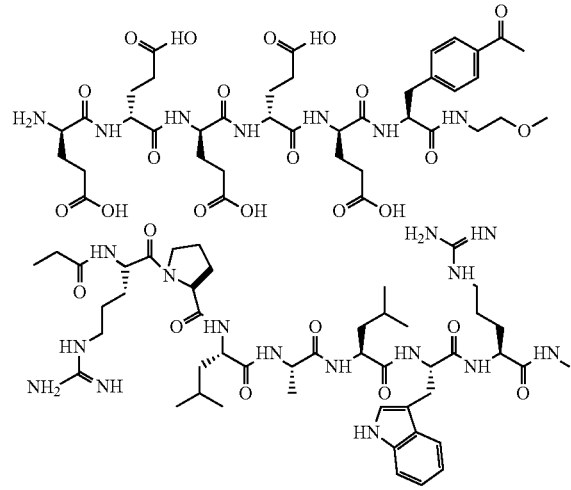
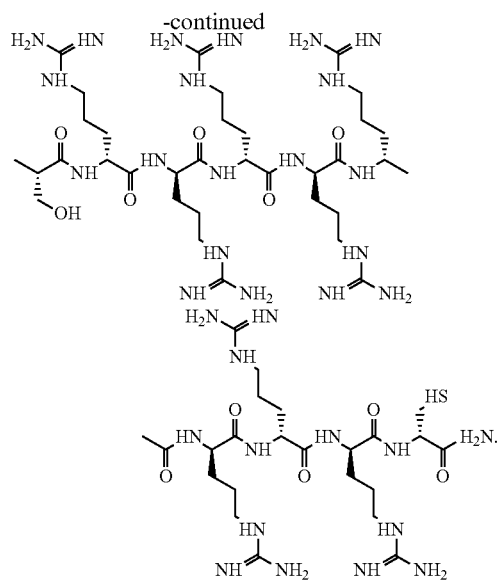
* * * * *

SEQUENCE LISTING

```
<160> NUMBER OF SEQ ID NOS: 33

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S-methyl-(L)-cysteine
```

```
<400> SEQUENCE: 1

Pro Leu Gly Cys Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Leu Gly Leu Ala Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Leu Ala Leu Trp Arg Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Glu Glu Glu Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Glu Glu Glu Glu Glu Glu Glu Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg Arg Arg
1               5

<210> SEQ ID NO 7
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ser Pro Ala Tyr Tyr Thr Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Pro Arg Ser Phe Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Pro Arg Ser Phe Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Gln Leu Lys Leu
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term acetyl

<400> SEQUENCE: 12
```

Arg Leu Gln Leu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(9)
<223> OTHER INFORMATION: This sequence may encompass 5-9 residues
      wherein some positions may be absent

<400> SEQUENCE: 13

Glu Glu Glu Glu Glu Glu Glu Glu Glu
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 5-8 residues
      wherein some positions may be absent

<400> SEQUENCE: 14

Glu Glu Glu Glu Glu Glu Glu Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(7)
<223> OTHER INFORMATION: This sequence may encompass 5-7 residues
      wherein some positions may be absent

<400> SEQUENCE: 15

Glu Glu Glu Glu Glu Glu Glu
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Glu Glu Glu Glu Glu
1               5

<210> SEQ ID NO 17
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 17

Glu Glu Glu Glu Glu Glu Glu
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Glu Glu Glu Glu Glu Glu Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Arg Arg Arg Arg Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 20

Pro Leu Gly Xaa Ala Gly
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Ala Ala Asn Leu Val Arg Gly Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 22

Ser Gly Arg Ile Gly Phe Leu Arg Thr Ala
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Arg Ser Ala
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Leu Gly
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Leu Ala Leu
1

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S-ethylcysteine

<400> SEQUENCE: 26

Pro Ile Cys Phe Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Pro Arg Gly Leu Pro Gly
1               5
```

```
<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Ser Ser Lys Leu Gln
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Val Leu Ala Ser Ser Ser Phe Gly Tyr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Ser Gln Asn Tyr Pro Ile Val Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Val Val Gln Ala Ser Cys Arg Leu Ala
1               5                   10

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Glu Val Asp
1

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33
Gly Trp Glu His Asp Gly
1               5
```